(12) United States Patent
Jones et al.

(10) Patent No.: US 12,043,823 B2
(45) Date of Patent: Jul. 23, 2024

(54) CELL CAPTURE AND EXPANSION

(71) Applicant: Terumo BCT, Inc., Lakewood, CO (US)

(72) Inventors: Mark E. Jones, Littleton, CO (US); Dalip Sethi, Thornton, CO (US); Dennis J. Hlavinka, Arvada, CO (US); Thomas J. Felt, Boulder, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 17/702,658

(22) Filed: Mar. 23, 2022

(65) Prior Publication Data

US 2022/0306978 A1 Sep. 29, 2022

Related U.S. Application Data

(60) Provisional application No. 63/304,467, filed on Jan. 28, 2022, provisional application No. 63/275,793, filed on Nov. 4, 2021, provisional application No. 63/275,389, filed on Nov. 3, 2021, provisional application No. 63/228,561, filed on Aug. 2, 2021, provisional application No. 63/227,293, filed on Jul. 29, 2021, provisional application No. 63/183,591, filed on May 3, 2021, provisional application No. 63/169,173, filed on Mar. 31, 2021, provisional application No. 63/165,060, filed on Mar. 23, 2021.

(51) Int. Cl.
| | |
|---|---|
| *C12M 1/12* | (2006.01) |
| *A61K 35/15* | (2015.01) |
| *C12M 1/10* | (2006.01) |
| *C12M 3/00* | (2006.01) |
| *C12N 5/00* | (2006.01) |
| *C12N 5/0789* | (2010.01) |

(52) U.S. Cl.
CPC ............. *C12M 25/10* (2013.01); *A61K 35/15* (2013.01); *C12M 1/10* (2013.01); *C12M 3/00* (2013.01); *C12N 5/0068* (2013.01); *C12N 5/0647* (2013.01); *C12N 2501/125* (2013.01); *C12N 2501/145* (2013.01); *C12N 2501/26* (2013.01); *C12N 2502/1358* (2013.01); *C12N 2533/52* (2013.01)

(58) Field of Classification Search
CPC ..................................................... C12M 25/10
See application file for complete search history.

(56) References Cited

U.S. PATENT DOCUMENTS

| | | |
|---|---|---|
| 2,997,077 A | 8/1961 | Rodrigues |
| 3,013,435 A | 12/1961 | Rodrigues |
| 3,067,915 A | 12/1962 | Shapiro et al. |
| 3,191,807 A | 6/1965 | Rodrigues |
| 3,283,727 A | 11/1966 | Rodrigues |
| 3,701,717 A | 10/1972 | Ingvorsen |
| 4,173,415 A | 11/1979 | Wyatt |
| 4,301,010 A | 11/1981 | Eddleman et al. |
| 4,301,118 A | 11/1981 | Eddleman et al. |
| 4,412,990 A | 11/1983 | Lundblad et al. |
| 4,418,691 A | 12/1983 | Yannas et al. |
| 4,439,901 A | 4/1984 | Eddleman |
| 4,478,829 A | 10/1984 | Landaburu et al. |
| 4,486,188 A | 12/1984 | Altshuler et al. |
| 4,509,695 A | 4/1985 | Bessman |
| 4,585,654 A | 4/1986 | Landaburu et al. |
| 4,618,586 A | 10/1986 | Walker |
| 4,629,686 A | 12/1986 | Gruenberg |
| 4,670,544 A | 6/1987 | Schwinn et al. |
| 4,727,059 A | 2/1988 | Binder et al. |
| 4,828,706 A | 5/1989 | Eddleman |
| 4,897,358 A | 1/1990 | Carrasco |
| 4,960,521 A | 10/1990 | Keller |
| 4,988,623 A | 1/1991 | Schwarz et al. |
| 5,015,585 A | 5/1991 | Robinson |
| 5,019,054 A | 5/1991 | Clement et al. |
| 5,126,238 A | 6/1992 | Gebhard et al. |
| 5,130,141 A | 7/1992 | Law et al. |

(Continued)

FOREIGN PATENT DOCUMENTS

| | | |
|---|---|---|
| CA | 1016332 A | 8/1977 |
| DE | 4007703 A1 | 9/1991 |

(Continued)

OTHER PUBLICATIONS

Cuchiara et al. Covalent immobilization of stem cell factor and stromal derived factor 1a for in vitro culture of hematopoietic progenitor cells (2013) Acta Biomaterialia, 9, pp. 9258-9269. (Year: 2013).*

Nankervis et al. Optimizing T Cell Expansion in a Hollow-Fiber Bioreactor (2018) Current Stem Cell Reports, 4, pp. 46-51 (Year: 2018).*

Fonseca-Pereira et al. The neurotrophic factor receptor RET drives haematopoietic stem cell survival and function (2014) Nature, 514, pp. 98-101 (Year: 2014).*

Boitano et al. Aryl Hydrocarbon Receptor Antagonists Promote the Expansion of Human Hematopoietic Stem Cells (2010) Science, 329, pp. 1345-1348. (Year: 2010).*

(Continued)

*Primary Examiner* — Kara D Johnson
*Assistant Examiner* — Maytee Marie Contes De Jesus
(74) *Attorney, Agent, or Firm* — Harness, Dickey & Pierce, P.L.C.

(57) ABSTRACT

Implementations are described that relate to methods and systems for growing cells in a hollow fiber bioreactor. In implementations, the cells may be exposed to a number of growth factors including a combination of recombinant growth factors. In other implementations, the cells may be grown in co-culture with other cells, e.g., hMSC's. In implementations, the cells may include CD34+ cells. A coated membrane includes a membrane having a first coating configured to promote cellular adhesion to the membrane and a second coating that includes a soluble protein moiety.

26 Claims, 21 Drawing Sheets

(56) References Cited

U.S. PATENT DOCUMENTS

| | | |
|---|---|---|
| 5,149,544 A | 9/1992 | Gentile et al. |
| 5,169,930 A | 12/1992 | Ruoslahti et al. |
| 5,192,553 A | 3/1993 | Boyse et al. |
| 5,197,985 A | 3/1993 | Caplan et al. |
| 5,202,254 A | 4/1993 | Amiot et al. |
| 5,225,346 A | 7/1993 | Matsumiya et al. |
| 5,226,914 A | 7/1993 | Caplan et al. |
| 5,240,614 A | 8/1993 | Ofsthun et al. |
| 5,240,861 A | 8/1993 | Bieri |
| 5,283,058 A | 2/1994 | Faustman |
| 5,310,676 A | 5/1994 | Johansson et al. |
| 5,324,428 A | 6/1994 | Flaherty |
| 5,342,752 A | 8/1994 | Platz et al. |
| 5,422,197 A | 6/1995 | Zito |
| 5,436,151 A | 7/1995 | McGlave et al. |
| 5,437,994 A | 8/1995 | Emerson et al. |
| 5,439,757 A | 8/1995 | Zito |
| 5,459,069 A | 10/1995 | Palsson et al. |
| 5,460,964 A | 10/1995 | McGlave et al. |
| H1509 H | 12/1995 | Eran et al. |
| 5,478,739 A | 12/1995 | Slivka et al. |
| 5,486,359 A | 1/1996 | Caplan et al. |
| 5,496,659 A | 3/1996 | Zito |
| 5,507,949 A | 4/1996 | Ho |
| 5,512,180 A | 4/1996 | Ho |
| 5,527,467 A | 6/1996 | Ofsthun et al. |
| 5,543,316 A | 8/1996 | Zawadzka et al. |
| 5,545,492 A | 8/1996 | Zito |
| 5,549,674 A | 8/1996 | Humes et al. |
| 5,571,720 A | 11/1996 | Grandics et al. |
| 5,591,625 A | 1/1997 | Gerson et al. |
| 5,593,580 A | 1/1997 | Kopf |
| 5,595,909 A | 1/1997 | Hu et al. |
| 5,599,703 A | 2/1997 | Davis et al. |
| 5,605,822 A | 2/1997 | Emerson et al. |
| 5,605,829 A | 2/1997 | McGlave et al. |
| 5,605,835 A | 2/1997 | Hu et al. |
| 5,622,857 A | 4/1997 | Goffe |
| 5,626,731 A | 5/1997 | Cooley et al. |
| 5,627,070 A | 5/1997 | Gruenberg |
| 5,635,386 A | 6/1997 | Palsson et al. |
| 5,635,387 A | 6/1997 | Fei et al. |
| 5,643,736 A | 7/1997 | Bruder et al. |
| 5,646,043 A | 7/1997 | Emerson et al. |
| 5,654,186 A | 8/1997 | Cerami et al. |
| 5,656,421 A | 8/1997 | Gebhard et al. |
| 5,658,995 A | 8/1997 | Kohn et al. |
| 5,667,985 A | 9/1997 | O'Leary et al. |
| 5,670,147 A | 9/1997 | Emerson et al. |
| 5,674,750 A | 10/1997 | Kraus et al. |
| 5,684,712 A | 11/1997 | Goffe et al. |
| 5,686,289 A | 11/1997 | Humes et al. |
| 5,695,989 A | 12/1997 | Kalamasz |
| 5,700,289 A | 12/1997 | Breitbart et al. |
| 5,705,534 A | 1/1998 | D'Agostino et al. |
| 5,707,859 A | 1/1998 | Miller et al. |
| 5,712,163 A | 1/1998 | Parenteau et al. |
| 5,728,581 A | 3/1998 | Schwartz et al. |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,750,651 A | 5/1998 | Oppermann et al. |
| 5,753,506 A | 5/1998 | Johe |
| 5,763,197 A | 6/1998 | Tsukamoto et al. |
| 5,763,266 A | 6/1998 | Palsson et al. |
| 5,766,944 A | 6/1998 | Ruiz |
| 5,772,994 A | 6/1998 | Ildstad et al. |
| 5,783,075 A | 7/1998 | Eddleman et al. |
| 5,783,216 A | 7/1998 | Faustman |
| 5,785,912 A | 7/1998 | Cooley et al. |
| 5,804,446 A | 9/1998 | Cerami et al. |
| 5,806,529 A | 9/1998 | Reisner et al. |
| 5,807,686 A | 9/1998 | Wagner et al. |
| 5,811,094 A | 9/1998 | Caplan et al. |
| 5,811,397 A | 9/1998 | Francavilla et al. |
| 5,817,773 A | 10/1998 | Wilson et al. |
| 5,821,218 A | 10/1998 | Toback et al. |
| 5,827,735 A | 10/1998 | Young et al. |
| 5,827,740 A | 10/1998 | Pittenger |
| 5,830,921 A | 11/1998 | Cooley et al. |
| 5,833,979 A | 11/1998 | Schinstine et al. |
| 5,837,258 A | 11/1998 | Grotendorst |
| 5,837,539 A | 11/1998 | Caplan et al. |
| 5,840,502 A | 11/1998 | Van Vlasselaer |
| 5,840,576 A | 11/1998 | Schinstine et al. |
| 5,840,580 A | 11/1998 | Terstappen et al. |
| 5,842,477 A | 12/1998 | Naughton et al. |
| 5,843,633 A | 12/1998 | Yin et al. |
| 5,846,796 A | 12/1998 | Cerami et al. |
| 5,853,247 A | 12/1998 | Shroyer |
| 5,853,717 A | 12/1998 | Schinstine et al. |
| 5,855,608 A | 1/1999 | Brekke et al. |
| 5,855,613 A | 1/1999 | Antanavich et al. |
| 5,855,619 A | 1/1999 | Caplan et al. |
| 5,858,747 A | 1/1999 | Schinstine et al. |
| 5,858,782 A | 1/1999 | Long et al. |
| 5,861,315 A | 1/1999 | Nakahata |
| 5,866,115 A | 2/1999 | Kanz et al. |
| 5,866,420 A | 2/1999 | Talbot et al. |
| 5,868,930 A | 2/1999 | Kopf |
| 5,882,295 A | 3/1999 | Kope |
| 5,882,918 A | 3/1999 | Goffe |
| 5,882,929 A | 3/1999 | Fofonoff et al. |
| 5,888,807 A | 3/1999 | Palsson et al. |
| 5,902,741 A | 5/1999 | Purchio et al. |
| 5,906,827 A | 5/1999 | Khouri et al. |
| 5,906,934 A | 5/1999 | Grande et al. |
| 5,908,782 A | 6/1999 | Marshak et al. |
| 5,908,784 A | 6/1999 | Johnstone et al. |
| 5,912,177 A | 6/1999 | Turner et al. |
| 5,914,108 A | 6/1999 | Tsukamoto et al. |
| 5,922,597 A | 7/1999 | Verfaillie et al. |
| 5,922,847 A | 7/1999 | Broudy et al. |
| 5,925,567 A | 7/1999 | Kraus et al. |
| 5,928,945 A | 7/1999 | Seliktar et al. |
| 5,935,849 A | 8/1999 | Schinstine et al. |
| 5,938,929 A | 8/1999 | Shimagaki et al. |
| 5,939,323 A | 8/1999 | Valentini et al. |
| 5,942,225 A | 8/1999 | Bruder et al. |
| 5,955,353 A | 9/1999 | Amiot |
| 5,958,763 A | 9/1999 | Goffe |
| 5,965,436 A | 10/1999 | Thiede et al. |
| 5,972,703 A | 10/1999 | Long et al. |
| 5,980,795 A | 11/1999 | Klotzer et al. |
| 5,981,211 A | 11/1999 | Hu et al. |
| 5,981,708 A | 11/1999 | Lawman et al. |
| 5,998,184 A | 12/1999 | Shi |
| 6,001,585 A | 12/1999 | Gramer |
| 6,001,643 A | 12/1999 | Spaulding |
| 6,001,647 A | 12/1999 | Peck et al. |
| 6,004,743 A | 12/1999 | Kenyon et al. |
| 6,010,696 A | 1/2000 | Caplan et al. |
| 6,015,554 A | 1/2000 | Galy |
| 6,022,540 A | 2/2000 | Bruder et al. |
| 6,022,742 A | 2/2000 | Kopf |
| 6,022,743 A | 2/2000 | Naughton et al. |
| 6,027,743 A | 2/2000 | Khouri et al. |
| 6,030,836 A | 2/2000 | Thiede et al. |
| 6,040,180 A | 3/2000 | Johe |
| 6,045,818 A | 4/2000 | Cima et al. |
| 6,048,721 A | 4/2000 | Armstrong et al. |
| 6,048,727 A | 4/2000 | Kopf |
| 6,049,026 A | 4/2000 | Muschler |
| 6,054,121 A | 4/2000 | Cerami et al. |
| 6,060,270 A | 5/2000 | Humes |
| 6,066,317 A | 5/2000 | Yang et al. |
| 6,071,691 A | 6/2000 | Hoekstra et al. |
| 6,074,366 A | 6/2000 | Rogers et al. |
| 6,082,364 A | 7/2000 | Balian et al. |
| 6,083,747 A | 7/2000 | Wong et al. |
| 6,086,643 A | 7/2000 | Clark et al. |
| 6,087,113 A | 7/2000 | Caplan et al. |
| 6,096,537 A | 8/2000 | Chappel |

(56) References Cited

U.S. PATENT DOCUMENTS

| | | |
|---|---|---|
| 6,103,117 A | 8/2000 | Shimagaki et al. |
| 6,103,522 A | 8/2000 | Torok-Storb et al. |
| 6,110,176 A | 8/2000 | Shapira |
| 6,110,482 A | 8/2000 | Khouri et al. |
| 6,114,307 A | 9/2000 | Jaspers et al. |
| 6,117,985 A | 9/2000 | Thomas et al. |
| 6,120,491 A | 9/2000 | Kohn et al. |
| 6,127,141 A | 10/2000 | Kopf |
| 6,129,911 A | 10/2000 | Faris |
| 6,143,293 A | 11/2000 | Weiss et al. |
| 6,146,360 A | 11/2000 | Rogers et al. |
| 6,146,888 A | 11/2000 | Smith et al. |
| 6,149,902 A | 11/2000 | Artavanis-Tsakonas et al. |
| 6,149,906 A | 11/2000 | Mosca |
| 6,150,164 A | 11/2000 | Humes |
| 6,152,964 A | 11/2000 | Van Blitterswijk et al. |
| 6,162,643 A | 12/2000 | Wille, Jr. |
| 6,165,225 A | 12/2000 | Antanavich et al. |
| 6,165,785 A | 12/2000 | Ogle et al. |
| 6,174,333 B1 | 1/2001 | Kadiyala et al. |
| 6,174,526 B1 | 1/2001 | Cerami et al. |
| 6,174,666 B1 | 1/2001 | Pavlakis et al. |
| 6,179,871 B1 | 1/2001 | Halpern |
| 6,197,325 B1 | 3/2001 | MacPhee et al. |
| 6,197,575 B1 | 3/2001 | Griffith et al. |
| 6,200,606 B1 | 3/2001 | Peterson et al. |
| 6,214,369 B1 | 4/2001 | Grande et al. |
| 6,214,574 B1 | 4/2001 | Kopf |
| 6,224,860 B1 | 5/2001 | Brown |
| 6,225,119 B1 | 5/2001 | Qasba et al. |
| 6,225,368 B1 | 5/2001 | D'Agostino et al. |
| 6,228,117 B1 | 5/2001 | De Bruijn et al. |
| 6,228,607 B1 | 5/2001 | Kersten et al. |
| 6,238,908 B1 | 5/2001 | Armstrong et al. |
| 6,239,157 B1 | 5/2001 | Mbalaviele |
| 6,242,252 B1 | 6/2001 | Reid et al. |
| 6,248,319 B1 | 6/2001 | Zsebo et al. |
| 6,248,587 B1 | 6/2001 | Rodgers et al. |
| 6,255,112 B1 | 7/2001 | Thiede et al. |
| 6,258,597 B1 | 7/2001 | Bachovchin et al. |
| 6,258,778 B1 | 7/2001 | Rodgers et al. |
| 6,261,549 B1 | 7/2001 | Fernandez et al. |
| 6,280,718 B1 | 8/2001 | Kaufman et al. |
| 6,280,724 B1 | 8/2001 | Moore |
| 6,281,012 B1 | 8/2001 | McIntosh et al. |
| 6,281,195 B1 | 8/2001 | Rueger et al. |
| 6,287,864 B1 | 9/2001 | Bagnis et al. |
| 6,291,249 B1 | 9/2001 | Mahant et al. |
| 6,297,213 B1 | 10/2001 | Oppermann et al. |
| 6,299,650 B1 | 10/2001 | Van Blitterswijk et al. |
| 6,306,424 B1 | 10/2001 | Vyakarnam et al. |
| 6,306,575 B1 | 10/2001 | Thomas et al. |
| 6,322,784 B1 | 11/2001 | Pittenger et al. |
| 6,322,786 B1 | 11/2001 | Anderson |
| 6,326,198 B1 | 12/2001 | Emerson et al. |
| 6,326,201 B1 | 12/2001 | Fung et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,338,942 B2 | 1/2002 | Kraus et al. |
| 6,340,592 B1 | 1/2002 | Stringer |
| 6,342,370 B1 | 1/2002 | Connolly et al. |
| 6,355,239 B1 | 3/2002 | Bruder et al. |
| 6,358,252 B1 | 3/2002 | Shapira |
| 6,361,997 B1 | 3/2002 | Huss |
| 6,365,149 B2 | 4/2002 | Vyakarnam et al. |
| 6,368,636 B1 | 4/2002 | McIntosh et al. |
| 6,372,210 B2 | 4/2002 | Brown |
| 6,372,244 B1 | 4/2002 | Antanavich et al. |
| 6,372,494 B1 | 4/2002 | Naughton et al. |
| 6,372,892 B1 | 4/2002 | Ballinger et al. |
| 6,376,742 B1 | 4/2002 | Zdrahala et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,387,693 B2 | 5/2002 | Rieser et al. |
| 6,387,964 B1 | 5/2002 | D'Agostino et al. |
| 6,392,118 B1 | 5/2002 | Hammang et al. |
| 6,394,812 B1 | 5/2002 | Sullivan et al. |
| 6,399,580 B1 | 6/2002 | Elias et al. |
| 6,410,320 B1 | 6/2002 | Humes |
| 6,414,219 B1 | 7/2002 | Denhardt et al. |
| 6,416,496 B1 | 7/2002 | Rogers et al. |
| 6,417,205 B1 | 7/2002 | Cooke et al. |
| 6,419,829 B2 | 7/2002 | Ho et al. |
| 6,420,138 B1 | 7/2002 | Gentz et al. |
| 6,423,681 B1 | 7/2002 | Barasch et al. |
| 6,426,332 B1 | 7/2002 | Rueger et al. |
| 6,428,802 B1 | 8/2002 | Atala |
| 6,429,012 B1 | 8/2002 | Kraus et al. |
| 6,429,013 B1 | 8/2002 | Halvorsen et al. |
| 6,432,653 B1 | 8/2002 | Okarma |
| 6,432,711 B1 | 8/2002 | Dinsmore et al. |
| 6,440,407 B1 | 8/2002 | Bauer et al. |
| 6,440,734 B1 | 8/2002 | Pykett et al. |
| 6,451,562 B1 | 9/2002 | Ruben et al. |
| 6,454,811 B1 | 9/2002 | Sherwood et al. |
| 6,455,678 B1 | 9/2002 | Yin et al. |
| 6,458,585 B1 | 10/2002 | Vachula et al. |
| 6,458,589 B1 | 10/2002 | Rambhatla et al. |
| 6,461,495 B1 | 10/2002 | Morrissey et al. |
| 6,461,853 B1 | 10/2002 | Zhu |
| 6,464,983 B1 | 10/2002 | Grotendorst |
| 6,465,205 B2 | 10/2002 | Hicks, Jr. |
| 6,465,247 B1 | 10/2002 | Weissman et al. |
| 6,465,249 B2 | 10/2002 | Reya et al. |
| 6,468,794 B1 | 10/2002 | Uchida et al. |
| 6,472,200 B1 | 10/2002 | Mitrani |
| 6,475,481 B2 | 11/2002 | Talmadge |
| 6,479,064 B1 | 11/2002 | Atala |
| 6,482,231 B1 | 11/2002 | Abatangelo et al. |
| 6,482,411 B1 | 11/2002 | Ahuja et al. |
| 6,482,645 B2 | 11/2002 | Atala |
| 6,482,926 B1 | 11/2002 | Thomas et al. |
| 6,488,925 B2 | 12/2002 | Ruben et al. |
| 6,491,918 B1 | 12/2002 | Thomas et al. |
| 6,495,129 B1 | 12/2002 | Li et al. |
| 6,495,364 B2 | 12/2002 | Hammang et al. |
| 6,497,875 B1 | 12/2002 | Sorrell et al. |
| 6,498,034 B1 | 12/2002 | Strobl |
| 6,506,574 B1 | 1/2003 | Rambhatla et al. |
| 6,511,510 B1 | 1/2003 | de Bruijn et al. |
| 6,511,767 B1 | 1/2003 | Calver et al. |
| 6,511,958 B1 | 1/2003 | Atkinson et al. |
| 6,514,514 B1 | 2/2003 | Atkinson et al. |
| 6,524,452 B1 | 2/2003 | Clark et al. |
| 6,528,052 B1 | 3/2003 | Smith et al. |
| 6,528,245 B2 | 3/2003 | Sanchez-Ramos et al. |
| 6,531,445 B1 | 3/2003 | Cohen et al. |
| 6,534,084 B1 | 3/2003 | Vyakarnam et al. |
| 6,537,807 B1 | 3/2003 | Smith et al. |
| 6,541,024 B1 | 4/2003 | Kadiyala et al. |
| 6,541,249 B2 | 4/2003 | Wager et al. |
| 6,544,506 B2 | 4/2003 | Reisner |
| 6,548,734 B1 | 4/2003 | Glimcher et al. |
| 6,555,324 B1 | 4/2003 | Olweus et al. |
| 6,555,374 B1 | 4/2003 | Gimble et al. |
| 6,559,119 B1 | 5/2003 | Burgess et al. |
| 6,562,616 B1 | 5/2003 | Toner et al. |
| 6,565,843 B1 | 5/2003 | Cohen et al. |
| 6,569,421 B2 | 5/2003 | Hodges |
| 6,569,427 B1 | 5/2003 | Boyse et al. |
| 6,569,428 B1 | 5/2003 | Isner et al. |
| 6,569,654 B2 | 5/2003 | Shastri et al. |
| 6,576,188 B1 | 6/2003 | Rose et al. |
| 6,576,428 B1 | 6/2003 | Assenmacher et al. |
| 6,576,464 B2 | 6/2003 | Gold et al. |
| 6,576,465 B1 | 6/2003 | Long |
| 6,582,471 B1 | 6/2003 | Bittmann et al. |
| 6,582,955 B2 | 6/2003 | Martinez et al. |
| 6,586,192 B1 | 7/2003 | Peschle et al. |
| 6,589,728 B2 | 7/2003 | Csete et al. |
| 6,589,786 B1 | 7/2003 | Mangano et al. |

(56) References Cited

U.S. PATENT DOCUMENTS

| | | |
|---|---|---|
| 6,596,274 B1 | 7/2003 | Abatangelo et al. |
| 6,599,300 B2 | 7/2003 | Vibe-Hansen et al. |
| 6,599,520 B2 | 7/2003 | Scarborough et al. |
| 6,610,535 B1 | 8/2003 | Lu et al. |
| 6,613,798 B1 | 9/2003 | Porter et al. |
| 6,616,912 B2 | 9/2003 | Eddleman et al. |
| 6,617,070 B1 | 9/2003 | Morrissey et al. |
| 6,617,152 B2 | 9/2003 | Bryhan et al. |
| 6,617,159 B1 | 9/2003 | Cancedda et al. |
| 6,623,749 B2 | 9/2003 | Williams et al. |
| 6,623,942 B2 | 9/2003 | Ruben et al. |
| 6,624,108 B1 | 9/2003 | Clark et al. |
| 6,626,950 B2 | 9/2003 | Brown et al. |
| 6,627,191 B1 | 9/2003 | Bartelmez et al. |
| 6,632,425 B1 | 10/2003 | Li et al. |
| 6,632,620 B1 | 10/2003 | Makarovskiy |
| 6,632,934 B1 | 10/2003 | Moreadith et al. |
| 6,638,765 B1 | 10/2003 | Rosenberg |
| 6,642,048 B2 | 11/2003 | Xu et al. |
| 6,642,049 B1 | 11/2003 | Chute et al. |
| 6,642,201 B1 | 11/2003 | Khavinson et al. |
| 6,645,489 B2 | 11/2003 | Pykett et al. |
| 6,645,727 B2 | 11/2003 | Thomas et al. |
| 6,645,763 B2 | 11/2003 | Kobayashi et al. |
| 6,649,189 B2 | 11/2003 | Talmadge et al. |
| 6,649,595 B2 | 11/2003 | Clackson et al. |
| 6,649,631 B1 | 11/2003 | Orme et al. |
| 6,653,105 B2 | 11/2003 | Triglia et al. |
| 6,653,134 B2 | 11/2003 | Prockop et al. |
| 6,660,523 B2 | 12/2003 | Blom et al. |
| 6,662,805 B2 | 12/2003 | Frondoza et al. |
| 6,667,034 B2 | 12/2003 | Palsson et al. |
| 6,667,176 B1 | 12/2003 | Funk et al. |
| 6,670,169 B1 | 12/2003 | Schob et al. |
| 6,670,175 B2 | 12/2003 | Wang et al. |
| 6,673,603 B2 | 1/2004 | Baetge et al. |
| 6,673,606 B1 | 1/2004 | Tennekoon et al. |
| 6,677,306 B1 | 1/2004 | Veis et al. |
| 6,683,192 B2 | 1/2004 | Baxter et al. |
| 6,685,936 B2 | 2/2004 | McIntosh et al. |
| 6,685,971 B2 | 2/2004 | Xu |
| 6,686,198 B1 | 2/2004 | Melton et al. |
| 6,696,575 B2 | 2/2004 | Schmidt et al. |
| 6,699,716 B2 | 3/2004 | Sullivan et al. |
| 6,703,017 B1 | 3/2004 | Peck et al. |
| 6,703,209 B1 | 3/2004 | Baetscher et al. |
| 6,706,293 B1 | 3/2004 | Quintanilla Almagro et al. |
| 6,709,864 B1 | 3/2004 | Pittenger et al. |
| 6,712,850 B2 | 3/2004 | Vyakarnam et al. |
| 6,719,969 B1 | 4/2004 | Hogaboam et al. |
| 6,719,970 B1 | 4/2004 | Costantino et al. |
| 6,720,340 B1 | 4/2004 | Cooke et al. |
| 6,730,314 B2 | 5/2004 | Jeschke et al. |
| 6,730,315 B2 | 5/2004 | Usala et al. |
| 6,730,510 B2 | 5/2004 | Roos et al. |
| 6,733,746 B2 | 5/2004 | Daley et al. |
| 6,734,000 B2 | 5/2004 | Chin et al. |
| 6,740,493 B1 | 5/2004 | Long et al. |
| 6,759,039 B2 | 7/2004 | Tsang et al. |
| 6,759,245 B1 | 7/2004 | Toner et al. |
| 6,761,883 B2 | 7/2004 | Weissman et al. |
| 6,761,887 B1 | 7/2004 | Kavalkovich et al. |
| 6,767,699 B2 | 7/2004 | Polo et al. |
| 6,767,737 B1 | 7/2004 | Wilson et al. |
| 6,767,738 B1 | 7/2004 | Gage et al. |
| 6,767,740 B2 | 7/2004 | Sramek et al. |
| 6,770,478 B2 | 8/2004 | Crowe et al. |
| 6,777,227 B2 | 8/2004 | Ricci et al. |
| 6,777,231 B1 | 8/2004 | Katz et al. |
| 6,780,612 B1 | 8/2004 | Ford et al. |
| 6,787,355 B1 | 9/2004 | Miller et al. |
| 6,790,455 B2 | 9/2004 | Chu et al. |
| 6,793,939 B2 | 9/2004 | Badylak |
| 6,797,269 B2 | 9/2004 | Mosca et al. |
| 6,797,514 B2 | 9/2004 | Berenson et al. |
| 6,800,480 B1 | 10/2004 | Bodnar et al. |
| 6,802,971 B2 | 10/2004 | Gorsuch et al. |
| 6,805,860 B1 | 10/2004 | Alt |
| 6,809,117 B2 | 10/2004 | Enikolopov et al. |
| 6,811,773 B1 | 11/2004 | Gentz et al. |
| 6,811,776 B2 | 11/2004 | Kale et al. |
| 6,814,961 B1 | 11/2004 | Jensen et al. |
| 6,821,513 B1 | 11/2004 | Fleming |
| 6,821,790 B2 | 11/2004 | Mahant et al. |
| 6,828,145 B2 | 12/2004 | Avital et al. |
| 6,833,269 B2 | 12/2004 | Carpenter |
| 6,835,377 B2 | 12/2004 | Goldberg et al. |
| 6,835,566 B2 | 12/2004 | Smith et al. |
| 6,838,284 B2 | 1/2005 | de Bruijn et al. |
| 6,841,150 B2 | 1/2005 | Halvorsen et al. |
| 6,841,151 B2 | 1/2005 | Stringer |
| 6,841,294 B1 | 1/2005 | Morrissey et al. |
| 6,841,355 B2 | 1/2005 | Livant |
| 6,841,386 B2 | 1/2005 | Kraus et al. |
| 6,841,542 B2 | 1/2005 | Bartelmez et al. |
| 6,844,011 B1 | 1/2005 | Faustman |
| 6,849,051 B2 | 2/2005 | Sramek et al. |
| 6,849,255 B2 | 2/2005 | Gazit et al. |
| 6,849,454 B2 | 2/2005 | Kelly et al. |
| 6,849,662 B2 | 2/2005 | Enikolopov et al. |
| 6,852,308 B2 | 2/2005 | Kohn et al. |
| 6,852,321 B2 | 2/2005 | Colucci et al. |
| 6,852,533 B1 | 2/2005 | Rafii et al. |
| 6,855,242 B1 | 2/2005 | Comninellis et al. |
| 6,855,542 B2 | 2/2005 | DiMilla et al. |
| 6,863,900 B2 | 3/2005 | Kadiyala et al. |
| 6,866,843 B2 | 3/2005 | Habener et al. |
| 6,872,389 B1 | 3/2005 | Faris |
| 6,875,430 B2 | 4/2005 | McIntosh et al. |
| 6,887,600 B2 | 5/2005 | Morrissey et al. |
| 6,887,704 B2 | 5/2005 | Peled et al. |
| 6,908,763 B1 | 6/2005 | Akashi et al. |
| 6,911,201 B1 | 6/2005 | Merchav et al. |
| 6,914,279 B2 | 7/2005 | Lu et al. |
| 6,939,955 B2 | 9/2005 | Rameshwar |
| 6,965,018 B2 | 11/2005 | Mikesell et al. |
| 6,979,321 B2 | 12/2005 | Geis et al. |
| 6,988,004 B2 | 1/2006 | Kanno et al. |
| 7,008,394 B2 | 3/2006 | Geise et al. |
| 7,015,037 B1 | 3/2006 | Furcht et al. |
| 7,029,666 B2 | 4/2006 | Bruder et al. |
| 7,033,339 B1 | 4/2006 | Lynn |
| 7,045,098 B2 | 5/2006 | Stephens |
| 7,052,517 B2 | 5/2006 | Murphy et al. |
| 7,056,493 B2 | 6/2006 | Kohn et al. |
| 7,118,672 B2 | 10/2006 | Husain et al. |
| 7,122,178 B1 | 10/2006 | Simmons et al. |
| 7,160,719 B2 | 1/2007 | Nyberg |
| 7,169,295 B2 | 1/2007 | Husain et al. |
| 7,172,696 B1 | 2/2007 | Martinez et al. |
| 7,175,763 B2 | 2/2007 | Husain et al. |
| 7,192,776 B2 | 3/2007 | Stephens |
| 7,195,711 B2 | 3/2007 | Gorsuch et al. |
| 7,250,154 B2 | 7/2007 | Kohn et al. |
| 7,271,234 B2 | 9/2007 | Kohn et al. |
| 7,294,259 B2 | 11/2007 | Cote et al. |
| 7,300,571 B2 | 11/2007 | Cote et al. |
| 7,303,676 B2 | 12/2007 | Husain et al. |
| 7,303,677 B2 | 12/2007 | Cote et al. |
| 7,341,062 B2 | 3/2008 | Chachques et al. |
| 7,358,001 B2 | 4/2008 | Morrissey et al. |
| 7,361,493 B1 | 4/2008 | Hammond et al. |
| 7,368,169 B2 | 5/2008 | Kohn et al. |
| 7,378,271 B2 | 5/2008 | Bader |
| 7,399,872 B2 | 7/2008 | Webster et al. |
| 7,416,884 B2 | 8/2008 | Gemmiti et al. |
| 7,425,440 B2 | 9/2008 | Malinge et al. |
| 7,435,586 B2 | 10/2008 | Bartlett et al. |
| 7,438,902 B2 | 10/2008 | Habener et al. |
| 7,439,057 B2 | 10/2008 | Frangos et al. |
| 7,452,529 B2 | 11/2008 | Brown, Jr. et al. |
| 7,491,388 B1 | 2/2009 | McIntosh et al. |
| 7,494,811 B2 | 2/2009 | Wolfinbarger, Jr. et al. |
| 7,514,074 B2 | 4/2009 | Pittenger et al. |

(56) References Cited

U.S. PATENT DOCUMENTS

| | | |
|---|---|---|
| 7,514,075 B2 | 4/2009 | Hedrick et al. |
| 7,524,676 B2 | 4/2009 | Reiter et al. |
| 7,534,609 B2 | 5/2009 | Merchav et al. |
| 7,572,374 B2 | 8/2009 | Gorsuch et al. |
| 7,579,179 B2 | 8/2009 | Bryhan et al. |
| 7,585,412 B2 | 9/2009 | Gorsuch et al. |
| 7,588,938 B2 | 9/2009 | Ma |
| 7,598,075 B2 | 10/2009 | Smith et al. |
| 7,608,447 B2 | 10/2009 | Cohen et al. |
| 7,659,118 B2 | 2/2010 | Furcht et al. |
| 7,678,573 B2 | 3/2010 | Merchav et al. |
| 7,682,823 B1 | 3/2010 | Runyon |
| 7,722,896 B2 | 5/2010 | Kohn et al. |
| D620,732 S | 8/2010 | Andrews |
| 7,838,122 B2 | 11/2010 | Kohn et al. |
| 7,838,289 B2 | 11/2010 | Furcht et al. |
| 7,892,829 B2 | 2/2011 | Pittenger et al. |
| 7,919,307 B2 | 4/2011 | Klaus et al. |
| 7,927,587 B2 | 4/2011 | Blazer et al. |
| 7,989,851 B2 | 8/2011 | Lu et al. |
| 8,008,528 B2 | 8/2011 | Kohn et al. |
| 8,034,365 B2 | 10/2011 | Baluca |
| 8,075,881 B2 | 12/2011 | Verfaillie et al. |
| 8,147,824 B2 | 4/2012 | Maziarz et al. |
| 8,147,863 B2 | 4/2012 | Kohn et al. |
| 8,158,120 B2 | 4/2012 | Pittenger et al. |
| 8,158,121 B2 | 4/2012 | Pittenger et al. |
| 8,252,280 B1 | 8/2012 | Verfaillie et al. |
| 8,252,887 B2 | 8/2012 | Bolikal et al. |
| 8,288,159 B2 | 10/2012 | Warren et al. |
| 8,288,590 B2 | 10/2012 | Kohn et al. |
| 8,298,823 B2 | 10/2012 | Warren et al. |
| 8,361,453 B2 | 1/2013 | Uhrich et al. |
| 8,377,683 B2 | 2/2013 | Lu et al. |
| 8,383,397 B2 | 2/2013 | Wojciechowski et al. |
| 8,383,806 B2 | 2/2013 | Rameshwar |
| 8,399,245 B2 | 3/2013 | Leuthaeuser et al. |
| 8,415,449 B2 | 4/2013 | Kohn et al. |
| 8,435,781 B2 | 5/2013 | Kodama |
| 8,461,289 B2 | 6/2013 | Kohn et al. |
| 8,476,399 B2 | 7/2013 | Bolikal et al. |
| 8,486,621 B2 | 7/2013 | Luo et al. |
| 8,486,695 B2 | 7/2013 | Danilkovitch et al. |
| 8,492,140 B2 | 7/2013 | Smith et al. |
| 8,492,150 B2 | 7/2013 | Parker et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,551,511 B2 | 10/2013 | Brandom et al. |
| 8,580,249 B2 | 11/2013 | Blazar et al. |
| 8,678,638 B2 | 3/2014 | Wong |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 9,109,193 B2 | 8/2015 | Galliher et al. |
| 9,220,810 B2 | 12/2015 | Ma et al. |
| 9,441,195 B2 | 9/2016 | Wojciechowski et al. |
| 9,534,198 B2 | 1/2017 | Page et al. |
| 9,732,313 B2 | 8/2017 | Hirschel et al. |
| 10,093,956 B2 | 10/2018 | Hirschel et al. |
| 10,494,421 B2 | 12/2019 | Castillo |
| 2001/0017188 A1 | 8/2001 | Cooley et al. |
| 2001/0020086 A1 | 9/2001 | Hubbell et al. |
| 2001/0021516 A1 | 9/2001 | Wei et al. |
| 2001/0029046 A1 | 10/2001 | Beaulieu |
| 2001/0033834 A1 | 10/2001 | Wilkison et al. |
| 2001/0036663 A1 | 11/2001 | Kraus et al. |
| 2001/0041687 A1 | 11/2001 | Mruk |
| 2001/0044413 A1 | 11/2001 | Pierce et al. |
| 2001/0049139 A1 | 12/2001 | Lagasse et al. |
| 2002/0015724 A1 | 2/2002 | Yang et al. |
| 2002/0018804 A1 | 2/2002 | Austin et al. |
| 2002/0028510 A1 | 3/2002 | Sanberg et al. |
| 2002/0031757 A1 | 3/2002 | Ohgushi et al. |
| 2002/0037278 A1 | 3/2002 | Ueno et al. |
| 2002/0045260 A1 | 4/2002 | Hung et al. |
| 2002/0064869 A1 | 5/2002 | Ebner et al. |
| 2002/0076400 A1 | 6/2002 | Katz et al. |
| 2002/0077687 A1 | 6/2002 | Ahn |
| 2002/0082698 A1 | 6/2002 | Parenteau et al. |
| 2002/0116054 A1 | 8/2002 | Lundell et al. |
| 2002/0128581 A1 | 9/2002 | Vishnoi et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0130100 A1 | 9/2002 | Smith |
| 2002/0132343 A1 | 9/2002 | Lum |
| 2002/0139743 A1 | 10/2002 | Critz et al. |
| 2002/0142457 A1 | 10/2002 | Umezawa et al. |
| 2002/0146678 A1 | 10/2002 | Benvenisty |
| 2002/0146817 A1 | 10/2002 | Cannon et al. |
| 2002/0150989 A1 | 10/2002 | Greene et al. |
| 2002/0151056 A1 | 10/2002 | Sasai et al. |
| 2002/0159981 A1 | 10/2002 | Peled et al. |
| 2002/0160032 A1 | 10/2002 | Long et al. |
| 2002/0160510 A1 | 10/2002 | Hariri |
| 2002/0168765 A1 | 11/2002 | Prockop et al. |
| 2002/0169408 A1 | 11/2002 | Beretta et al. |
| 2002/0182241 A1 | 12/2002 | Borenstein et al. |
| 2002/0182664 A1 | 12/2002 | Dolecek et al. |
| 2002/0188962 A1 | 12/2002 | Denhardt et al. |
| 2002/0197240 A1 | 12/2002 | Chiu |
| 2003/0021850 A1 | 1/2003 | Xu |
| 2003/0022390 A1 | 1/2003 | Stephens |
| 2003/0027330 A1 | 2/2003 | Lanza et al. |
| 2003/0027331 A1 | 2/2003 | Yan et al. |
| 2003/0032143 A1 | 2/2003 | Neff et al. |
| 2003/0036168 A1 | 2/2003 | Ni et al. |
| 2003/0040113 A1 | 2/2003 | Mizuno et al. |
| 2003/0049236 A1 | 3/2003 | Kassem et al. |
| 2003/0054331 A1 | 3/2003 | Fraser et al. |
| 2003/0059851 A1 | 3/2003 | Smith |
| 2003/0059939 A1 | 3/2003 | Page et al. |
| 2003/0078345 A1 | 4/2003 | Morrisey |
| 2003/0082795 A1 | 5/2003 | Shuler et al. |
| 2003/0086915 A1 | 5/2003 | Rader et al. |
| 2003/0089471 A1 | 5/2003 | Gehr et al. |
| 2003/0092101 A1 | 5/2003 | Ni et al. |
| 2003/0101465 A1 | 5/2003 | Lawman et al. |
| 2003/0103957 A1 | 6/2003 | McKerracher |
| 2003/0104568 A1 | 6/2003 | Lee |
| 2003/0113813 A1 | 6/2003 | Heidaran et al. |
| 2003/0113910 A1 | 6/2003 | Levanduski |
| 2003/0124091 A1 | 7/2003 | Tuse et al. |
| 2003/0124721 A1 | 7/2003 | Cheatham et al. |
| 2003/0130593 A1 | 7/2003 | Gonzalez |
| 2003/0133918 A1 | 7/2003 | Sherley |
| 2003/0138950 A1 | 7/2003 | McAllister et al. |
| 2003/0143727 A1 | 7/2003 | Chang |
| 2003/0148152 A1 | 8/2003 | Morrisey |
| 2003/0149011 A1 | 8/2003 | Ackerman et al. |
| 2003/0152558 A1 | 8/2003 | Luft et al. |
| 2003/0157078 A1 | 8/2003 | Hall et al. |
| 2003/0157709 A1 | 8/2003 | DiMilla et al. |
| 2003/0161817 A1 | 8/2003 | Young et al. |
| 2003/0166272 A1 | 9/2003 | Abuljadayel |
| 2003/0170214 A1 | 9/2003 | Bader |
| 2003/0180296 A1 | 9/2003 | Salcedo et al. |
| 2003/0185817 A1 | 10/2003 | Thomas et al. |
| 2003/0202938 A1 | 10/2003 | Rameshwar |
| 2003/0203483 A1 | 10/2003 | Seshi |
| 2003/0204323 A1 | 10/2003 | Morrisey |
| 2003/0211602 A1 | 11/2003 | Atala |
| 2003/0211603 A1 | 11/2003 | Earp et al. |
| 2003/0216718 A1 | 11/2003 | Hamblin et al. |
| 2003/0219898 A1 | 11/2003 | Sugaya et al. |
| 2003/0223968 A1 | 12/2003 | Yang |
| 2003/0224420 A1 | 12/2003 | Hellerstein et al. |
| 2003/0224510 A1 | 12/2003 | Yamaguchi et al. |
| 2003/0225010 A1 | 12/2003 | Rameshwar |
| 2003/0232432 A1 | 12/2003 | Bhat |

(56) References Cited

U.S. PATENT DOCUMENTS

| | | |
|---|---|---|
| 2003/0232752 A1 | 12/2003 | Freeman et al. |
| 2003/0235909 A1 | 12/2003 | Hariri et al. |
| 2004/0009158 A1 | 1/2004 | Sands et al. |
| 2004/0009589 A1 | 1/2004 | Levenberg et al. |
| 2004/0010231 A1 | 1/2004 | Leonhardt et al. |
| 2004/0014209 A1 | 1/2004 | Lassar et al. |
| 2004/0018174 A1 | 1/2004 | Palasis |
| 2004/0018617 A1 | 1/2004 | Hwang |
| 2004/0023324 A1 | 2/2004 | Sakano et al. |
| 2004/0023370 A1 | 2/2004 | Yu et al. |
| 2004/0033214 A1 | 2/2004 | Young et al. |
| 2004/0033599 A1 | 2/2004 | Rosenberg |
| 2004/0037811 A1 | 2/2004 | Penn et al. |
| 2004/0037815 A1 | 2/2004 | Clarke et al. |
| 2004/0038316 A1 | 2/2004 | Kaiser et al. |
| 2004/0053869 A1 | 3/2004 | Andrews et al. |
| 2004/0062753 A1 | 4/2004 | Rezania et al. |
| 2004/0063205 A1 | 4/2004 | Xu |
| 2004/0067585 A1 | 4/2004 | Wang et al. |
| 2004/0071668 A1 | 4/2004 | Bays et al. |
| 2004/0072259 A1 | 4/2004 | Scadden et al. |
| 2004/0077079 A1 | 4/2004 | Storgaard et al. |
| 2004/0079248 A1 | 4/2004 | Mayer et al. |
| 2004/0087016 A1 | 5/2004 | Keating et al. |
| 2004/0091936 A1 | 5/2004 | West |
| 2004/0096476 A1 | 5/2004 | Uhrich et al. |
| 2004/0097408 A1 | 5/2004 | Leder et al. |
| 2004/0101959 A1 | 5/2004 | Marko et al. |
| 2004/0107453 A1 | 6/2004 | Furcht et al. |
| 2004/0110286 A1 | 6/2004 | Bhatia |
| 2004/0115804 A1 | 6/2004 | Fu et al. |
| 2004/0115806 A1 | 6/2004 | Fu |
| 2004/0120932 A1 | 6/2004 | Zahner |
| 2004/0121461 A1 | 6/2004 | Honmou et al. |
| 2004/0121464 A1 | 6/2004 | Rathjen et al. |
| 2004/0126405 A1 | 7/2004 | Sahatjian et al. |
| 2004/0128077 A1 | 7/2004 | Koebler et al. |
| 2004/0131601 A1 | 7/2004 | Epstein et al. |
| 2004/0132184 A1 | 7/2004 | Dennis et al. |
| 2004/0136967 A1 | 7/2004 | Weiss et al. |
| 2004/0137612 A1 | 7/2004 | Baksh |
| 2004/0137613 A1 | 7/2004 | Vacanti et al. |
| 2004/0143174 A1 | 7/2004 | Brubaker |
| 2004/0143863 A1 | 7/2004 | Li et al. |
| 2004/0151700 A1 | 8/2004 | Harlan et al. |
| 2004/0151701 A1 | 8/2004 | Kim et al. |
| 2004/0151706 A1 | 8/2004 | Shakhov et al. |
| 2004/0151729 A1 | 8/2004 | Michalopoulos et al. |
| 2004/0152190 A1 | 8/2004 | Sumita |
| 2004/0161419 A1 | 8/2004 | Strom et al. |
| 2004/0171533 A1 | 9/2004 | Zehentner et al. |
| 2004/0180347 A1 | 9/2004 | Stanton et al. |
| 2004/0191902 A1 | 9/2004 | Hambor et al. |
| 2004/0197310 A1 | 10/2004 | Sanberg et al. |
| 2004/0197375 A1 | 10/2004 | Rezania et al. |
| 2004/0208786 A1 | 10/2004 | Kevy et al. |
| 2004/0214275 A1 | 10/2004 | Soejima et al. |
| 2004/0219134 A1 | 11/2004 | Naughton et al. |
| 2004/0219136 A1 | 11/2004 | Hariri |
| 2004/0219563 A1 | 11/2004 | West et al. |
| 2004/0224403 A1 | 11/2004 | Bhatia |
| 2004/0229351 A1 | 11/2004 | Rodriguez et al. |
| 2004/0234972 A1 | 11/2004 | Owens et al. |
| 2004/0235158 A1 | 11/2004 | Bartlett et al. |
| 2004/0235160 A1 | 11/2004 | Nishikawa et al. |
| 2004/0235166 A1 | 11/2004 | Prockop et al. |
| 2004/0242469 A1 | 12/2004 | Lee et al. |
| 2004/0258669 A1 | 12/2004 | Dzau et al. |
| 2004/0259242 A1 | 12/2004 | Malinge et al. |
| 2004/0259254 A1 | 12/2004 | Honmou et al. |
| 2004/0260058 A1 | 12/2004 | Scheek et al. |
| 2004/0260318 A1 | 12/2004 | Hunter et al. |
| 2004/0265996 A1 | 12/2004 | Schwarz et al. |
| 2005/0002914 A1 | 1/2005 | Rosen et al. |
| 2005/0003460 A1 | 1/2005 | Nilsson et al. |
| 2005/0003527 A1 | 1/2005 | Lang et al. |
| 2005/0003534 A1 | 1/2005 | Huberman et al. |
| 2005/0008624 A1 | 1/2005 | Peled et al. |
| 2005/0008626 A1 | 1/2005 | Fraser et al. |
| 2005/0009178 A1 | 1/2005 | Yost et al. |
| 2005/0009179 A1 | 1/2005 | Gemmiti et al. |
| 2005/0009181 A1 | 1/2005 | Black et al. |
| 2005/0013804 A1 | 1/2005 | Kato et al. |
| 2005/0014252 A1 | 1/2005 | Chu et al. |
| 2005/0014253 A1 | 1/2005 | Ehmann et al. |
| 2005/0014254 A1 | 1/2005 | Kruse |
| 2005/0014255 A1 | 1/2005 | Tang et al. |
| 2005/0019801 A1 | 1/2005 | Rubin et al. |
| 2005/0019908 A1 | 1/2005 | Hariri |
| 2005/0019910 A1 | 1/2005 | Takagi et al. |
| 2005/0019911 A1 | 1/2005 | Gronthos et al. |
| 2005/0026836 A1 | 2/2005 | Dack et al. |
| 2005/0031587 A1 | 2/2005 | Tsutsui et al. |
| 2005/0031595 A1 | 2/2005 | Peled et al. |
| 2005/0031598 A1 | 2/2005 | Levenberg et al. |
| 2005/0032122 A1 | 2/2005 | Hwang et al. |
| 2005/0032207 A1 | 2/2005 | Wobus et al. |
| 2005/0032209 A1 | 2/2005 | Messina et al. |
| 2005/0032218 A1 | 2/2005 | Gerlach |
| 2005/0036980 A1 | 2/2005 | Chaney et al. |
| 2005/0037488 A1 | 2/2005 | Mitalipova et al. |
| 2005/0037490 A1 | 2/2005 | Rosenberg et al. |
| 2005/0037492 A1 | 2/2005 | Xu et al. |
| 2005/0037493 A1 | 2/2005 | Mandalam et al. |
| 2005/0037949 A1 | 2/2005 | O'Brien et al. |
| 2005/0106119 A1 | 5/2005 | Brandom et al. |
| 2005/0106127 A1 | 5/2005 | Kraus et al. |
| 2005/0112447 A1 | 5/2005 | Fletcher et al. |
| 2005/0112762 A1 | 5/2005 | Hart et al. |
| 2005/0118712 A1 | 6/2005 | Tsai et al. |
| 2005/0130297 A1 | 6/2005 | Sarem et al. |
| 2005/0136093 A1 | 6/2005 | Denk |
| 2005/0137517 A1 | 6/2005 | Blickhan et al. |
| 2005/0142162 A1 | 6/2005 | Hunter et al. |
| 2005/0149157 A1 | 7/2005 | Hunter et al. |
| 2005/0152946 A1 | 7/2005 | Hunter et al. |
| 2005/0158289 A1 | 7/2005 | Simmons et al. |
| 2005/0172340 A1 | 8/2005 | Logvinov et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0180957 A1 | 8/2005 | Scharp et al. |
| 2005/0181502 A1 | 8/2005 | Furcht et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186671 A1 | 8/2005 | Cannon et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2005/0244963 A1 | 11/2005 | Teplyashin |
| 2005/0249731 A1 | 11/2005 | Aslan et al. |
| 2005/0255118 A1 | 11/2005 | Wehner |
| 2005/0261674 A1 | 11/2005 | Nobis et al. |
| 2005/0277577 A1 | 12/2005 | Hunter et al. |
| 2005/0281790 A1 | 12/2005 | Simmons et al. |
| 2005/0282733 A1 | 12/2005 | Prins et al. |
| 2005/0283844 A1 | 12/2005 | Furcht et al. |
| 2006/0002900 A1 | 1/2006 | Binder et al. |
| 2006/0008452 A1 | 1/2006 | Simmons et al. |
| 2006/0019389 A1 | 1/2006 | Yayon et al. |
| 2006/0054941 A1 | 3/2006 | Lu et al. |
| 2006/0083720 A1 | 4/2006 | Fraser et al. |
| 2006/0099198 A1 | 5/2006 | Thomson et al. |
| 2006/0166364 A1 | 7/2006 | Senesac |
| 2006/0172008 A1 | 8/2006 | Yayon et al. |
| 2006/0193840 A1 | 8/2006 | Gronthos et al. |
| 2006/0228798 A1 | 10/2006 | Verfaillie et al. |
| 2006/0239909 A1 | 10/2006 | Anderson et al. |
| 2006/0258586 A1 | 11/2006 | Sheppard et al. |
| 2006/0258933 A1 | 11/2006 | Ellis et al. |
| 2006/0259998 A1 | 11/2006 | Brumbley et al. |
| 2006/0280748 A1 | 12/2006 | Buckheit |

(56) References Cited

U.S. PATENT DOCUMENTS

| | | |
|---|---|---|
| 2006/0286077 A1 | 12/2006 | Gronthos et al. |
| 2007/0005148 A1 | 1/2007 | Barofsky et al. |
| 2007/0011752 A1 | 1/2007 | Paleyanda |
| 2007/0042462 A1 | 2/2007 | Hildinger |
| 2007/0065938 A1 | 3/2007 | Gronthos et al. |
| 2007/0105222 A1 | 5/2007 | Wolfinbarger et al. |
| 2007/0116612 A1 | 5/2007 | Williamson |
| 2007/0117180 A1 | 5/2007 | Morikawa et al. |
| 2007/0122904 A1* | 5/2007 | Nordon ............... C12M 29/10 435/456 |
| 2007/0123996 A1 | 5/2007 | Sugaya et al. |
| 2007/0166834 A1 | 7/2007 | Williamson et al. |
| 2007/0178071 A1 | 8/2007 | Westenfelder |
| 2007/0196421 A1 | 8/2007 | Hunter et al. |
| 2007/0197957 A1 | 8/2007 | Hunter et al. |
| 2007/0198063 A1 | 8/2007 | Hunter et al. |
| 2007/0202485 A1 | 8/2007 | Nees et al. |
| 2007/0203330 A1 | 8/2007 | Kretschmar et al. |
| 2007/0208134 A1 | 9/2007 | Hunter et al. |
| 2007/0258943 A1 | 11/2007 | Penn et al. |
| 2007/0274970 A1 | 11/2007 | Gordon et al. |
| 2007/0275457 A1 | 11/2007 | Granchelli et al. |
| 2007/0295651 A1 | 12/2007 | Martinez et al. |
| 2007/0298015 A1 | 12/2007 | Beer et al. |
| 2008/0003663 A1 | 1/2008 | Bryhan et al. |
| 2008/0009458 A1 | 1/2008 | Dornan et al. |
| 2008/0032398 A1 | 2/2008 | Cannon et al. |
| 2008/0050770 A1 | 2/2008 | Zhang et al. |
| 2008/0063600 A1 | 3/2008 | Aguzzi et al. |
| 2008/0064649 A1 | 3/2008 | Rameshwar |
| 2008/0069807 A1 | 3/2008 | Jy et al. |
| 2008/0095676 A1 | 4/2008 | Andretta |
| 2008/0095690 A1 | 4/2008 | Liu |
| 2008/0103412 A1 | 5/2008 | Chin |
| 2008/0110827 A1 | 5/2008 | Cote et al. |
| 2008/0113426 A1 | 5/2008 | Smith et al. |
| 2008/0113440 A1 | 5/2008 | Gurney et al. |
| 2008/0153077 A1 | 6/2008 | Henry |
| 2008/0160597 A1 | 7/2008 | van der Heiden et al. |
| 2008/0166808 A1 | 7/2008 | Nyberg |
| 2008/0181879 A1 | 7/2008 | Catelas et al. |
| 2008/0190857 A1 | 8/2008 | Beretta et al. |
| 2008/0194017 A1 | 8/2008 | Esser et al. |
| 2008/0206831 A1 | 8/2008 | Coffey et al. |
| 2008/0220524 A1 | 9/2008 | Noll et al. |
| 2008/0220526 A1 | 9/2008 | Ellison et al. |
| 2008/0221443 A1 | 9/2008 | Ritchie et al. |
| 2008/0227189 A1 | 9/2008 | Bader |
| 2008/0268165 A1 | 10/2008 | Fekety et al. |
| 2008/0306095 A1 | 12/2008 | Crawford |
| 2009/0004738 A1 | 1/2009 | Merchav et al. |
| 2009/0011399 A1 | 1/2009 | Fischer |
| 2009/0047289 A1 | 2/2009 | Denhardt et al. |
| 2009/0074728 A1 | 3/2009 | Gronthos et al. |
| 2009/0075881 A1 | 3/2009 | Catelas et al. |
| 2009/0076481 A1 | 3/2009 | Stegmann et al. |
| 2009/0081770 A1 | 3/2009 | Srienc et al. |
| 2009/0081797 A1 | 3/2009 | Fadeev et al. |
| 2009/0092608 A1 | 4/2009 | Ni et al. |
| 2009/0098103 A1 | 4/2009 | Madison et al. |
| 2009/0098645 A1 | 4/2009 | Fang et al. |
| 2009/0100944 A1 | 4/2009 | Newby |
| 2009/0104163 A1 | 4/2009 | Deans et al. |
| 2009/0104692 A1 | 4/2009 | Bartfeld et al. |
| 2009/0104699 A1 | 4/2009 | Newby et al. |
| 2009/0118161 A1 | 5/2009 | Cruz |
| 2009/0181087 A1 | 7/2009 | Kraus et al. |
| 2009/0183581 A1 | 7/2009 | Wilkinson et al. |
| 2009/0191627 A1 | 7/2009 | Fadeev et al. |
| 2009/0191632 A1 | 7/2009 | Fadeev et al. |
| 2009/0191634 A1 | 7/2009 | Martin et al. |
| 2009/0203065 A1 | 8/2009 | Gehman et al. |
| 2009/0203129 A1 | 8/2009 | Furcht et al. |
| 2009/0203130 A1 | 8/2009 | Furcht et al. |
| 2009/0214382 A1 | 8/2009 | Burgess et al. |
| 2009/0214481 A1 | 8/2009 | Muhs et al. |
| 2009/0214652 A1 | 8/2009 | Hunter et al. |
| 2009/0215022 A1 | 8/2009 | Page et al. |
| 2009/0227024 A1 | 9/2009 | Baker et al. |
| 2009/0227027 A1 | 9/2009 | Baker et al. |
| 2009/0233334 A1 | 9/2009 | Hildinger et al. |
| 2009/0233353 A1 | 9/2009 | Furcht et al. |
| 2009/0233354 A1 | 9/2009 | Furcht et al. |
| 2009/0258379 A1 | 10/2009 | Klein et al. |
| 2009/0269841 A1 | 10/2009 | Wojciechowski et al. |
| 2009/0270725 A1 | 10/2009 | Leimbach et al. |
| 2009/0280153 A1 | 11/2009 | Hunter et al. |
| 2009/0280565 A1 | 11/2009 | Jolicoeur et al. |
| 2009/0291890 A1 | 11/2009 | Madison et al. |
| 2010/0009409 A1 | 1/2010 | Hubbell et al. |
| 2010/0021954 A1 | 1/2010 | Deshayes et al. |
| 2010/0021990 A1 | 1/2010 | Edwards et al. |
| 2010/0028311 A1 | 2/2010 | Motlagh et al. |
| 2010/0075410 A1 | 3/2010 | Desai et al. |
| 2010/0086481 A1 | 4/2010 | Baird et al. |
| 2010/0092536 A1 | 4/2010 | Hunter et al. |
| 2010/0093607 A1 | 4/2010 | Dickneite |
| 2010/0111910 A1 | 5/2010 | Rakoczy |
| 2010/0129376 A1 | 5/2010 | Denhardt et al. |
| 2010/0129912 A1 | 5/2010 | Su et al. |
| 2010/0136091 A1 | 6/2010 | Moghe et al. |
| 2010/0144634 A1 | 6/2010 | Zheng et al. |
| 2010/0183561 A1 | 7/2010 | Sakthivel et al. |
| 2010/0183585 A1 | 7/2010 | Van Zant et al. |
| 2010/0203020 A1 | 8/2010 | Ghosh |
| 2010/0230203 A1 | 9/2010 | Karayianni |
| 2010/0248366 A1 | 9/2010 | Fadeev et al. |
| 2010/0278933 A1 | 11/2010 | Sayeski et al. |
| 2010/0285453 A1 | 11/2010 | Goodrich |
| 2010/0285590 A1 | 11/2010 | Verfaillie et al. |
| 2010/0291180 A1 | 11/2010 | Uhrich |
| 2010/0291181 A1 | 11/2010 | Uhrich et al. |
| 2010/0297234 A1 | 11/2010 | Sugino et al. |
| 2010/0304427 A1 | 12/2010 | Faris et al. |
| 2010/0304482 A1 | 12/2010 | Deshayes et al. |
| 2010/0310524 A1 | 12/2010 | Bechor et al. |
| 2010/0316446 A1 | 12/2010 | Runyon |
| 2011/0085746 A1 | 4/2011 | Wong et al. |
| 2011/0111498 A1 | 5/2011 | Oh et al. |
| 2011/0129447 A1 | 6/2011 | Meretzki et al. |
| 2011/0129486 A1 | 6/2011 | Meiron |
| 2011/0143433 A1 | 6/2011 | Oh et al. |
| 2011/0159584 A1 | 6/2011 | Gibbons et al. |
| 2011/0171182 A1 | 7/2011 | Abelman |
| 2011/0171659 A1 | 7/2011 | Furcht et al. |
| 2011/0177595 A1 | 7/2011 | Furcht et al. |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0028352 A1 | 2/2012 | Oh et al. |
| 2012/0051976 A1 | 3/2012 | Lu et al. |
| 2012/0058554 A1 | 3/2012 | Deshayes et al. |
| 2012/0064047 A1 | 3/2012 | Verfaillie et al. |
| 2012/0064583 A1 | 3/2012 | Edwards et al. |
| 2012/0118919 A1 | 5/2012 | Cianciolo |
| 2012/0122220 A1 | 5/2012 | Merchav et al. |
| 2012/0135043 A1 | 5/2012 | Maziarz et al. |
| 2012/0145580 A1 | 6/2012 | Paruit et al. |
| 2012/0156779 A1 | 6/2012 | Anneren et al. |
| 2012/0178885 A1 | 7/2012 | Kohn et al. |
| 2012/0189713 A1 | 7/2012 | Kohn et al. |
| 2012/0208039 A1 | 8/2012 | Barbaroux et al. |
| 2012/0219531 A1 | 8/2012 | Oh et al. |
| 2012/0219737 A1 | 8/2012 | Sugino et al. |
| 2012/0226013 A1 | 9/2012 | Kohn et al. |
| 2012/0231519 A1 | 9/2012 | Bushman et al. |
| 2012/0237557 A1 | 9/2012 | Lewitus et al. |
| 2012/0295352 A1 | 11/2012 | Antwiler |
| 2012/0308531 A1 | 12/2012 | Pinxteren et al. |
| 2012/0315696 A1 | 12/2012 | Luitjens et al. |
| 2013/0004465 A1 | 1/2013 | Aberman |
| 2013/0039892 A1 | 2/2013 | Aberman |
| 2013/0058907 A1 | 3/2013 | Wojciechowski et al. |

(56) References Cited

U.S. PATENT DOCUMENTS

| | | |
|---|---|---|
| 2013/0059383 A1 | 3/2013 | Dijkhuizen Borgart et al. |
| 2013/0101561 A1 | 4/2013 | Sabaawy |
| 2013/0143313 A1 | 6/2013 | Niazi |
| 2013/0157353 A1 | 6/2013 | Dijkhuizen Borgart et al. |
| 2013/0259843 A1 | 10/2013 | Duda et al. |
| 2013/0319575 A1 | 12/2013 | Mendyk |
| 2013/0323213 A1 | 12/2013 | Meiron et al. |
| 2013/0337558 A1 | 12/2013 | Meiron et al. |
| 2014/0004553 A1 | 1/2014 | Parker et al. |
| 2014/0017209 A1 | 1/2014 | Aberman et al. |
| 2014/0030805 A1 | 1/2014 | Kasuto et al. |
| 2014/0051162 A1 | 2/2014 | Nankervis |
| 2014/0051167 A1 | 2/2014 | Nankervis et al. |
| 2014/0112893 A1 | 4/2014 | Tom et al. |
| 2014/0186937 A1 | 7/2014 | Smith et al. |
| 2014/0193895 A1 | 7/2014 | Smith et al. |
| 2014/0193911 A1 | 7/2014 | Newby et al. |
| 2014/0242039 A1 | 8/2014 | Meiron et al. |
| 2014/0248244 A1 | 9/2014 | Danilkovitch et al. |
| 2014/0315300 A1 | 10/2014 | Oh et al. |
| 2014/0342448 A1 | 11/2014 | Nagels |
| 2015/0004693 A1 | 1/2015 | Danilkovitch et al. |
| 2015/0104431 A1 | 4/2015 | Pittenger et al. |
| 2015/0111252 A1 | 4/2015 | Hirschel et al. |
| 2015/0125138 A1 | 5/2015 | Karnieli et al. |
| 2015/0175950 A1 | 6/2015 | Hirschel et al. |
| 2015/0225685 A1 | 8/2015 | Hirschel et al. |
| 2015/0247122 A1 | 9/2015 | Tom et al. |
| 2015/0259749 A1 | 9/2015 | Santos et al. |
| 2016/0362650 A1 | 12/2016 | Wojciechowski et al. |
| 2016/0362652 A1 | 12/2016 | Page et al. |
| 2018/0010082 A1 | 1/2018 | Jaques et al. |
| 2018/0030398 A1 | 2/2018 | Castillo |
| 2018/0155668 A1 | 6/2018 | Hirschel et al. |
| 2019/0194628 A1 | 6/2019 | Rao et al. |

FOREIGN PATENT DOCUMENTS

| | | |
|---|---|---|
| DE | 10244859 A1 | 4/2004 |
| DE | 10327988 A1 | 7/2004 |
| DE | 102012200939 A1 | 7/2013 |
| EP | 750938 A1 | 1/1997 |
| EP | 906415 A1 | 4/1999 |
| EP | 959980 A1 | 12/1999 |
| EP | 1007631 A1 | 6/2000 |
| EP | 1028737 A1 | 8/2000 |
| EP | 1028991 A1 | 8/2000 |
| EP | 1066052 A2 | 1/2001 |
| EP | 1066060 A2 | 1/2001 |
| EP | 1084230 A2 | 3/2001 |
| EP | 1147176 A1 | 10/2001 |
| EP | 1220611 A1 | 7/2002 |
| EP | 1223956 A1 | 7/2002 |
| EP | 1325953 A1 | 7/2003 |
| EP | 1437404 A1 | 7/2004 |
| EP | 1437406 A2 | 7/2004 |
| EP | 1447443 A1 | 8/2004 |
| EP | 1452594 A1 | 9/2004 |
| EP | 1062321 B1 | 12/2004 |
| EP | 1484080 A1 | 12/2004 |
| EP | 1498478 A1 | 1/2005 |
| EP | 1036057 B1 | 10/2005 |
| EP | 1605044 A2 | 12/2005 |
| EP | 1756262 A1 | 2/2007 |
| EP | 1771737 A1 | 4/2007 |
| EP | 1882030 A1 | 1/2008 |
| EP | 1908490 A1 | 4/2008 |
| EP | 1971679 A2 | 9/2008 |
| EP | 1991668 A2 | 11/2008 |
| EP | 2027247 A2 | 2/2009 |
| EP | 2200622 A1 | 6/2010 |
| EP | 2208782 A2 | 7/2010 |
| EP | 2264145 A1 | 12/2010 |
| EP | 2303293 A1 | 4/2011 |
| EP | 2311938 A1 | 4/2011 |
| EP | 2331957 A1 | 6/2011 |
| EP | 2334310 A2 | 6/2011 |
| EP | 2334783 A2 | 6/2011 |
| EP | 2361968 A1 | 8/2011 |
| EP | 2366775 A1 | 9/2011 |
| EP | 2465922 A2 | 6/2012 |
| EP | 2548951 A1 | 1/2013 |
| EP | 2561066 A1 | 2/2013 |
| EP | 2575831 A1 | 4/2013 |
| EP | 2591789 A2 | 5/2013 |
| EP | 2624845 A2 | 8/2013 |
| EP | 2626417 A1 | 8/2013 |
| EP | 2641606 A1 | 9/2013 |
| EP | 2689008 A1 | 1/2014 |
| EP | 2694639 A1 | 2/2014 |
| EP | 2697362 A2 | 2/2014 |
| EP | 2739720 A1 | 6/2014 |
| EP | 2807246 A1 | 12/2014 |
| GB | 1414671 A | 11/1975 |
| GB | 2297980 A | 12/1999 |
| GB | 2360789 A | 10/2001 |
| HU | 3285 U | 5/2007 |
| JP | 2003/052360 A | 2/2003 |
| JP | 5548207 B2 | 7/2014 |
| MY | 115206 A | 4/2003 |
| WO | WO-9013306 A2 | 11/1990 |
| WO | WO-9105238 A1 | 4/1991 |
| WO | WO-9106641 A1 | 5/1991 |
| WO | WO-9109194 A1 | 6/1991 |
| WO | WO-94/25571 A1 | 11/1994 |
| WO | WO-96/29395 A1 | 9/1996 |
| WO | WO-96/39035 A1 | 12/1996 |
| WO | WO-97/05826 A1 | 2/1997 |
| WO | WO-97/29792 A1 | 8/1997 |
| WO | WO-97/39104 A1 | 10/1997 |
| WO | WO-1997-040137 A1 | 10/1997 |
| WO | WO-98/31403 A1 | 7/1998 |
| WO | WO-98/51317 A1 | 11/1998 |
| WO | WO-98/51785 A1 | 11/1998 |
| WO | WO-99/05180 A1 | 2/1999 |
| WO | WO-99/24391 A1 | 5/1999 |
| WO | WO-99/24490 A1 | 5/1999 |
| WO | WO-99/27167 A1 | 6/1999 |
| WO | WO-99/49015 A2 | 9/1999 |
| WO | WO-00/06704 A2 | 2/2000 |
| WO | WO-0009018 A1 | 2/2000 |
| WO | WO-00/16420 A1 | 3/2000 |
| WO | WO-00/17326 A1 | 3/2000 |
| WO | WO-00/29002 A2 | 5/2000 |
| WO | WO-0032225 A1 | 6/2000 |
| WO | WO-00/44058 A2 | 7/2000 |
| WO | WO-0054651 A2 | 9/2000 |
| WO | WO-0056405 A2 | 9/2000 |
| WO | WO-00/59933 A2 | 10/2000 |
| WO | WO-00/69449 A2 | 11/2000 |
| WO | WO-00/75196 A1 | 12/2000 |
| WO | WO-00/77236 A2 | 12/2000 |
| WO | WO-2001/000783 A2 | 1/2001 |
| WO | WO-2001/011011 A2 | 2/2001 |
| WO | WO-2001/018174 A2 | 3/2001 |
| WO | WO-2001/021766 A2 | 3/2001 |
| WO | WO-2001/025402 A1 | 4/2001 |
| WO | WO-2001/029189 A2 | 4/2001 |
| WO | WO-0122810 A2 | 4/2001 |
| WO | WO-2001/034167 A1 | 5/2001 |
| WO | WO-2001/049851 A1 | 7/2001 |
| WO | WO-2001/054706 A2 | 8/2001 |
| WO | WO-2001-094541 A2 | 12/2001 |
| WO | WO-2002/042422 A2 | 5/2002 |
| WO | WO-2002/057430 A2 | 7/2002 |
| WO | WO-2002/092794 A2 | 11/2002 |
| WO | WO-2002/101385 A2 | 12/2002 |
| WO | WO-2003/010303 A1 | 2/2003 |
| WO | WO-2003/014313 A2 | 2/2003 |
| WO | WO-2003/016916 A1 | 2/2003 |
| WO | WO-2003/023018 A2 | 3/2003 |
| WO | WO-2003/023019 A1 | 3/2003 |
| WO | WO-2003/025167 A2 | 3/2003 |
| WO | WO-2003/029402 A2 | 4/2003 |

(56) References Cited

FOREIGN PATENT DOCUMENTS

| | | |
|---|---|---|
| WO | WO-2003/040336 A2 | 5/2003 |
| WO | WO-2003/042405 A2 | 5/2003 |
| WO | WO-2003/046161 A2 | 6/2003 |
| WO | WO-2003/055989 A2 | 7/2003 |
| WO | WO-2003/061685 A1 | 7/2003 |
| WO | WO-2003/061686 A1 | 7/2003 |
| WO | WO-2003/068961 A2 | 8/2003 |
| WO | WO-2003/072064 A2 | 9/2003 |
| WO | WO-2003/078609 A1 | 9/2003 |
| WO | WO-2003/078967 A2 | 9/2003 |
| WO | WO-2003/080816 A2 | 10/2003 |
| WO | WO-2003/082145 A2 | 10/2003 |
| WO | WO-2003/085099 A2 | 10/2003 |
| WO | WO-2003/089631 A1 | 10/2003 |
| WO | WO-2003/091398 A2 | 11/2003 |
| WO | WO-2003/095631 A1 | 11/2003 |
| WO | WO-2004/001697 A1 | 12/2003 |
| WO | WO-2004/012226 A2 | 2/2004 |
| WO | WO-2004/016779 A1 | 2/2004 |
| WO | WO-2004/018526 A1 | 3/2004 |
| WO | WO-2004/018655 A2 | 3/2004 |
| WO | WO-2004/026115 A2 | 4/2004 |
| WO | WO-2004/029231 A1 | 4/2004 |
| WO | WO-2004/042023 A2 | 5/2004 |
| WO | WO-2004/042033 A2 | 5/2004 |
| WO | WO-2004/042040 A1 | 5/2004 |
| WO | WO-2004/044127 A2 | 5/2004 |
| WO | WO-2004/044158 A2 | 5/2004 |
| WO | WO-2004/046304 A1 | 6/2004 |
| WO | WO-2004/050826 A2 | 6/2004 |
| WO | WO-2004/053096 A2 | 6/2004 |
| WO | WO-2004/055155 A2 | 7/2004 |
| WO | WO-2004/056186 A1 | 7/2004 |
| WO | WO-2004/065616 A2 | 8/2004 |
| WO | WO-2004/069172 A2 | 8/2004 |
| WO | WO-2004/070013 A2 | 8/2004 |
| WO | WO-2004/072264 A2 | 8/2004 |
| WO | WO-2004/073633 A2 | 9/2004 |
| WO | WO-2004/074464 A1 | 9/2004 |
| WO | WO-2004/076642 A2 | 9/2004 |
| WO | WO-2004/076653 A1 | 9/2004 |
| WO | WO-2004/087870 A2 | 10/2004 |
| WO | WO-2004/094588 A2 | 11/2004 |
| WO | WO-2004/096975 A2 | 11/2004 |
| WO | WO-2004/104166 A2 | 12/2004 |
| WO | WO-2004/106499 A1 | 12/2004 |
| WO | WO-2004/113513 A2 | 12/2004 |
| WO | WO-2005/001033 A2 | 1/2005 |
| WO | WO-2005/001081 A1 | 1/2005 |
| WO | WO-2005/003320 A2 | 1/2005 |
| WO | WO-2005/007799 A2 | 1/2005 |
| WO | WO-2005/010172 A2 | 2/2005 |
| WO | WO-2005/011524 A1 | 2/2005 |
| WO | WO-2005/012480 A2 | 2/2005 |
| WO | WO-2005/012510 A1 | 2/2005 |
| WO | WO-2005/012512 A1 | 2/2005 |
| WO | WO-05014775 A2 | 2/2005 |
| WO | WO-2005/028433 A2 | 3/2005 |
| WO | WO-05044972 A2 | 5/2005 |
| WO | WO-2005/056747 A2 | 6/2005 |
| WO | WO-05051316 A2 | 6/2005 |
| WO | WO-2005/063303 A1 | 7/2005 |
| WO | WO-2005/075636 A1 | 8/2005 |
| WO | WO-2005/107760 A1 | 11/2005 |
| WO | WO-2006/009291 A1 | 1/2006 |
| WO | WO-2006/032075 A1 | 3/2006 |
| WO | WO-2006/032092 A1 | 3/2006 |
| WO | 2006-047841 A2 | 5/2006 |
| WO | WO-2006-047841 A2 | 5/2006 |
| WO | WO-2006/108229 A1 | 10/2006 |
| WO | WO-2006/113881 A2 | 10/2006 |
| WO | WO-2006/121445 A2 | 11/2006 |
| WO | WO-06124021 A1 | 11/2006 |
| WO | WO-06129312 A2 | 12/2006 |
| WO | WO-2007/115367 A1 | 10/2007 |
| WO | WO-2007/115368 A1 | 10/2007 |
| WO | WO-2008/006168 A1 | 1/2008 |
| WO | WO-2008/011664 A1 | 1/2008 |
| WO | WO-2008/017128 A1 | 2/2008 |
| WO | WO-2008/028241 A1 | 3/2008 |
| WO | WO-08040812 A1 | 4/2008 |
| WO | WO-2008/116261 A1 | 10/2008 |
| WO | WO-2008/149129 A1 | 12/2008 |
| WO | WO-2009/026635 A1 | 3/2009 |
| WO | WO-09058146 A1 | 5/2009 |
| WO | WO-09080054 A1 | 7/2009 |
| WO | WO-09081408 A2 | 7/2009 |
| WO | WO-2009/140452 A2 | 11/2009 |
| WO | WO-09132457 A1 | 11/2009 |
| WO | WO-2009/144720 A2 | 12/2009 |
| WO | WO-10005527 A1 | 1/2010 |
| WO | WO-2010/019886 A1 | 2/2010 |
| WO | WO-10014253 A2 | 2/2010 |
| WO | WO-10019997 A1 | 2/2010 |
| WO | WO-2010/026573 A1 | 3/2010 |
| WO | WO-2010/026574 A2 | 3/2010 |
| WO | WO-2010/026575 A2 | 3/2010 |
| WO | WO-2010/036760 A1 | 4/2010 |
| WO | WO-2010/059487 A1 | 5/2010 |
| WO | WO-10061377 A2 | 6/2010 |
| WO | WO-10068710 A2 | 6/2010 |
| WO | WO-10071826 A2 | 6/2010 |
| WO | WO-10083385 A2 | 7/2010 |
| WO | WO-10111255 A1 | 9/2010 |
| WO | WO-10119036 A1 | 10/2010 |
| WO | WO-10123594 A2 | 10/2010 |
| WO | WO-2011/025445 A1 | 3/2011 |
| WO | WO-2011/132087 A1 | 10/2011 |
| WO | WO-2011/147967 A1 | 12/2011 |
| WO | WO-2012/072924 A1 | 6/2012 |
| WO | WO-2012/127320 A1 | 9/2012 |
| WO | WO-2012/138968 A1 | 10/2012 |
| WO | WO-2012/140519 A2 | 10/2012 |
| WO | WO-2012/171026 A2 | 12/2012 |
| WO | WO-2012/171030 A2 | 12/2012 |
| WO | WO-2013/110651 A1 | 8/2013 |
| WO | WO-2014/037862 A1 | 3/2014 |
| WO | WO-2014/037863 A1 | 3/2014 |
| WO | WO-2014/068508 A2 | 5/2014 |
| WO | WO-2014/128306 A1 | 8/2014 |
| WO | WO-2014/128634 A1 | 8/2014 |
| WO | WO-2014/131846 A1 | 9/2014 |
| WO | WO-2014/141111 A1 | 9/2014 |
| WO | WO-2015/004609 A2 | 1/2015 |
| WO | WO-2015/118148 A1 | 8/2015 |
| WO | WO-2015/118149 A1 | 8/2015 |
| WO | WO-2015/131143 A1 | 9/2015 |
| WO | WO-2017/072201 A2 | 5/2017 |
| WO | 2017-205667 A1 | 11/2017 |
| WO | WO-2017-205667 A1 | 11/2017 |

OTHER PUBLICATIONS

Frank, Nathan D. Et Al., "Evaluation of Reagents Used to Coat the Hollow-Fiber Bioreactor Membrane of the Quantum Cell Expansion System for the Culture of Human Mesenchymal Stem Cells", Materials Science and Engineering C, Elsevier Science S.A., Ch, vol. 96, Oct. 26, 2018, pp. 77-85.

Abumiya, et al at National Cardiovascular Center Research Institute in Japan, suggest that subjecting human umbilical vein endothelial cells (HUVECs) to laminar shear stress for a period of 8 hours increased the relative expression of VEGFR-2 mRNA (Ateriosclerosis, Thrombosis, and Vascular Biology, 2002).

Afzali B, Edozie FC, Fazekasova H, Scotta C, Mitchell PJ, Canavan JB, Kordasti SY, Chana PS, Ellis R, Lord GM, John S, Hilton R, Lechler RI, Lombardi G. Comparison of regulatory T cells in hemodialysis patients and healthy controls: implications for cell therapy in transplantation. Clin J Am Soc Nephrol. 2013;8(8):1396-405.

Akram, Khondoker M., et al. "Mesenchymal stem cells promote alveolar epithelial cell wound repair in vitro through distinct migra-

(56) References Cited

OTHER PUBLICATIONS tory and paracrine mechanisms." Respiratory research 14.1 (2013): 1-16.
Alberts B, Johnson A, Lewis J, et al. Molecular Biology of the Cell. 4th edition. New York: Garland Science; 2002. Fibroblasts and Their Transformations: The Connective-Tissue Cell Family. Available from: https://www.ncbi.nlm.nih.gov/books/NBK26889.
Alenazi, Noof A., et al. "Modified polyether-sulfone membrane: A mini review." Designed monomers and polymers 20.1 (2017): 532-546.
Almeida L, Lochner M, Berod L, Sparwasser T. Metabolic pathways in T cell activation and lineage differentiation. Semin Immunol. 2016;28(5):514-524.
Amy Putnam, Todd M. Brusko, Michael R. Lee, Weihong Liu, Gregory L. Szot, Taumoha Ghosh, Mark A. Atkinson, and Jeffrey A. Bluestone. Expansion of human regulatory T-Cells from patients with Type 1 Diabetes. Diabetes, 58: 652-662, 2009.
Anamelechi, Charles C., et al. "Streptavidin binding and endothelial cell adhesion to biotinylated fibronectin." *Langmuir* 23.25 (2007): 12583-12588.
Anurathapan et al., "Engineered T cells for cancer treatment," Cytotherapy, vol. 16, pp. 713-733, 2014.
Aronowski J, Samways E, Strong R, Rhoades HM, Grotta JC. An alternative method for the quantitation of neuronal damage after experimental middle cerebral artery occlusion in rats: Analysis of behavioral deficit. Journal of cerebral blood flow and metabolism : official journal of the International Society of Cerebral Blood Flow and Metabolism. 1996;16:705-713.
Arrigoni, Chiara, et al. "Rotating versus perfusion bioreactor for the culture of engineered vascular constructs based on hyaluronic acid." Biotechnology and bioengineering 100.5 (2008): 988-997.
Azar, Toni, Jody Sharp, and David Lawson. "Heart rates of male and female Sprague-Dawley and spontaneously hypertensive rats housed singly or in groups." Journal of the American Association for Laboratory Animal Science 50.2 (2011): 175-184.
Baecher-Allan, Clare, et al. "CD4+ CD25high regulatory cells in human peripheral blood." The Journal of Immunology 167.3 (2001): 1245-1253.
Bai, Tao, et al. "Expansion of primitive human hematopoietic stem cells by culture in a zwitterionic hydrogel." *Nature medicine* 25.10 (2019): 1566-1575.
Bai/Delaney (Nohla Therapeutics) showed that expanding Cord Blood-derived CD34+CD38-CD45RA-HSPCs in a biodegradable zwitterionic hydrogel with a rNotch ligand cocktail for 24 days mitigated HSPC differentiation and promoted self-renewal of lymphoid and myeloid cell phenotypes in an NSG mouse model (Nature Medicine, 2019).
Ballas CB, Zielske SP, Gerson SL (2002) Adult bone marrow stem cells for cell and gene therapies: implications for greater use. J Cell Biochem Suppl 38: 20-28.
Ballke C, Gran E, Baekkevold ES, Jahnsen FL. Characterization of Regulatory T-Cell Markers in CD4+ T Cells of the Upper Airway Mucosa. PLoS One. 2016;11(2):e0148826.
Baraniak PR, McDevitt TC (2010) Stem cell paracrine actions and tissue regeneration. Regen Med 5(1): 121-143.
Barckhausen C, Rice B, Baila S, et al. (2016) GMP-Compliant Expansion of Clinical-Grade Human Mesenchymal Stromal/Stem Cells Using a Closed Hollow Fiber Bioreactor. Methods Mol Biol 1416: 389-412.
Barker et al. "CD34+ Cell Content of 126 341 Cord Blood Units in the US Inventory: Implications for Transplantation and Banking," blood Advances, vol. 3, No. 8, pp. 1267-1271, Apr. 23, 2019.
Barker, Juliet N., et al. "CD34+ cell content of 126 341 cord blood units in the US inventory: implications for transplantation and banking." *Blood advances* 3.8 (2019): 1267-1271.
Bazarian JJ, Cernak I, Noble-Haeusslein L, Potolicchio S, Temkin N. Long-term neurologic outcomes after traumatic brain injury. The Journal of head trauma rehabilitation. 2009;24:439-451.
Bending D, Pesenacker AM, Ursu S, Wu Q, Lom H, Thirugnanabalan B, Wedderburn LR. Hypomethylation at the regulatory T cell-specific demethylated region in CD25hi T cells is decoupled from FOXP3 expression at the inflamed site in childhood arthritis. J Immunol. 2014;193(6):2699-708.
Berendse M, Grounds MD, Lloyd CM (2003) Myoblast structure affects subsequent skeletal myotube morphology and sarcomere assembly. Exp Cell Res 291(2): 435-450.
Bernard, A., Payton, Mar. 1995. "Fermentation and Growth of *Escherichia coli* for Optimal Protein Production", John Wiley & Sons. Current Protocols in Protein Science (1995) 5.3.1-5.3.18.
Berney SM, Schaan T, Wolf RE, van der Heyde H, Atkinson TP. CD2 (OKT11) augments CD3-mediated intracellular signaling events in human T lymphocytes. J Investig Med. 2000;48(2):102-9.
Bioheart Clinical Trial Clinica 1302 Apr. 18, 2008.
Biomolecular and Cellular Interactions with the Hollow Fiber Membrane Currently Used in the Quantum® Cell Expansion System. 12th NJ Symposium on Biomaterials Science, Oct. 6- 7, 2014, New Brunswick, NJ.
Blache C, Chauvin JM, Marie-Cardine A, Contentin N, Pommier P, Dedreux I, Francois S, Jacquot S, Bastit D, Boyer O. Reduced frequency of regulatory T cells in peripheral blood stem cell compared to bone marrow transplantations. Biol Blood Marrow Transplant. 2010;16(3):430-4.
Bluestone et al. Type 1 diabetes immunotherapy using polyclonal regulatory T cells. Science Translational Medicine 7(315):1-34, 2015.
Bluestone JA, Tang Q. Treg cells-the next frontier of cell therapy. Science. 2018;362(6411):154-155.
Bluestone, Jeffrey A., et al. "Type 1 diabetes immunotherapy using polyclonal regulatory T cells." *Science translational medicine* 7.315 (2015): 315ra189-315ra189.
Blum S, Moore AN, Adams F, Dash PK. A mitogen-activated protein kinase cascade in the ca1/ca2 subfield of the dorsal hippocampus is essential for long-term spatial memory. The Journal of neuroscience : the official journal of the Society for Neuroscience. 1999;19:3535-3544.
Boitano, Anthony E., et al. "Aryl hydrocarbon receptor antagonists promote the expansion of human hematopoietic stem cells." Science 329.5997 (2010): 1345-1348.
Bojun Li et al. Heparin-induced conformation changes of fibronectin within the extracellular matrix promote hMSC osteogenic differentiation. Biomaterials Science 3: 73-84, 2015.
Boquest AC, Shahdadfar A, Brinchmann JE, Collas P. Isolation of Stromal Stem Cells from Human Adipose Tissue. Methods Mol Biol. 2006;325:35-46. doi: 10.1385/1-59745-005-7:35. PMID: 16761717.
Borden, M. and Longo, M., "Dissolution Behavior of Lipid Monolayer-Coated, Air-Filled Microbubbles: Effect of Lipid Hydrophobic Chain Length," Langmuir, vol. 18, pp. 9225-9233, 2002.
Bourke, Sharon L., and Joachim Kohn. "Polymers derived from the amino acid L-tyrosine: polycarbonates, polyarylates and copolymers with poly (ethylene glycol)." Advanced drug delivery reviews 55.4 (2003): 447-466.
Brand, K. and Hermfisse, U., "Aerobic Glycolysis by Proliferating Cells: a Protective Strategy against Reactive Oxygen Species," The FASEB Journal, vol. 11, pp. 388-395, Apr. 1997.
Brentjens et al., "CD19-Targeted T Cells Rapidly Induce Molecular Remission in Adults with Chemotherapy-Refractory Acute Lympohblastic Leukemia," Science Translational Medicine, vol. 5, Issue 177, pp. 1-9, Mar. 20, 2013.
Brentjens et al., "Safety and Persistance of Adoptively Transferred Autologous CD19-Target T Cells in Patients with Relapsed or Chemotherapy Refractory B-Cell Leukemias," Blood, vol. 118, No. 18, pp. 4817-4828, Nov. 3, 2011.
Brunstein C, Miller J, Cao Q, McKenna D, Hippen K, Curtsinger J, DeFor T, Levine B, June C, Rubinstein P, McGlave P, Blazar B, Wagner J. Infusion of ex vivo expanded T regulatory cells in adults transplanted with umbilical cord blood: safety profile and detection kinetics. Blood 2011; 117(3):1061-1070.
C. H. Weaver, et al. An Analysis of Engraftment Kinetics as a function of the CD34 Content of the Peripheral Blood Progenitor Cell Collections in 692 Patients After the Administration of Myeloblative Chemotherapy. Blood 86(10): 3691-3969, 1995.

(56) References Cited

OTHER PUBLICATIONS

Cano, Àngels, Cristina Minguillón, and Cristina Palet. "Immobilization of endo-1, 4-β-xylanase on polysulfone acrylate membranes: Synthesis and characterization." Journal of membrane science 280. 1-2 (2006): 383-388.

Carswell, K. and Papoutsakis, E. "Culture of Human T Cells in Stirred Bioreactors for Cellular Immunotherapy Applications: Shear, Proliferation, and the IL-2 Receptor," Biotechnology and Bioengineering, vol. 68, No. 3, pp. 329-338, May 5, 2000.

Celeste Nelson et al., Emergent patterns of growth controlled by multicellular form and mechanics, (in Christopher Chen's Lab demonstrated, in separate experiments, that curved surfaces with a radius of curvature (200 ?m) that is greater than the cell diameter and surfaces that have undulating special patterning (depressions) increase the patterned growth of ECs [PNAS 102(33): 11594-11599, 2005].

Chapman NM, Chi H. mTOR signaling, Tregs and immune modulation. Immunotherapy. 2014;6(12):1295-311.

Chaudhry A, Samstein RM, Treuting P, Liang Y, Pils MC, Heinrich JM, Jack RS, Wunderlich FT, Bruning JC, Muller W, Rudensky AY. Interleukin-10 signaling in regulatory T cells is required for suppression of Th17 cell-mediated inflammation. Immunity. 2011;34(4):566-78.

Chen, C. and Broden, M., "The Role of Poly(theylene glycol) Brush Architecture in Complement Activation on Targeted Microbubble Surfaces," Biomaterials, vol. 32, No. 27, pp. 6579-6587, Jun. 17, 2011.

Choi W, Kwon SJ, Jin HJ, et al. (2017) Optimization of culture conditions for rapid clinical-scale expansion of human umbilical cord blood-derived mesenchymal stem cells. Clin Transl Med 6(1): 38.

Chullikana A, Majumdar AS, Gottipamula S, et al. (2015) Randomized, double-blind, phase I/II study of intravenous allogeneic mesenchymal stromal cells in acute myocardial infarction. Cytotherapy 17(3): 250-261.

Claudio G. Brunstein, Jeffrey S. Miller, Qing Cao, Daivd H. McKenna, Keli L. Hippen, Julie Curtsinger, Todd Defor, Bruce L. Levine, Carl H. June, Pablo Rubinstein, Philip B. McGlave, Bruce R. Blazar, and John E. Wagner. Infusion of ex vivo expanded T regulatory cells in adults transplanted with umbilical cord blood: safety profile and detection kinetics. Blood, 117(3): 1061-1070, 2010.

Coeshott C, Vang B, Jones M, Nankervis B. Large-scale expansion and characterization of CD3(+) T-cells in the Quantum((R)) Cell Expansion System. J Transl Med. 2019;17(1):258.

Coombes JL, Robinson NJ, Maloy KJ, Uhlig HH, Powrie F. Regulatory T cells and intestinal homeostasis. Immunol Rev. 2005;204:184-94.

Coquillard C. mTOR Signaling in Regulatory T cell Differentiation and Expansion. SOJ Immunology. 2015;3(1):1-10.

Creed JA, DiLeonardi AM, Fox DP, Tessler AR, Raghupathi R. Concussive brain trauma in the mouse results in acute cognitive deficits and sustained impairment of axonal function. Journal of neurotrauma. 2011;28:547-563.

Cuchiara, Maude L. et al., "Covalent Immobilization of Stem Cell Factor and Stromal Derived Factor 1[Alpha] for in Vitro Culture of Hematopoietic Progenitor Cells", Acta Bio Materials, vol. 9, No. 12, Dec. 1, 2013, pp. 9258-9269, Amsterdam, NL (25 Pages).

Cuchiara, Maude L., et al. "Covalent immobilization of stem cell factor and stromal derived factor 1α for in vitro culture of hematopoietic progenitor cells." Acta biomaterialia 9.12 (2013): 9258-9269.

Da Silva, Ricardo MP, Joao F. Mano, and Rui L. Reis. "Smart thermoresponsive coatings and surfaces for tissue engineering: switching cell-material boundaries." Trends in Biotechnology 25.12 (2007): 577-583.

Dash PK, Hochner B, Kandel ER. Injection of the camp-responsive element into the nucleus of aplysia sensory neurons blocks long-term facilitation. Nature. 1990;345:718-721.

Dash PK, Johnson D, Clark J, Orsi SA, Zhang M, Zhao J, Grill RJ, Moore AN, Pati S. Involvement of the glycogen synthase kinase-3 signaling pathway in tbi pathology and neurocognitive outcome. PloS one. 2011;6:e24648.

Dash PK, Mach SA, Blum S, Moore AN. Intrahippocampal wortmannin infusion enhances long-term spatial and contextual memories. Learn Mem. 2002;9:167-177.

Dash PK, Orsi SA, Zhang M, Grill RJ, Pati S, Zhao J, Moore AN. Valproate administered after traumatic brain injury provides neuroprotection and improves cognitive function in rats. PloS one. 2010;5:e11383.

Dash PK, Zhao J, Orsi SA, Zhang M, Moore AN. Sulforaphane improves cognitive function administered following traumatic brain injury. Neuroscience letters. 2009;460:103-107.

Davila et al., "Efficacy and Toxicity Management of 19-28z CAR T Cell Therapy in B cell Acute Lymphoblastic Leukemia," Science Translational Medicine, vol. 6, No. 224, pp. 1-10, Feb. 19, 2014.

Dejana E, Orsenigo F, Lampugnani MG. The role of adherens junctions and ve-cadherin in the control of vascular permeability. Journal of cell science. 2008;121:2115-2122.

Dejana E, Spagnuolo R, Bazzoni G. Interendothelial junctions and their role in the control of angiogenesis, vascular permeability and leukocyte transmigration. Thrombosis and haemostasis. 2001;86:308-315.

Dejana E, Tournier-Lasserve E, Weinstein BM. The control of vascular integrity by endothelial cell junctions: Molecular basis and pathological implications. Developmental cell. 2009;16:209-221.

Del Pino A, Ligero G, Lopez MB, et al. (2015) Morphology, cell viability, karyotype, expression of surface markers and plasticity of three primary cell line cultures before and after the cryostorage in LN2 and GN2. Cryobiology 70(1): 1-8.

Delaney, Colleen, et al. "Notch-mediated expansion of human cord blood progenitor cells capable of rapid myeloid reconstitution." Nature medicine 16.2 (2010): 232-236.

Ding, Zhongli, Guohua Chen, and Allan S. Hoffman. "Synthesis and purification of thermally sensitive oligomer? enzyme conjugates of poly (N-isopropylacrylamide)? trypsin." Bioconjugate chemistry 7.1 (1996): 121-125.

Dixon CE, Clifton GL, Lighthall JW, Yaghmai AA, Hayes RL. A controlled cortical impact model of traumatic brain injury in the rat. Journal of neuroscience methods. 1991;39:253-262.

Dominici M, Le Blanc K, Mueller I, et al. (2006) Minimal criteria for defining multipotent mesenchymal stromal cells. The International Society for Cellular Therapy position statement. Cytotherapy 8(4): 315-317.

Durrani S, Konoplyannikov M, Ashraf M, Haider KH (2010) Skeletal myoblasts for cardiac repair. Regen Med 5(6): 919-932.

Esensten JH, Muller YD, Bluestone JA, Tang Q. Regulatory T-cell therapy for autoimmune and autoinflammatory diseases: The next frontier. J Allergy Clin Immunol. 2018;142(6):1710-1718.

Fakin R, Hamacher J, Gugger M, Gazdhar A, Moser H, Schmid RA. Prolonged amelioration of acute lung allograft rejection by sequential overexpression of human interleukin-10 and hepatocyte growth factor in rats. Exp Lung Res. 2011;37(9):555-62.

Fedorov et al., "PD-1- and CTLA-4-Based Inhibitory Chimeric Antigen Receptors (iCARs) Divert Off-Target Immunotherapy Responses," Science Translational Medicine, vol. 5, No. 215, pp. 1-12, Dec. 11, 2013.

Ferreira LMR, Muller YD, Bluestone JA, Tang Q. Next-generation regulatory T cell therapy. Nat Rev Drug Discov. 2019;18(10):749-769.

Fischbach, Michael A., Jeffrey A. Bluestone, and Wendell A. Lim. "Cell-based therapeutics: the next pillar of medicine." Science translational medicine 5.179 (2013): 179ps7-179ps7.

Fisk, Nicholas M., et al. "Can routine commercial cord blood banking be scientifically and ethically justified ?." PLoS medicine 2.2 (2005): e44.

Forbes Jun. 23, 2014 article "Will this man cure cancer?"

Fowler DH. Rapamycin-resistant effector T-cell therapy. Immunol Rev. 2014;257(1):210-25.

Frank, Nathan D. et al., "Evaluation of Reagents Used to Coat the Holow-Fiber Bioreactor Membrane of the Quantum Cell Expansion System for the Culture of Human Mesenchymal Stem Cells",

(56) References Cited

OTHER PUBLICATIONS

Materials Science and Engineering C, Elsevier Sciense S.A., Ch, vol. 96, Oct. 26, 2018, pp. 77-85.

Fraser H, Safinia N, Grageda N, Thirkell S, Lowe K, Fry LJ, Scotta C, Hope A, Fisher C, Hilton R, Game D, Harden P, Bushell A, Wood K, Lechler RI, Lombardi G. A Rapamycin-Based GMP-Compatible Process for the Isolation and Expansion of Regulatory T Cells for Clinical Trials. Mol Ther Methods Clin Dev. 2018;8:198-209.

Frauwirth KA, Riley JL, Harris MH, Parry RV, Rathmell JC, Plas DR, Elstrom RL, June CH, Thompson CB. The CD28 signaling pathway regulates glucose metabolism. Immunity. 2002;16(6):769-77.

Fuchs A, Gliwinski M, Grageda N, Spiering R, Abbas AK, Appel S, Bacchetta R, Battaglia M, Berglund D, Blazar B, Bluestone JA, Bornhauser M, Ten Brinke A, Brusko TM, Cools N, Cuturi MC, Geissler E, Giannoukakis N, Golab K, Hafler DA, van Ham SM, Hester J et al. Minimum Information about T Regulatory Cells: A Step toward Reproducibility and Standardization. Front Immunol. 2017;8:1844.

G0211: Study for Gamma Irradiation of Bioreactor Membranes, undated, author unknown, 3 pages.

Galgani M, De Rosa V, La Cava A, Matarese G. Role of Metabolism in the Immunobiology of Regulatory T Cells. J Immunol. 2016;197(7):2567-75.

Garlie, Nina K., et al. "T cells coactivated with immobilized anti-CD3 and anti-CD28 as potential immunotherapy for cancer." Journal of immunotherapy (Hagerstown, Md.: 1997) 22.4 (1999): 336-345.

Gedaly R, De Stefano F, Turcios L, Hill M, Hidalgo G, Mitov MI, Alstott MC, Butterfield DA, Mitchell HC, Hart J, Al-Attar A, Jennings CD, Marti F. mTOR Inhibitor Everolimus in Regulatory T Cell Expansion for Clinical Application in Transplantation. Transplantation. 2019;103(4):705-715.

Gimble, Jeffrey M., Adam J. Katz, and Bruce A. Bunnell. "Adipose-derived stem cells for regenerative medicine." Circulation research 100.9 (2007): 1249-1260.

Gingras AC, Raught B, Sonenberg N. Regulation of translation initiation by FRAP/mTOR. Genes Dev. 2001;15(7):807-26.

Godin, Michel, et al. "Measuring the mass, density, and size of particles and cells using a suspended microchannel resonator." Applied physics letters 91.12 (2007): 123121.

Goh, Celeste, Sowmya Narayanan, and Young S. Hahn. "Myeloid-derived suppressor cells: the dark knight or the joker in viral infections?." *Immunological reviews* 255.1 (2013): 210-221.

Golab K, Leveson-Gower D, Wang XJ, Grzanka J, Marek-Trzonkowska N, Krzystyniak A, Millis JM, Trzonkowski P, Witkowski P. Challenges in cryopreservation of regulatory T cells (Tregs) for clinical therapeutic applications. Int Immunopharmacol. 2013;16(3):371-5.

Goldring CE, Duffy PA, Benvenisty N, Andrews PW, Ben-David U, Eakins R, French N, Hanley NA, Kelly L, Kitteringham NR, Kurth J, Ladenheim D, Laverty H, McBlane J, Narayanan G, Patel S, Reinhardt J, Rossi A, Sharpe M, Park BK. Assessing the safety of stem cell therapeutics. Cell stem cell. 2011;8:618-628.

Griesche, Nadine, et al. "A simple modification of the separation method reduces heterogeneity of adipose-derived stem cells." cells tissues organs 192.2 (2010): 106-115.

Gutcher I, Donkor MK, Ma Q, Rudensky AY, Flavell RA, Li MO. Autocrine transforming growth factor-beta1 promotes in vivo Th17 cell differentiation. Immunity. 2011;34(3):396-408.

Haack-Sorensen M, Follin B, Juhl M, et al. (2016) Culture expansion of adipose derived stromal cells. A closed automated Quantum Cell Expansion System compared with manual flask-based culture. J Transl Med 14(1): 319.

Hall ED, Sullivan PG, Gibson TR, Pavel KM, Thompson BM, Scheff SW. Spatial and temporal characteristics of neurodegeneration after controlled cortical impact in mice: More than a focal brain injury. Journal of neurotrauma. 2005;22:252-265.

Hami et al., "GMP Production and Testing of Xcellerated T Cells for the Treatment of Patients with CLL," Cytotherapy, pp. 554-562, 2004.

Hamm RJ, Dixon CE, Gbadebo DM, Singha AK, Jenkins LW, Lyeth BG, Hayes RL. Cognitive deficits following traumatic brain injury produced by controlled cortical impact. Journal of neurotrauma. 1992;9:11-20.

Hanley PJ, Mei Z, Durett AG, et al. (2014) Efficient manufacturing of therapeutic mesenchymal stromal cells with the use of the Quantum Cell Expansion System. Cytotherapy 16(8): 1048-1058.

Harimoto, Masami, et al. "Novel approach for achieving double-layered cell sheets co-culture: overlaying endothelial cell sheets onto monolayer hepatocytes utilizing temperature-responsive culture dishes." Journal of Biomedical Materials Research: An Official Journal of The Society for Biomaterials, The Japanese Society for Biomaterials, and The Australian Society for Biomaterials and the Korean Society for Biomaterials 62.3 (2002): 464-470.

He N, Fan W, Henriquez B, Yu RT, Atkins AR, Liddle C, Zheng Y, Downes M, Evans RM. Metabolic control of regulatory T cell (Treg) survival and function by Lkb1. Proc Natl Acad Sci USA. 2017;114(47):12542-12547.

He X, Landman S, Bauland SC, van den Dolder J, Koenen HJ, Joosten I. A TNFR2-Agonist Facilitates High Purity Expansion of Human Low Purity Treg Cells. PLoS One. 2016;11(5):e0156311.

Heskins, Michael, and James E. Guillet. "Solution properties of poly (N-isopropylacrylamide)." Journal of Macromolecular Science—Chemistry 2.8 (1968): 1441-1455.

Hill JA, Feuerer M, Tash K, Haxhinasto S, Perez J, Melamed R, Mathis D, Benoist C. Foxp3 transcription-factor-dependent and -independent regulation of the regulatory T cell transcriptional signature. Immunity. 2007;27(5):786-800.

Högstedt, Benkt, Anita Karlsson, and Anders Holmén. "Frequency and size distribution of micronuclei in lymphocytes stimulated with phytohemagglutinin and pokeweed mitogen in workers exposed to piperazine." Hereditas 109.(1988): 139-142.

Hollyman et al., "Manufacturing Validation of Biologicall Functional T Cells Targeted to CD19 Antigen for Autologous Adoptive Cell Therapy," J Immunother, vol. 32, No. 2, pp. 169-180, Feb.-Mar. 2009.

Horwitz, Mitchell E., et al. "Phase I/II study of stem-cell transplantation using a single cord blood unit expanded ex vivo with nicotinamide." *Journal of Clinical Oncology* 37.5 (2019): 367-373.

International Search Report for corresponding International Application No. PCT/US2022/021595 dated Jul. 1, 2022 (4 Pages).

Itkin, Tomer, and Tsvee Lapidot. "SDF-1 keeps HSC quiescent at home." Blood, The Journal of the American Society of Hematology 117.2 (2011): 373-374.

Iwashima, Shigejiro, et al. "Novel culture system of mesenchymal stromal cells from human subcutaneous adipose tissue." Stem cells and development 18.4 (2009): 533-544.

Jang, Eugene, et al. "Syndecan-4 proteoliposomes enhance fibroblast growth factor-2 (FGF-2)-induced proliferation, migration, and neovascularization of ischemic muscle." Proceedings of the National Academy of Sciences 109.5 (2012): 1679-1684.

Jarocha D, Stangel-Wojcikiewicz K, Basta A, Majka M (2014) Efficient myoblast expansion for regenerative medicine use. Int J Mol Med 34(1): 83-91.

Jin, H., and J. Bae. "Neuropeptide Y regulates the hematopoietic stem cell microenvironment and prevents nerve injury in the bone marrow." *22nd Annual ISCT Meeting* (2016): S29.

Jo CH, Lee YG, Shin WH, et al. (2014) Intra-articular injection of mesenchymal stem cells for the treatment of osteoarthritis of the knee: a proof-of-concept clinical trial. Stem Cells 32(5): 1254-1266.

Johansson, Ulrika, et al. "Pancreatic islet survival and engraftment is promoted by culture on functionalized spider silk matrices." PloS one 10.6 (2015): e0130169.

John Carvell, et al. Monitoring Live Biomass in Disposable Bioreactors, BioProcess International 14(3)s, Mar. 2016.

John Nicolette, et al (Abbott Laboratories). In Vitro Micronucleus Screening of Pharmaceutical Candidates by Flow Cyto9metry in Chinese Hamster V79 Cells, Environmental and Molecular Mutagenesis 00:000-000, 2010.

(56) References Cited

OTHER PUBLICATIONS

John P. Carvell and Jason E. Dowd. On-line measurements and control of viable cell density in cell culture manufacturing processes using radio frequency impedance. Cytotechnology 50: 35-48, 2006.
Johnson, Patrick A., et al. "Interplay of anionic charge, poly (ethylene glycol), and iodinated tyrosine incorporation within tyrosine? derived polycarbonates: Effects on vascular smooth muscle cell adhesion, proliferation, and motility." Journal of Biomedical Materials Research Part A: An Official Journal of The Society for Biomaterials, The Japanese Society for Biomaterials, and The Australian Society for Biomaterials and the Korean Society for Biomaterials 93.2 (2010): 505-514.
Johnston LC, Su X, Maguire-Zeiss K, Horovitz K, Ankoudinova I, Guschin D, Hadaczek P, Federoff HJ, Bankiewicz K, Forsayeth J. Human interleukin-10 gene transfer is protective in a rat model of Parkinson's disease. Mol Ther. 2008;16(8):1392-9.
Jones M, Varella-Garcia M, Skokan M, et al. (2013) Genetic stability of bone marrow-derived human mesenchymal stromal cells in the Quantum System. Cytotherapy 15(11): 1323-1339.
Jones, M., "The Monoculture of Cord Blood-Derived CD34+ Cells by Perfusion Using a Semi-Permeable Hollow Fiber Membrane Quantum Cell Expansion System With a Novel Growth Factor Cocktail", Cytotherapy, vol. 23, No. 5, May 25, 2021, p. S84. Jones2016ISCT 2016 Poster 69.
Joy, Abraham, et al. "Control of surface chemistry, substrate stiffness, and cell function in a novel terpolymer methacrylate library." Langmuir 27.5 (2011): 1891-1899.
Kalamasz et al., "Optimization of Human T-Cell Expansion Ex Vivo Using Magnetic Beads Conjugated with Anti-CD3 and Anti-CD28 Antibodies," J Immunother, vol. 27, No. 5, pp. 405-418, Sep.-Oct. 2004.
Kim, Do-Hyung, et al. "mTOR interacts with raptor to form a nutrient-sensitive complex that signals to the cell growth machinery." Cell 110.2 (2002): 163-175.
Kishore M, Cheung KCP, Fu H, Bonacina F, Wang G, Coe D, Ward EJ, Colamatteo A, Jangani M, Baragetti A, Matarese G, Smith DM, Haas R, Mauro C, Wraith DC, Okkenhaug K, Catapano AL, De Rosa V, Norata GD, Marelli-Berg FM. Regulatory T Cell Migration Is Dependent on Glucokinase-Mediated Glycolysis. Immunity. 2017;47(5):875-889 e10.
Klapper et al., "Single-Pass, Closed-System Rapid Expansion of Lymphocyte Cultures for Adoptive Cell Therapy," Journal of Immunological Methods, 345, pp. 90-99, Apr. 21, 2009.
Klein, Elias, Eva Eichholz, and Don H. Yeager. "Affinity membranes prepared from hydrophilic coatings on microporous polysulfone hollow fibers." Journal of membrane science 90.1-2 (1994): 69-80.
Klysz D, Tai X, Robert PA, Craveiro M, Cretenet G, Oburoglu L, Mongellaz C, Floess S, Fritz V, Matias MI, Yong C, Surh N, Marie JC, Huehn J, Zimmermann V, Kinet S, Dardalhon V, Taylor N. Glutamine-dependent alpha-ketoglutarate production regulates the balance between T helper 1 cell and regulatory T cell generation. Sci Signal. 2015;8(396):ra97.
Korpanty et al., "Tageting Vascular Enothelium with Avidin Microbubbles," Ultrasound in Medicine and Biology, vol. 31, No. 9, pp. 1279-1283, May 24, 2005.
Krauss et al., "Signaling Takes a Breath—New Quantitative Perspectives on Bioenergetics and Signal Transduction," Immunity, vol. 15, pp. 497-502, Oct. 2001.
Kulikov, A. V., et al. "Application of multipotent mesenchymal stromal cells from human adipose tissue for compensation of neurological deficiency induced by 3-nitropropionic acid in rats." Bulletin of experimental biology and medicine 145.4 (2008): 514-519.
Kumar P, Marinelarena A, Raghunathan D, Ragothaman VK, Saini S, Bhattacharya P, Fan J, Epstein AL, Maker AV, Prabhakar BS. Critical role of OX40 signaling in the TCR-independent phase of human and murine thymic Treg generation. Cell Mol Immunol. 2019;16(2):138-153.

Kwan, J. and Borden, M., "Lipid Monolayer Collapse and Microbubble Stability," Advances in Colloid and Interface Science, vols. 183-184, pp. 82-99, Aug. 21, 2012.
Lampugnani MG, Caveda L, Breviario F, Del Maschio A, Dejana E. Endothelial cell-to-cell junctions. Structural characteristics and functional role in the regulation of vascular permeability and leukocyte extravasation. Bailliere's clinical haematology. 1993;6:539-558.
Lang, Julie, et al. "Generation of hematopoietic humanized mice in the newborn BALB/c-Rag2nullIl2rynull mouse model: a multivariable optimization approach." Clinical Immunology 140.1 (2011): 102-116.
Lataillade, Jean-Jacques, et al. "Chemokine SDF-1 enhances circulating CD34+ cell proliferation in synergy with cytokines: possible role in progenitor survival." Blood, The Journal of the American Society of Hematology 95.3 (2000): 756-768.
Lechanteur, Chantal et al., "Large-Scale Clinical Expansion of Mesenchymal Stem Cells in the GMP-Compliant, Closed Automated Quantum Cell Expansion System: Comparison With Expansion in Traditional T-Flasks", Journal of Stem Cell Research & Therapy, vol. 4, No. 08, Aug. 7, 2014 (12 Pages).
Lee et al., "Continued Antigen Stimulation Is Not Required During CD4+ T Cell Clonal Expansion," The Journal of Immunology, 168, pp. 1682-1689, 2002.
Lee III, Daniel W., et al. "Long-term outcomes following CD19 CAR T cell therapy for B-ALL are superior in patients receiving a fludarabine/cyclophosphamide preparative regimen and post-CAR hematopoietic stem cell transplantation." Blood 128.22 (2016): 218.
Lee, Jae W., et al. "Allogeneic human mesenchymal stem cells for treatment of E. coli endotoxin-induced acute lung injury in the ex vivo perfused human lung." Proceedings of the national academy of Sciences 106.38 (2009): 16357-16362.
Levine, B., "T Lymphocyte Engineering ex vivo for Cancer and Infectious Disease," Expert Opinion on Biological Therapy, vol. 4, No. 4, pp. 475-489, 2008.
Lindstein, Tullia, et al. "Regulation of lymphokine messenger RNA stability by a surface-mediated T cell activation pathway." Science 244.4902 (1989): 339-343.
Liotta, Francesco, et al. "Frequency of regulatory T cells in peripheral blood and in tumour-infiltrating lymphocytes correlates with poor prognosis in renal cell carcinoma." BJU international 107.9 (2011): 1500-1506.
Liu W, Putnam AL, Xu-Yu Z, Szot GL, Lee MR, Zhu S, Gottlieb PA, Kapranov P, Gingeras TR, Fazekas de St Groth B, Clayberger C, Soper DM, Ziegler SF, Bluestone JA. CD127 expression inversely correlates with FoxP3 and suppressive function of human CD4+ T reg cells. J Exp Med. 2006;203(7):1701-1711.
Lum et al., "Ultrasound Radiation Force Enables Targeted Deposition of Model Drug Carriers Loaded on Microbubbles," Journal of Controlled Release, 111, pp. 128-134, 2006.
M. R. Koller, et al. Clinical-scale human umbilical cord blood cell expansion in a novel automated perfusion culture system. Bone Marrow Transplantion 21:653-663, 1998.
Malin, Stephen F., et al. "Noninvasive prediction of glucose by near-infrared diffuse reflectance spectroscopy." (1999): 1651-1658.
Malone et al., "Characterization of Human Tumor-Infiltrating Lymphocytes Expanded in Hollow-Fiber Bioreactors for Immunotherapy of Cancer," Cancer Biotherapy & Radiopharmaceuticals, vol. 16, No. 5, pp. 381-390, 2001.
Mao AS, Mooney DJ (2015) Regenerative medicine: current therapies and future directions. Proc Natl Acad Sci USA 112(47): 14452-14459.
Marek-Trzonkowska, Natalia, et al. "Administration of CD4+ CD25highCD127-regulatory T cells preserves β-cell function in type 1 diabetes in children." Diabetes care 35.9 (2012): 1817-1820.
Markgraf CG, Clifton GL, Aguirre M, Chaney SF, Knox-Du Bois C, Kennon K, Verma N. Injury severity and sensitivity to treatment after controlled cortical impact in rats. Journal of neurotrauma. 2001; 18:175-186.
Mathew et al. A Phase I Clinical Trials I with Ex Vivo Expanded Recipient Regulatory T cells in Living Donor Kidney Transplants. Nature, Scientific Reports 8:7428 (1-12), 2018.

(56) References Cited

OTHER PUBLICATIONS

Mathew, James M., et al. "A phase I clinical trial with ex vivo expanded recipient regulatory T cells in living donor kidney transplants." *Scientific reports* 8.1 (2018): 1-12.
Matthay, Michael A., et al. "Therapeutic potential of mesenchymal stem cells for severe acute lung injury." Chest 138.4 (2010): 965-972.
Maynard CL, Harrington LE, Janowski KM, Oliver JR, Zindl CL, Rudensky AY, Weaver CT. Regulatory T cells expressing interleukin 10 develop from Foxp3+ and Foxp3− precursor cells in the absence of interleukin 10. Nat Immunol. 2007;8(9):931-41.
McKenna DH, Jr., Sumstad D, Kadidlo DM, et al. Optimization of cGMP purification and expansion of umbilical cord blood-derived T-regulatory cells in support of first-in-human clinical trials. Cytotherapy 2017;19:250-62.
McLimans W, Kinetics of Gas Diffusion in Mammalian Cell Culture Systems. Biotechnology and Bioengineering 1968; 10:725-740.
McMurtrey, Richard J. "Analytic models of oxygen and nutrient diffusion, metabolism dynamics, and architecture optimization in three-dimensional tissue constructs with applications and insights in cerebral organoids." Tissue Engineering Part C: Methods 22.3 (2016): 221-249.
Menge, Tyler, et al. "Mesenchymal stem cells regulate blood-brain barrier integrity through TIMP3 release after traumatic brain injury." Science translational medicine 4.161 (2012): 161ra150-161ra150.
Miska J, Lee-Chang C, Rashidi A, Muroski ME, Chang AL, Lopez-Rosas A, Zhang P, Panek WK, Cordero A, Han Y, Ahmed AU, Chandel NS, Lesniak MS. HIF-1alpha Is a Metabolic Switch between Glycolytic-Driven Migration and Oxidative Phosphorylation-Driven Immunosuppression of Tregs in Glioblastoma. Cell Rep. 2019;27(1):226-237 e4.
Miyara M, Yoshioka Y, Kitoh A, Shima T, Wing K, Niwa A, Parizot C, Taflin C, Heike T, Valeyre D, Mathian A, Nakahata T, Yamaguchi T, Nomura T, Ono M, Amoura Z, Gorochov G, Sakaguchi S. Functional delineation and differentiation dynamics of human CD4+ T cells expressing the FoxP3 transcription factor. Immunity. 2009;30(6):899-911.
Murugappan, G., et al. "Human hematopoietic progenitor cells grow faster under rotational laminar flows." Biotechnology progress 26.5 (2010): 1465-1473.
Nankervis B, Jones M, Vang B et al. (2018) Optimizing T Cell Expansion in a Hollow-Fiber Bioreactor. Curr Stem Cell Rep. Advanced online publication. https://doi.org/10.1007/s40778-018-0116-x.
Nankervis, Brian, et al. "Optimizing T cell expansion in a hollow-fiber bioreactor." Current Stem Cell Reports 4.1 (2018): 46-51.
Nedoszytko B, Lange M, Sokolowska-Wojdylo M, Renke J, Trzonkowski P, Sobjanek M, Szczerkowska-Dobosz A, Niedoszytko M, Gorska A, Romantowski J, Czarny J, Skokowski J, Kalinowski L, Nowicki R. The role of regulatory T cells and genes involved in their differentiation in pathogenesis of selected inflammatory and neoplastic skin diseases. Part II: The Treg role in skin diseases pathogenesis. Postep Dermatol Alergol. 2017;34(5):405-417.
Nehlin JO, Just M, Rustan AC (2011) Human myotubes from myoblast cultures undergoing senescence exhibit defects in glucose and lipid metabolism. Biogerontology 12: 349-365.
New victories for adult Stem Cell Research New York Feb. 6, 2007.
Newton R, Priyadharshini B, Turka LA. Immunometabolism of regulatory T cells. Nat Immunol. 2016;17(6):618-25.
Ng TH, Britton GJ, Hill EV, Verhagen J, Burton BR, Wraith DC. Regulation of adaptive immunity; the role of interleukin-10. Front Immunol. 2013;4:129.
Nikolaychik, V. V., M. M. Samet, and P. I. Lelkes. "A New, Cryoprecipitate Based Coating For Improved Endothelial Cell Attachment And Growth On Medical Grade Artificial Surfaces." ASAIO Journal (American Society for Artificial Internal Organs: 1992) 40.3 (1994): M846-52.
Nish SA, Schenten D, Wunderlich FT, Pope SD, Gao Y, Hoshi N, Yu S, Yan X, Lee HK, Pasman L, Brodsky I, Yordy B, Zhao H,
Bruning J, Medzhitov R. T cell-intrinsic role of IL-6 signaling in primary and memory responses. Elife. 2014;3:e01949.
Niwayama, Jun, et al. "Analysis of hemodynamics during blood purification therapy using a newly developed noninvasive continuous monitoring method." Therapeutic Apheresis and Dialysis 10.4 (2006): 380-386.
Nugent, Helen M., et al. "Adventitial endothelial implants reduce matrix metalloproteinase-2 expression and increase luminal diameter in porcine arteriovenous grafts." Journal of vascular surgery 46.3 (2007): 548-556.
Okano et al (Tokyo Women's Medical College, Japan) demonstrated the recovery of endothelial cells and hepatocytes from plasma-treated polystyrene dishes grafted with PNIAAm (Journal of Biomedical Materials Research, 1993).
Onishi Y, Fehervari Z, Yamaguchi T, Sakaguchi S. Foxp3+ natural regulatory T cells preferentially form aggregates on dendritic cells in vitro and actively inhibit their maturation. Proc Natl Acad Sci U S A. 2008;105(29):10113-8.
Onyszchuk G, LeVine SM, Brooks WM, Berman NE. Post-acute pathological changes in the thalamus and internal capsule in aged mice following controlled cortical impact injury: A magnetic resonance imaging, iron histochemical, and glial immunohistochemical study. Neuroscience letters. 2009;452:204-208.
Pacella I, Procaccini C, Focaccetti C, Miacci S, Timperi E, Faicchia D, Severa M, Rizzo F, Coccia EM, Bonacina F, Mitro N, Norata GD, Rossetti G, Ranzani V, Pagani M, Giorda E, Wei Y, Matarese G, Barnaba V, Piconese S. Fatty acid metabolism complements glycolysis in the selective regulatory T cell expansion during tumor growth. Proc Natl Acad Sci U S A. 2018;115(28):E6546-E6555.
Parhi, Purnendu, Avantika Golas, and Erwin A. Vogler. "Role Of Proteins And Water In The Initial Attachment Of Mammalian Cells To Biomedical Surfaces: A Review." Journal of Adhesion Science and Technology 24.5 (2010): 853-888.
Pati S, Gerber MH, Menge TD, Wataha KA, Zhao Y, Baumgartner JA, Zhao J, Letourneau PA, Huby MP, Baer LA, Salsbury JR, Kozar RA, Wade CE, Walker PA, Dash PK, Cox CS, Jr., Doursout MF, Holcomb JB. Bone marrow derived mesenchymal stem cells inhibit inflammation and preserve vascular endothelial integrity in the lungs after hemorrhagic shock. PloS one. 2011;6:e25171.
Pati S, Khakoo AY, Zhao J, Jimenez F, Gerber MH, Harting M, Redell JB, Grill R, Matsuo Y, Guha S, Cox CS, Reitz MS, Holcomb JB, Dash PK. Human mesenchymal stem cells inhibit vascular permeability by modulating vascular endothelial cadherin/beta-catenin signaling. Stem cells and development. 2011;20:89-101.
Pati, Shibani, and Todd E. Rasmussen. "Cellular therapies in trauma and critical care medicine: Looking towards the future." *PLoS Medicine* 14.7 (2017): e1002343.
Pati, Shibani, et al. "Lyophilized plasma attenuates vascular permeability, inflammation and lung injury in hemorrhagic shock." *PLoS one* 13.2 (2018): e0192363.
Peters JH, Preijers FW, Woestenenk R, Hilbrands LB, Koenen HJ, Joosten I. Clinical grade Treg: GMP isolation, improvement of purity by CD127 Depletion, Treg expansion, and Treg cryopreservation. PLoS One. 2008;3(9):e3161.
Peters, R.; Jones, M.; Brecheisen, M.; Startz, T.; Vang, B.; Nankervis, B.; Frank, N.; Nguyen, K. (2012) TerumoBCT. https://www.terumobct.com/location/north-america/products-and-services/Pages/Quantum-Materials.aspx.
Porter CM, Horvath-Arcidiacono JA, Singh AK, Horvath KA, Bloom ET, Mohiuddin MM. Characterization and expansion of baboon CD4+CD25+ Treg cells for potential use in a non-human primate xenotransplantation model. Xenotransplantation. 2007;14(4):298-308.
Povsic TJ, O'Connor CM, Henry T, et al. (2011) A double-blind, randomized, controlled, multicenter study to assess the safety and cardiovascular effects of skeletal myoblast implantation by catheter delivery in patients with chronic heart failure after myocardial infarction. Am Heart J 162(4): 654-662.
Prockop, Darwin J., Carl A. Gregory, and Jeffery L. Spees. "One strategy for cell and gene therapy: harnessing the power of adult stem cells to repair tissues." Proceedings of the National Academy of Sciences 100.suppl_1 (2003): 11917-11923.

(56) References Cited

OTHER PUBLICATIONS

Q. L. Hao, et al. A functional comparison of CD34+ CD38= cells in cord blood and bone marrow. Blood 86:3745-3753, 1995.
Rahmahwati, Nurlaela, Deana Wahyuningrum, and Anita Alni. "The Synthesis Of Polyethersulfone (PES) Derivatives For The Immobilization Of Lipase Enzyme." Key Engineering Materials. vol. 811. Trans Tech Publications Ltd, 2019.
Rey-Jurado, Emma, et al. "Assessing the importance of domestic vaccine manufacturing centers: an overview of immunization programs, vaccine manufacture, and distribution." Frontiers in immunology 9 (2018): 26.
Roballo KC, Dhungana S, Z. J, Oakey J, Bushman J. Localized delivery of immunosuppressive regulatory T cells to peripheral nerve allografts promotes regeneration of branched segmental defects. Biomaterials. 2019;209:1-9.
Rodrigues, C., Fernandes, T., Diogo, M., Lobato da Silva, C., Cabral, J. Stem Cell Cultivation in Bioreactors. 2011. Biotechnology Advances v. 29, pp. 815-829.
Ronco C1, Levin N, Brendolan A, Nalesso F, Cruz D, Ocampo C, Kuang D, Bonello M, De Cal M, Corradi V, Ricci Z. Flow distribution analysis by helical scanning in polysulfone hemodialyzers: effects of fiber structure and design on flow patterns and solute clearances. Hemodial Int. Oct. 2006; 10(4):380-8.
Ronco, C., Brendolan, A., Crepaldi, C., Todighiero, M., Scabardi, M. Blood and Dialysate Flow Distributions in Hollow-Fiber Hemodialyzers Analyzed by Computerized Helical Scanning Technique. 2002. Journal of the American Society of Nephrology. V. 13, pp. S53-S61.
Rosenblum MD, Way SS, Abbas AK. Regulatory T cell memory. Nat Rev Immunol. 2016;16(2):90-101.
Rubtsov YP, Rasmussen JP, Chi EY, Fontenot J, Castelli L, Ye X, Treuting P, Siewe L, Roers A, Henderson WR, Jr., Muller W, Rudensky AY. Regulatory T cell-derived interleukin-10 limits inflammation at environmental interfaces. Immunity. 2008;28(4):546-58.
Rudensky, Alexander Y. "Regulatory T cells and Foxp3." Immunological reviews 241.1 (2011): 260-268.
Ryu, Min-Hyung, and Mark Gomelsky. "Near-infrared light responsive synthetic c-di-GMP module for optogenetic applications." ACS synthetic biology 3.11 (2014): 802-810.
S. Koestenbauer, et al. Protocols for Hematopoietic Stem Cell Expansion from Umbilical Cord Blood. Cell Transplantation 18: 1059-1068, 2009.
S. L. Smith, et al. Expansion of neutrophil precursors and progenitors in suspension cultures of CD34+ cells enriched from human bone marrow. Experimental Hematology 21:870-877, 1993.
Safinia N, Grageda N, Scotta C, Thirkell S, Fry LJ, Vaikunthanathan T, Lechler RI, Lombardi G. Cell Therapy in Organ Transplantation: Our Experience on the Clinical Translation of Regulatory T Cells. Front Immunol. 2018;9:354.
Sahay A, Scobie KN, Hill AS, O'Carroll CM, Kheirbek MA, Burghardt NS, Fenton AA, Dranovsky A, Hen R. Increasing adult hippocampal neurogenesis is sufficient to improve pattern separation. Nature. 2011;472:466-470.
Sakaguchi S, Sakaguchi N, Asano M, Itoh M, Toda M. Immunologic self-tolerance maintained by activated T cells expressing IL-2 receptor alpha-chains (CD25). Breakdown of a single mechanism of self-tolerance causes various autoimmune diseases. J Immunol. 1995;155(3):1151-64.
Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25+ CD4+ regulatory T cells: their common role in controlling autoimmunity, tumor immunity, and transplantation tolerance. Immunol Rev. 2001;182:18-32.
Schild, Howard G. "Poly (N-isopropylacrylamide): experiment, theory and application." Progress in polymer science 17.2 (1992): 163-249.
Schmitz R, Alessio A, Kina P. The Physics of PET/CT scanners. Imaging Research Laboratory, Department of Radiology, University of Washington http://depts.washington.edu/imreslab/education/Physics%20of%20PET.pdf.

Schwartz RH. T cell anergy. Annu Rev Immunol. 2003;21:305-34.
Shevkoplyas et al., "The Force Acting on a Superparamagnetic Bead due to an Applied Magnetic Field," Lab on a Chip , 7, pp. 1294-1302, 2007.
Shimazu Y, Shimazu Y, Hishizawa M, Hamaguchi M, Nagai Y, Sugino N, Fujii S, Kawahara M, Kadowaki N, Nishikawa H, Sakaguchi S, Takaori-Kondo A. Hypomethylation of the Treg-Specific Demethylated Region in FOXP3 Is a Hallmark of the Regulatory T-cell Subtype in Adult T-cell Leukemia. Cancer Immunol Res. 2016;4(2):136-45.
Shimizu et all., "Fabrication of Pulsatile Cardiac Tissue Grafts Using a Novel 3-Dimensional Cell Sheet Manipulation Technique and Temperature-Responsive Cell Culture Surfaces," Circulation Research, vol. 90, Feb. 22, 2022, e40-e48, pp. 1-9.
Sigma-Aldrich Cheimcals Mitomycin C (M4287) MSDS, v4.4, Jul. 7, 2011.
Sirsi, S. and Borden, M., "Microbubble Composition, Properties, and Biomedical Applications," Bubble Science, Engineering & Technolology, vol. 1, No. 1-2, pp. 3-17, 2009.
Smith C, Okern G, Rehan S, et al. Ex vivo expansion of human T cells for adoptive immunotherapy using the novel Xeno-free CTS Immune Cell Serum Replacement. Clinical & Translational Immunology 2015;4:e31.
Somerville et al., "Clinical Scale Rapid Expansion of Lymphocytes for Adoptive Cell Transfer Therapy in the WAVE® Bioreactor," Journal of Translational Medicine, vol. 10, No. 69, pp. 1-11, 2012.
Somerville, R. and Dudley, M., "Bioreactors Get Personal," Oncolmmunology, vol. 1, No. 8, pp. 1435-1437, Nov. 2012.
Spectrum Labs KrosFlo Research Ili TFF System, undated, Spectrum Laboratories, Inc., 4 pages.
Stafano Tiziani, et al. Metabolomic Profiling of Drug Response in Acute Myeloid Leukaemia Cell lines. PLOSone 4(1): e4251 (Jan. 22, 2009).
StAR_Abstract, undated, author unknown, 1 page.
Startz et al May 2016 TBCT T-cell White Paper.
Startz, T., et al. "Maturation of dendritic cells from CD14+ monocytes in an automated functionally closed hollow fiber bioreactor system." Cytotherapy 16.4 (2014): S29.
Steven M. Bryce, et al (Litron Laboratories). In vitro micronucleus assay scored by flow cytometry provides a comprehensive evaluation of cytogenetic damage and cytotoxicity. Mutation Research 630(1-2): 78-91, 2007.
Steven M. Bryce, et al (Novartis Pharma AG, Johnson & Johnson Pharmaceutical Research, GlaxoSmithKline). Interlaboratory evaluation of a flow cytometric, high content in vitro micronucleus assay. Genetic Toxicology and Environmental Mutagenesis 650: 181-195, 2008.
Streltsova et al., "Recurrent Stimulation of Natural Killer Cell Clones with K562 Expressing Membrane-Bound interleukin-21 Affects Their Phenotype, Interferon-y Production, and Lifespan," International Journal of Molecular Sciences, vol. 20, No. 443, 2019, pp. 1-18.
Stuart, Martien A. Cohen, et al. "Emerging applications of stimuli-responsive polymer materials." Nature materials 9.2 (2010): 101-113.
Su LF, Del Alcazar D, Stelekati E, Wherry EJ, Davis MM. Antigen exposure shapes the ratio between antigen-specific Tregs and conventional T cells in human peripheral blood. Proc Natl Acad Sci U S A. 2016;113(41):E6192-E6198.
Takezawa, Toshiaki, Yuichi Mori, and Katsutoshi Yoshizato. "Cell culture on a thermo-responsive polymer surface." Bio/technology 8.9 (1990): 854-856.
The effect of rocking rate and angle on T cell cultures grown in Xuri™ Cell Expansion Systems, Aug. 2014, GE Healthcare UK Limited, 4 pages.
Trzonkowski et al., "Ex Vivo Expansion of CD4+ CD25+ T Regulatory Cells for Immunosuppressive Therapy," Cytometry Part A, 75A, pp. 175-188, 2009.
Trzonkowski, Piotr, et al. "First-in-man clinical results of the treatment of patients with graft versus host disease with human ex vivo expanded CD4+ CD25+ CD127? T regulatory cells." Clinical immunology 133.1 (2009): 22-26.

(56) References Cited

OTHER PUBLICATIONS

Tsvetkov, Ts, et al. "Isolation and cryopreservation of human peripheral blood monocytes." Cryobiology 23.6 (1986): 531-536.
Ueda, Ryosuke, et al. "Interaction of natural killer cells with neutrophils exerts a significant antitumor immunity in hematopoietic stem cell transplantation recipients." Cancer medicine 5.1 (2015): 49-60.
Underwood, P. Anne, et al. "Effects of base material, plasma proteins and FGF2 on endothelial cell adhesion and growth." Journal of Biomaterials Science, Polymer Edition 13.8 (2002): 845-862.
Urbich, et al from the Goethe-Universität, demonstrated that human endothelial cells increased VEGFR-2 mRNA expression when exposed to 5-15 dynes/cm2 of constant shear force for a period of 6-24 hours (FEBS, 2002).
Van der Net JB, Bushell A, Wood KJ, Harden PN. Regulatory T cells: first steps of clinical application in solid organ transplantation. Transpl Int. 2016;29(1):3-11.
Van der Windt GJ, Pearce EL. Metabolic switching and fuel choice during T-cell differentiation and memory development. Immunol Rev. 2012;249(1):27-42.
Vera et al., "Accelerated Production of Antigen-Specific T-Cells for Pre-Clinical and Clinical Applications Using Gas-Permeable Rapid Expansion Cultureware (G-Rex)," J Immunother, vol. 33, No. 3, pp. 305-315, Apr. 2010.
Villa, Alma Y. Camacho, et al. "CD133+ CD34+ and CD133+ CD38+ blood progenitor cells as predictors of platelet engraftment in patients undergoing autologous peripheral blood stem cell transplantation." Transfusion and Apheresis Science 46.3 (2012): 239-244.
Visser EP1, Disselhorst JA, Brom M, Laverman P, Gotthardt M, Oyen WJ, Boerman OC. Spatial resolution and sensitivity of the Inveon small-animal PET scanner. J Nucl Med. Jan. 2009;50(1):139-47.
Von Laer, D., et al. "Loss of CD38 antigen on CD34+ CD38+ cells during short-term culture." Leukemia 14.5 (2000): 947-948.
Wagner Jr, John E., et al. "Phase I/II trial of StemRegenin-1 expanded umbilical cord blood hematopoietic stem cells supports testing as a stand-alone graft." Cell stem cell 18.1 (2016): 144-155.
Walker, Peter A., et al. "Direct intrathecal implantation of mesenchymal stromal cells leads to enhanced neuroprotection via an NF?B-mediated increase in interleukin-6 production." Stem cells and development 19.6 (2010): 867-876.
Wang R, Dillon CP, Shi LZ, Milasta S, Carter R, Finkelstein D, McCormick LL, Fitzgerald P, Chi H, Munger J, Green DR. The transcription factor Myc controls metabolic reprogramming upon T lymphocyte activation. Immunity. 2011;35(6):871-82.
Wang, Jiamian, John A. Jansen, and Fang Yang. "Electrospraying: possibilities and challenges of engineering carriers for biomedical applications—a mini review." Frontiers in Chemistry 7 (2019): 258.
Ward H, Vigues S, Poole S, Bristow AF. The rat interleukin 10 receptor: cloning and sequencing of cDNA coding for the alpha-chain protein sequence, and demonstration by western blotting of expression in the rat brain. Cytokine. 2001;15(5):237-40.
Wawman, Rebecca Ellen, Helen Bartlett, and Ye Htun Oo. "Regulatory T cell metabolism in the hepatic microenvironment." Frontiers in immunology 8 (2018): 1889.
Weber et al., "White Paper on Adoptive Cell Therapy for Cancer with Tumor-Infiltrating Lymphocytes: A Report of the CTEP Subcommittee on Adoptive Cell Therapy," Clinical Cancer Research, vol. 17, No. 7, pp. 1664-1673, Apr. 1, 2011.
Weiss RA, Weiss MA, Beasley KL, Munavalli G (2007) Autologous cultured fibroblast injection for facial contour deformities: a prospective, placebo-controlled, Phase III clinical trial. Dermatol Surg 33(3): 263-268.
Widdel, F. 2010. "Theory and measurement of bacterial growth" http://www.mpi-bremen.de/Binaries/Binary13037/Wachstumsversuch.pdf.
Yamada, Noriko, et al. "Thermo-responsive polymeric surfaces; control of attachment and detachment of cultured cells." Die Makromolekulare Chemie, Rapid Communications 11.11 (1990): 571-576.
Yang, Hee Seok, et al. "Suspension culture of mammalian cells using thermosensitive microcarrier that allows cell detachment without proteolytic enzyme treatment." Cell transplantation 19.9 (2010): 1123-1132.
Yi, Zhuan, et al. "A readily modified polyethersulfone with amino-substituted groups: its amphiphilic copolymer synthesis and membrane application." Polymer 53.2 (2012): 350-358.
Yoshinari, Masao, et al. "Effect of cold plasma-surface modification on surface wettability and initial cell attachment." International Journal of Biomedical and Biological Engineering 3.10 (2009): 507-511.
Zappasodi et al., "The Effect Of Artificial Antigen-Presenting Cells with Preclustered Anit-CD28/-CD3/LFA-1 Monoclonal Antibodies on the Induction of ex vivo Expansion of Functional Human Antitumor T Cells," Haematologica, vol. 93, No. 10, pp. 1523-1534, 2008.
Zemmour D, Zilionis R, Kiner E, Klein AM, Mathis D, Benoist C. Publisher Correction: Single-cell gene expression reveals a landscape of regulatory T cell phenotypes shaped by the TCR. Nat Immunol. 2018;19(6):645.
Zeng B, Kwak-Kim J, Liu Y, Liao AH. Treg cells are negatively correlated with increased memory B cells in pre-eclampsia while maintaining suppressive function on autologous B-cell proliferation. Am J Reprod Immunol. 2013;70(6):454-63.
Zheng, et al at the University of Iowa have shown that the differential effects of pulsatile blood flow and cyclic stretch are an important growth stimulus (American Journal of Physiology—Heart and Circulatory Physiology, 2008).

* cited by examiner

CELL CAPTURE AND EXPANSION

CROSS-REFERENCE TO RELATED APPLICATIONS

The present application claims the benefit of and priority, under 35 U.S.C. § 119(e), to the following U.S. Provisional Patent Application Ser. Nos.: 63/165,060, filed on Mar. 23, 2021, entitled "Cell Expansion"; 63/169,173, filed on Mar. 31, 2021, entitled "Cell Expansion"; 63/183,591, filed on May 3, 2021, entitled "Cell Expansion"; 63/227,293, filed on Jul. 29, 2021, entitled "Cell Expansion"; 63/228,561, filed on Aug. 2, 2021, entitled "Cell Expansion"; 63/275,389, filed on Nov. 3, 2021, entitled "Methods and Systems for Isolating Target Cells Using a Multiple Part Membrane Substrate"; 63/275,793, filed on Nov. 4, 2021, entitled "Methods and Systems for Isolating Target Cells Using a Multiple Part Membrane Substrate"; 63/304,467, filed on Jan. 28, 2022, entitled "Methods and Systems for Isolating Target Cells Using a Multiple Part Membrane Substrate"; the entire disclosures of each are incorporated herein by reference, in their entirety.

BACKGROUND

The present disclosure is generally directed to isolating and expanding living cells, in particular, toward isolating target cells using a membrane and expanding the isolated cells.

Cell processing systems include Cell Collection Systems and Cell Expansion Systems (CES's). Cell Collection Systems collect cells from a supply source and CES's may be used to expand and differentiate a variety of cell types. Expanded and/or differentiated cells may be used for both research and/or therapeutic purposes. As one example, hematopoietic stem cells (HSC) possess multipotentiality, enabling them to self-renew and to produce mature blood cells, such as erythrocytes, leukocytes, platelets, and lymphocytes. CD34 is a marker of human HSC, and all colony-forming activity of human bone marrow (BM) cells is found in the fraction of cells expressing CD34 (i.e., "CD34+ HSCs" or "CD34+ cells" or "the CD34+ fraction"). HSC's may be collected from bone marrow, cord blood, or peripheral blood, and CD34+ HSCs have been identified as possible treatments for diseases such as hematological cancers (e.g., lymphoma, leukemia, myeloma). Umbilical cord blood (CB) is increasingly being used as an alternative to bone marrow (BM) as a source of transplantable CD34+ HSCs. Effective treatment with, or transplantation of, CD34+ HSCs requires the administration of a minimum number of HSC's. Accordingly, following isolation of CD34+ HSCs from a suitable source, such as CB, the CD34+ HSCs must be grown (i.e., "expanded") from an initial amount to at least an amount that may be considered effective for treatment or transplantation.

This disclosure provides procedures, devices, and compositions useful in the isolation, expansion, and administration of CD34+ HSCs.

SUMMARY

This summary is provided to introduce aspects of this disclosure in a simplified form, and is not intended to identify key or essential elements, nor is it intended to limit the scope of the claims.

This disclosure provides cell capture and expansion systems and methods of expanding target cells that may be collected from a mixed cell population. Examples include a membrane useful for trapping, collecting, and/or otherwise holding target cells, in particular CD34+ HSCs. Using the methods of this disclosure, the HSCs may be collected and significantly expanded quickly and efficiently while minimizing or eliminating differentiation of the HSCs. In the systems and methods of this disclosure, the HSCs may be expanded at least 50-fold. The cells may be target cells collected from a donor fluid (e.g., one or more blood components). These target cells may include, but are not limited to, stem cells, CD34+ HSCs, T-cells, natural killer (NK) cells, monocytes, or the like. The membrane may comprise one or more layers or coatings (i.e., a membrane) that are configured to attract and collect target cells. The membrane may comprise a substrate that promotes cellular adhesion to at least one surface of the substrate. The substrate may have a first surface and a second surface and at least one coating on the first surface and/or the second surface. The at least one coating may correspond to any molecule or material that promotes cellular adhesion to the first surface and/or the second surface of the substrate. The at least one coating may include a first coating material and a second coating material. The first coating material may be fibronectin, or a fibronectin equivalent, and the second coating material may be a soluble protein moiety. The second coating material may target specific target cells from a mixed cell population. For instance, the second coating material may be a chemokine, such as stromal cell-derived factor-1 (SDF-1), which may be used to enhance collection of CD34+ HSCs. Additional coating materials may be used to collect the same or different cells from a mixed cell population. The membrane may be arranged in any form, such as a flat sheet, a filter matrix, a hollow fiber, any combination thereof, and/or any plurality thereof.

This disclosure also provides methods for expanding cells, in particular CD34+ HSCs, in a bioreactor, such as a hollow fiber bioreactor. These methods provide for introducing cells (e.g., hematopoietic stem cells (HSC's), including, for example, CD34+ HSCs) into a bioreactor, and exposing the cells to growth conditions that expand the number of cells in the bioreactor. The growth conditions may include the introduction of one or a combination of growth factors into bioreactor. Alternatively or additionally, the growth conditions may include the presence of co-cultured cells in the bioreactor. After expanding the cells in the bioreactor, a plurality of expanded cells may then be removed from the bioreactor for storage, transplantation, or use in therapies such as cancer therapies.

This disclosure provides methods of expanding cells that include introducing a plurality of cells comprising CD34+ Hematopoietic stem cells (HSCs) into hollow fibers of a hollow fiber bioreactor. The hollow fibers of the bioreactor each comprise an interior lumen and an extracapillary side. Additionally, the hollow fibers comprise a coating on at least one of the lumen surface and the extracapillary surface. The coating on the surface(s) includes stromal cell-derived factor-1 (SDF-1) and fibronectin or isoforms, or functional equivalents thereof. In these methods, the plurality of cells in the hollow fibers are exposed to growth conditions and at least a portion of the plurality of cells is expanded in the hollow fibers of the bioreactor to generate a plurality of expanded CD34+ HSCs. Using these methods, the plurality of cells introduced into the hollow fibers of the bioreactor may be expanded at least 50-fold.

This disclosure also provides methods of expanding cells by perfusion in a cell expansion system. These methods include coating a hollow fiber bioreactor with a first fluid, which may include a signaling factor and/or a coating factor. In these methods, a plurality of cells is introduced into a hollow fiber membrane of a hollow fiber bioreactor. In these methods, the plurality of cells in the hollow fiber membrane may be exposed to a second fluid, which includes a plurality of growth factors. In these methods, the plurality of cells in the hollow fiber bioreactor may be grown in monoculture or in coculture.

This disclosure also provides methods of capturing cells that includes introducing a mixture of target cells and non-target cells into hollow fibers of a hollow fiber bioreactor. These hollow fibers each comprise an interior lumen and an extracapillary side, and a coating on at least one of the lumen surface and the extracapillary surface of the hollow fibers. The coating on the surface(s) includes stromal cell-derived factor-1 (SDF-1) and fibronectin or isoforms, or functional equivalents thereof. In these methods, the mixture of target and non-target cells in the hollow fibers may be exposed to capture conditions to capture at least a portion of the target cells on at least one of the lumen and the extracapillary surface of the hollow fibers. At least a portion of the non-target cells may be flushed from the hollow fibers, leaving target cells associated with a surface of the hollow fibers.

This disclosure also provides methods of capturing target species. In these methods, a mixture of target species and non-target species are introduced into hollow fibers, which have an interior lumen and an extracapillary side. These hollow fibers may include a coating on at least one of the lumen surface and the extracapillary surface of the hollow fibers. The coating may include at least one of streptavidin, avidin, a biotinylated molecule, and an anti-biotin antibody or a functional fragment thereof. In these methods, the mixture of target species and non-target species in the hollow fibers may be exposed to capture conditions to capture at least a portion of the target species on at least one of the lumen and the extracapillary surface(s) of the hollow fibers. In these methods, at least a portion of the non-target species may be flushed from the hollow fibers.

This disclosure also provides coated hollow fiber membranes. These membranes are hollow fiber membranes having a lumen surface and an extracapillary surface. These membranes may include a coating on at least one of the lumen surface and the extracapillary surface of the hollow fibers. The coating may include stromal cell-derived factor-1 (SDF-1) and fibronectin or isoforms, or functional equivalents thereof.

This disclosure also provides methods of forming a coated hollow fiber membrane that include providing a hollow fiber membrane having a lumen surface and an extracapillary surface and applying a first coating onto the lumen surface of the hollow fiber membrane. In these methods, the first coating comprises a material that promotes cellular adhesion to at least one of the lumen of the hollow fiber membrane and the extracapillary surface of the hollow fiber membrane. In these methods, a second coating may be applied onto the lumen surface of the hollow fiber membrane. The second coating may include a soluble protein moiety.

This disclosure also provides compositions useful for expanding CD34+ HSCs. These compositions include glial cell-derived neurotrophic factor (GDNF) and an aryl hydrocarbon receptor (AHR) antagonist.

The preceding is intended to provide a simplified summary of some aspects of the disclosure. This summary is neither an extensive nor exhaustive overview of the disclosure and its various aspects, implementations, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, implementations, and configurations of the disclosure are possible utilizing, alone or in combination, one or more of the features set forth above or described in detail below, and will be apparent to those skilled in the art upon consideration of the following Detailed Description and in view of the Figures.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples.

DETAILED DESCRIPTION

Figure 1:
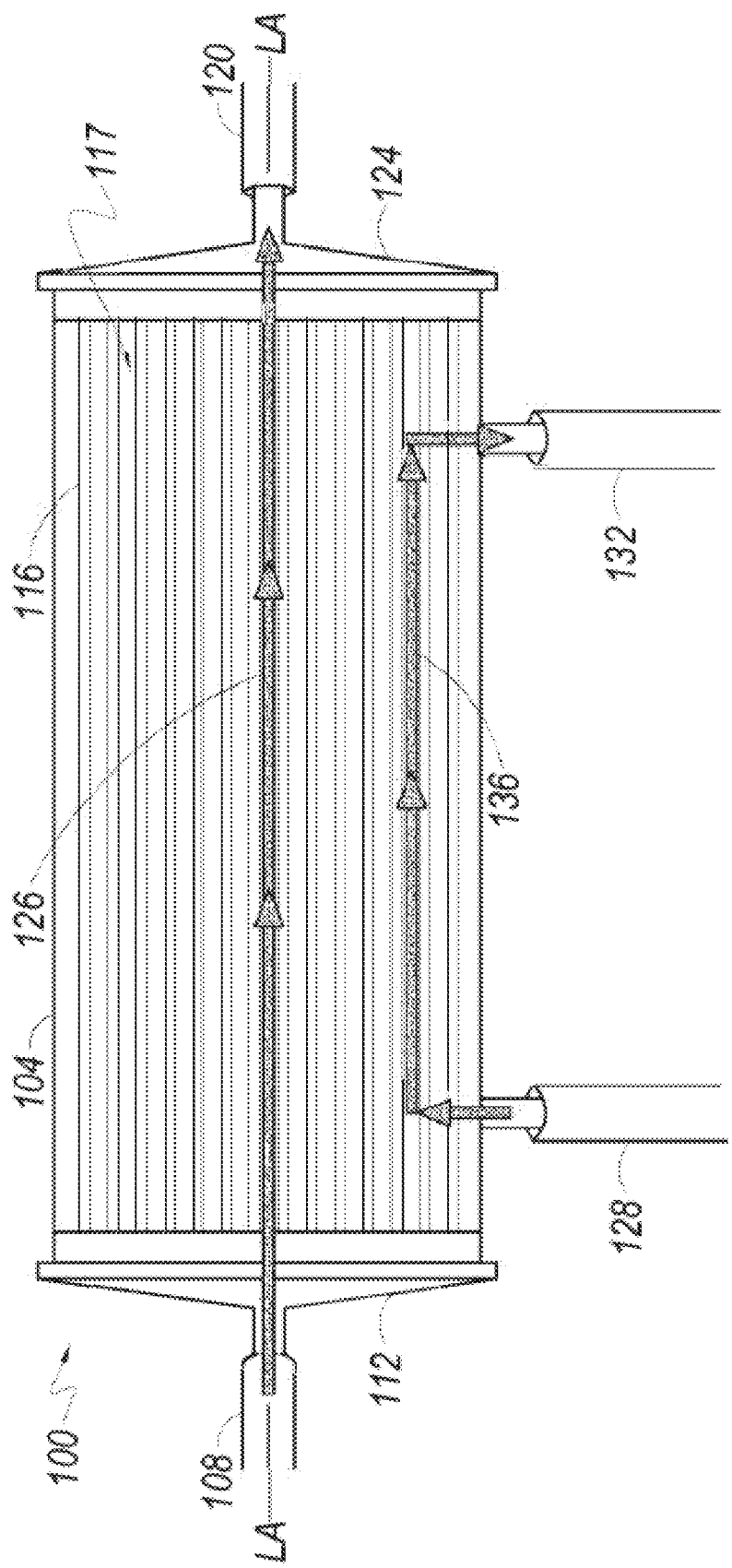
FIG. 1 depicts a perspective view of a hollow fiber bioreactor, in accordance with implementations.

The principles of the present disclosure may be further understood by reference to the following detailed description and the implementations depicted in the accompanying drawings. It should be understood that although specific features are shown and described below with respect to detailed implementations, the present disclosure is not limited to the implementations described below.

Reference will now be made in detail to the implementations illustrated in the accompanying drawings and described below. Wherever possible, the same reference numerals are used in the drawings and the description to refer to the same or like parts.

Referring to FIG. 1, an example of a hollow fiber bioreactor 100, which may be used with the present disclosure is shown in front side elevation view. Hollow fiber bioreactor 100 has a longitudinal axis LA-LA and includes chamber housing 104. In at least one implementation, chamber housing 104 includes four openings or ports: intracapillary (IC) inlet port 108, IC outlet port 120, extracapillary (EC) inlet port 128, and EC outlet port 132.

According to implementations of the present disclosure, fluid in a first circulation path enters hollow fiber bioreactor 100 through IC inlet port 108 at a first longitudinal end 112 of the hollow fiber bioreactor 100, passes into and through the intracapillary side (referred to in various implementations as the lumen, intracapillary ("IC") side, or "IC space" of a hollow fiber membrane) of a plurality of hollow fibers 116, and out of hollow fiber bioreactor 100 through IC outlet port 120 located at a second longitudinal end 124 of the hollow fiber bioreactor 100. The fluid path between the IC inlet port 108 and the IC outlet port 120 defines the IC portion 126 of the hollow fiber bioreactor 100. Fluid in a second circulation path flows in the hollow fiber bioreactor 100 through EC inlet port 128, comes in contact with the extracapillary side or outside (referred to as the "EC side" or "EC space" of the membrane) of the hollow fibers 116, and exits hollow fiber bioreactor 100 via EC outlet port 132. The fluid path between the EC inlet port 128 and the EC outlet port 132 comprises the EC portion 136 of the hollow fiber bioreactor 100. Fluid entering hollow fiber bioreactor 100 via the EC inlet port 128 may be in contact with the outside of the hollow fibers 116. Small molecules (e.g., ions, water, oxygen, lactate) may diffuse through the hollow fibers 116 from the interior or IC space of the hollow fiber to the exterior or EC space, or from the EC space to the IC space. Large molecular weight molecules, such as growth factors, may be too large to pass through the hollow fiber membrane, and remain in the IC space of the hollow fibers 116. The media may be replaced as needed, in implementations. Media may also be circulated through an oxygenator or gas transfer module to exchange gasses as needed (see e.g., cell expansion systems 500 (FIG. 5) and 600 (FIG. 6)). Cells may be contained within a first circulation path and/or a second circulation path, as described below, and may be on either the IC side and/or EC side of the membrane, according to implementations.

The material used to make the hollow fiber membrane may be any biocompatible polymeric material which is capable of being made into hollow fibers and which possesses suitable permeability to small molecules such as, for example, ions, water, oxygen, glucose and lactate. One material which may be used is a synthetic polysulfone-based material, according to an implementation of the present disclosure. For the cells to adhere to the surface of the hollow fibers, the surface may be modified in some way, either by coating at least the cell growth surface with a protein, e.g., a glycoprotein such as fibronectin or collagen, or by exposing the surface to radiation. Gamma treating the membrane surface may allow for attachment of adherent cells without additionally coating the membrane with fibronectin or the like. Other coatings and/or treatments for cell attachment may be used in accordance with implementations of the present disclosure.

Figure 2:
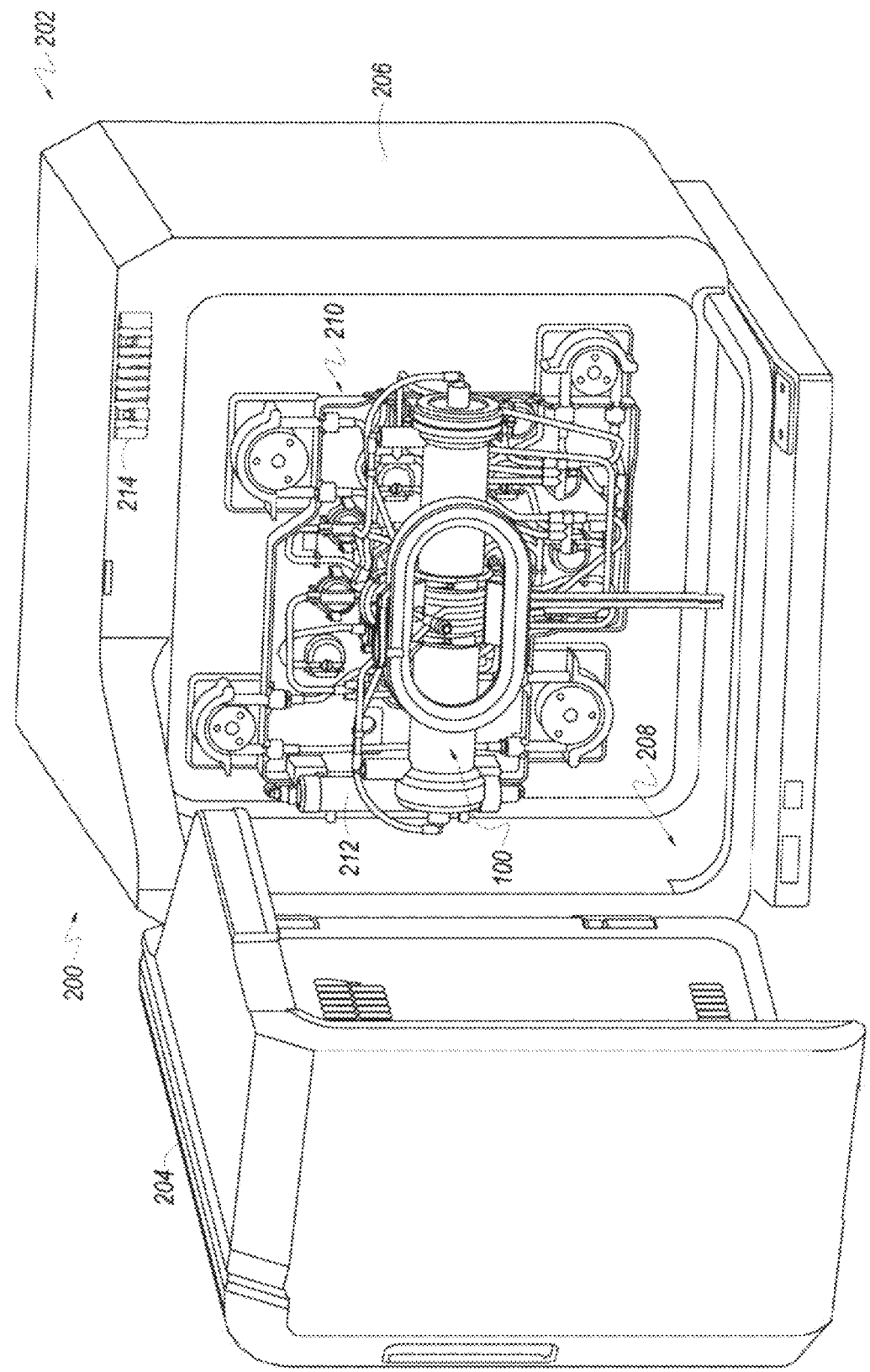
FIG. 2 illustrates a perspective view of a cell expansion system with a premounted fluid conveyance device, in accordance with implementations.

Turning to FIG. 2, an implementation of a cell expansion system 200 with a premounted fluid conveyance assembly is shown in accordance with implementations of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly 210 that includes a bioreactor 100. The premounted fluid conveyance assembly 210 may be detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. A single cell expansion machine 202 may be operated to grow or expand a first set of cells using a first premounted fluid conveyance assembly 210 and, thereafter, may be used to grow or expand a second set of cells using a second premounted fluid conveyance assembly 210 without needing to be sanitized between interchanging the first premounted fluid conveyance assembly 210 for the second premounted fluid conveyance assembly 210. The premounted fluid conveyance assembly includes a bioreactor 100 and an oxygenator or gas transfer module 212. Tubing guide slots are shown as 214 for receiving various media tubing connected to premounted fluid conveyance assembly 210, according to implementations.

Figure 3:
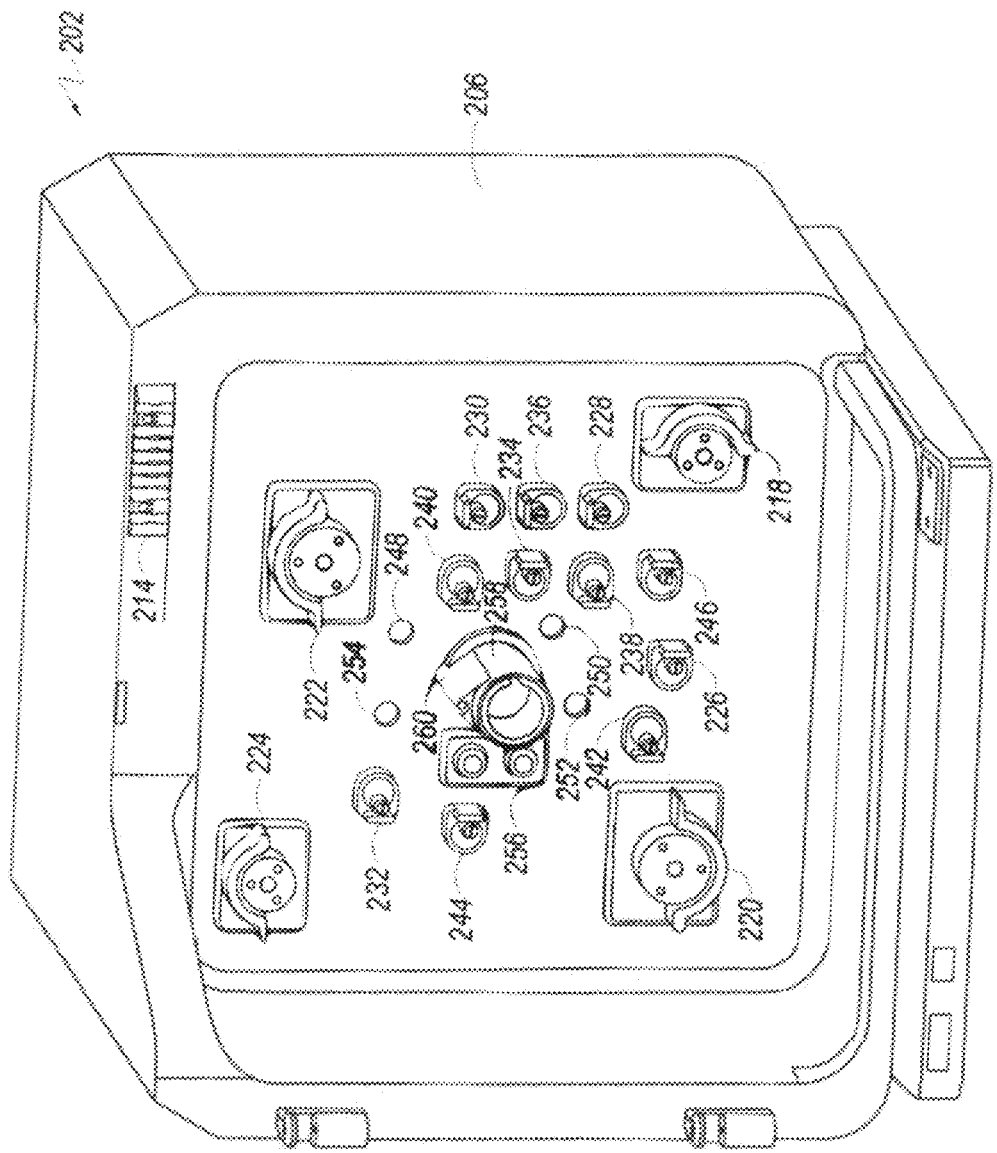
FIG. 3 depicts a perspective view of a housing of a cell expansion system, in accordance with implementations.

Next, FIG. 3 illustrates the back portion 206 of cell expansion machine 202 prior to detachably-attaching a premounted fluid conveyance assembly 210 (FIG. 2), in accordance with implementations of the present disclosure. The closable door 204 (shown in FIG. 2) is omitted from FIG. 3. The back portion 206 of the cell expansion machine 202 includes a number of different structures for working in combination with elements of a premounted fluid conveyance assembly 210. More particularly, the back portion 206 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste valve 242, the EC waste valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber.

In accordance with implementations, a shaft or rocker control 258 for rotating the bioreactor 100 is shown in FIG. 3. Shaft fitting 260 associated with the shaft or rocker control 258 allows for proper alignment of a shaft access aperture, see e.g., 424 (FIG. 4) of a tubing-organizer, see e.g., 300 (FIG. 4) of a premounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused premounted fluid conveyance assembly 400 (FIG. 4) to the cell expansion machine 202, the alignment is a relatively simple matter of properly orienting the shaft access aperture 424 (FIG. 4) of the premounted fluid conveyance assembly 400 with the shaft fitting 260.

Figure 4:
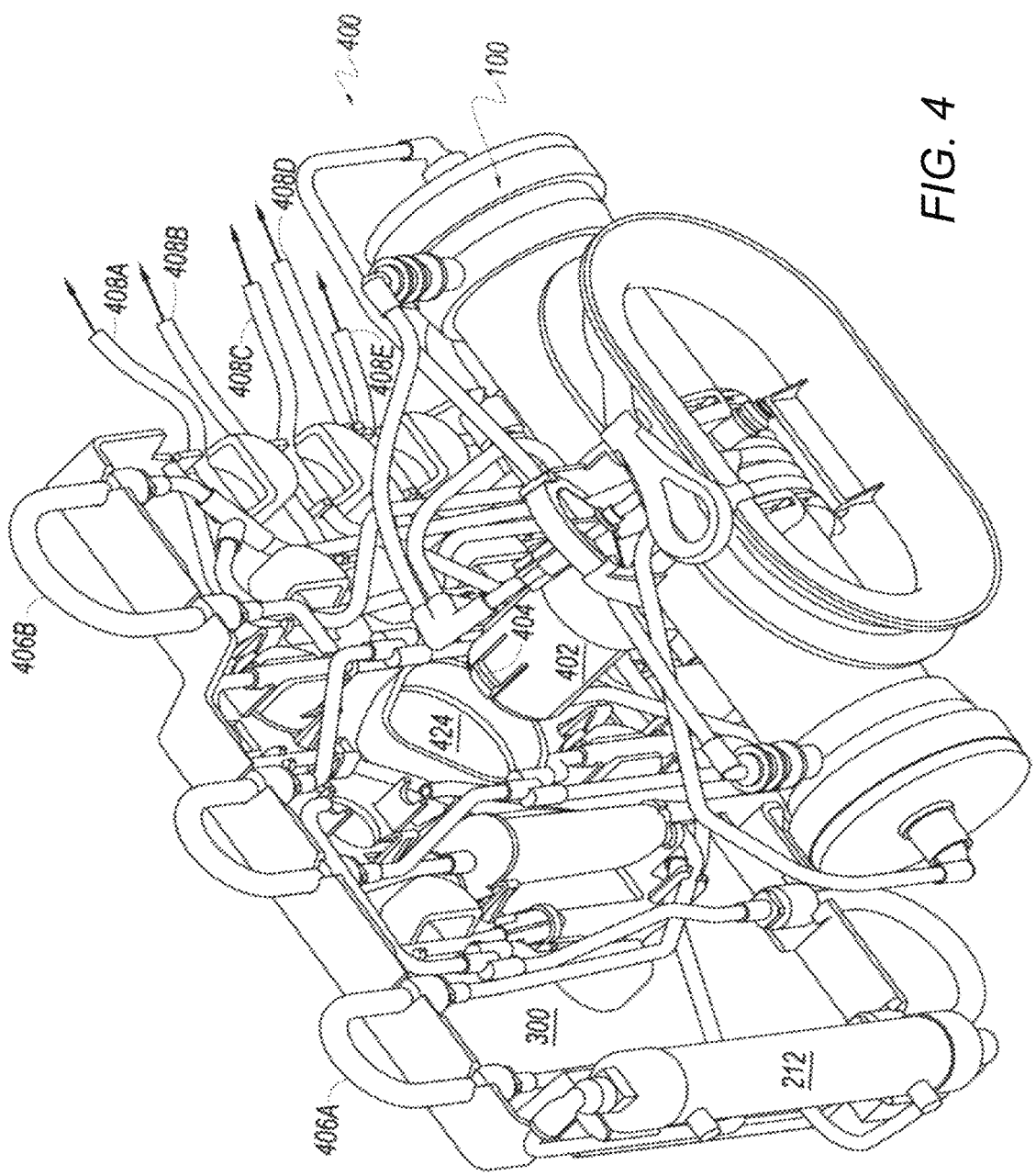
FIG. 4 illustrates a perspective view of a premounted fluid conveyance device, in accordance with implementations.

Turning to FIG. 4, a perspective view of a detachably-attachable premounted fluid conveyance assembly 400 is shown. The premounted fluid conveyance assembly 400 may be detachably-attachable to the cell expansion machine 202 to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

In implementations, the shaft fitting 402 and the spring member 404 connect to mechanisms of a cell expansion system that rotate the bioreactor 100. For example, in some implementations, the cell expansion system may be part of a QUANTUM® Cell Expansion System (CES), manufactured by Terumo BCT, Inc. of Lakewood, Colo., which provides for rotation of a bioreactor. Examples of cell expansion systems that provide for rotation of the bioreactor are described in at least: U.S. Pat. No. 8,399,245, issued Mar. 19, 2013, entitled "ROTATION SYSTEM FOR CELL GROWTH CHAMBER OF A CELL EXPANSION SYSTEM AND METHOD OF USE THEREFOR;" U.S. Pat. No. 8,809,043, issued Feb. 13, 2013, entitled "ROTATION SYSTEM FOR CELL GROWTH CHAMBER OF A CELL EXPANSION SYSTEM AND METHOD OF USE THEREFOR;" and U.S. Pat. No. 9,057,045, issued Jun. 16, 2015, entitled "METHOD OF LOADING AND DISTRIBUTING CELLS IN A BIOREACTOR OF A CELL EXPANSION SYSTEM;" all three of which are hereby incorporated by reference in their entirety as if set forth herein in full.

According to implementations, the premounted fluid conveyance assembly 400 includes tubing 408A, 408B, 408C, 408D, 408E, and various tubing fittings to provide the fluid paths shown in FIGS. 5 and 6, as discussed below. Pump loops 406A and 406B are also provided for the pump(s). In implementations, although the various media may be provided at the site where the cell expansion machine 202 is located, the premounted fluid conveyance assembly 400 may include sufficient tubing length to extend to the exterior of the cell expansion machine 202 and to enable welded connections to tubing associated with the media bags, according to implementations.

Figure 5:
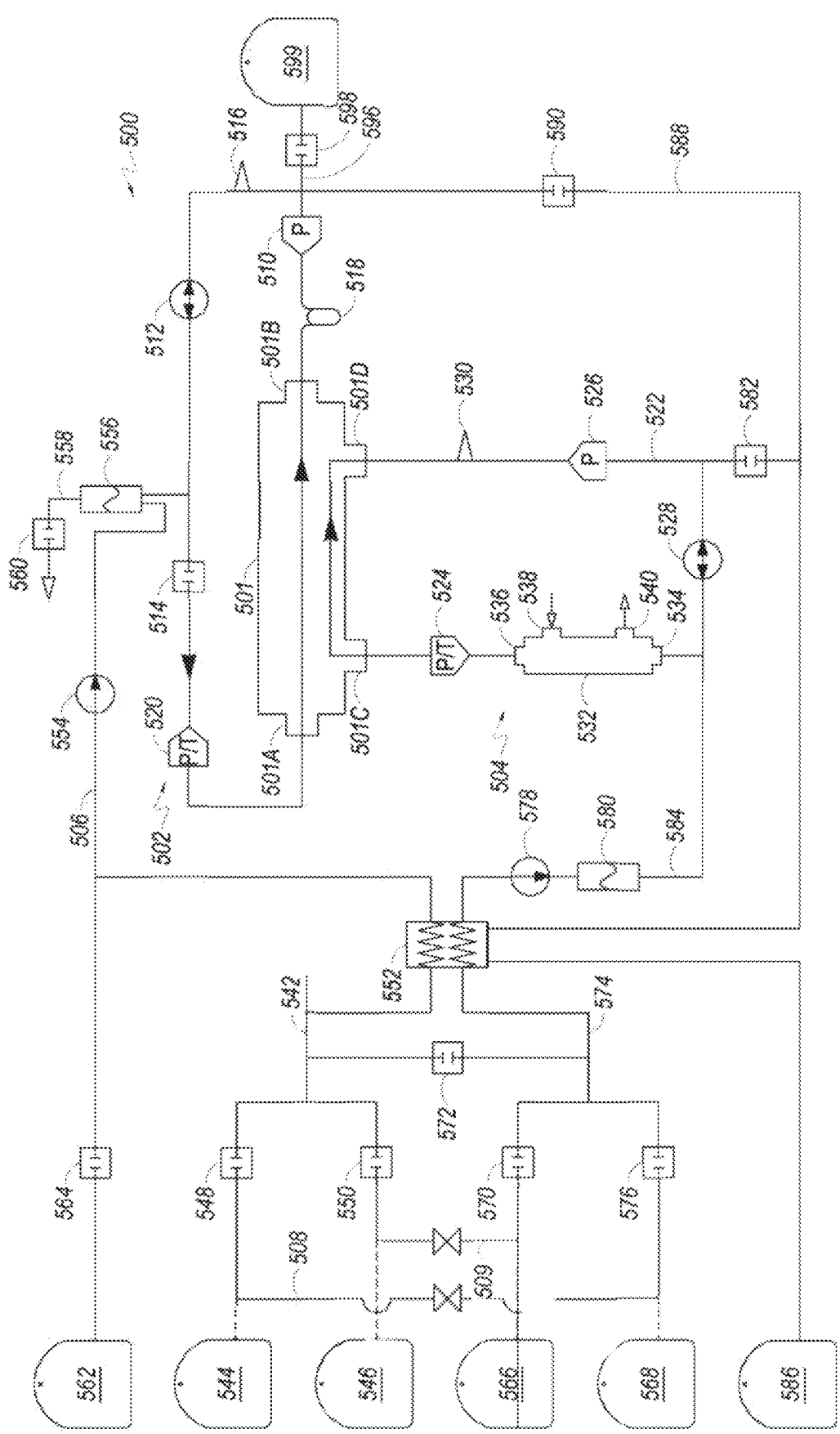
FIG. 5 depicts a schematic of a cell expansion system, in accordance with implementations.
Figure 6:
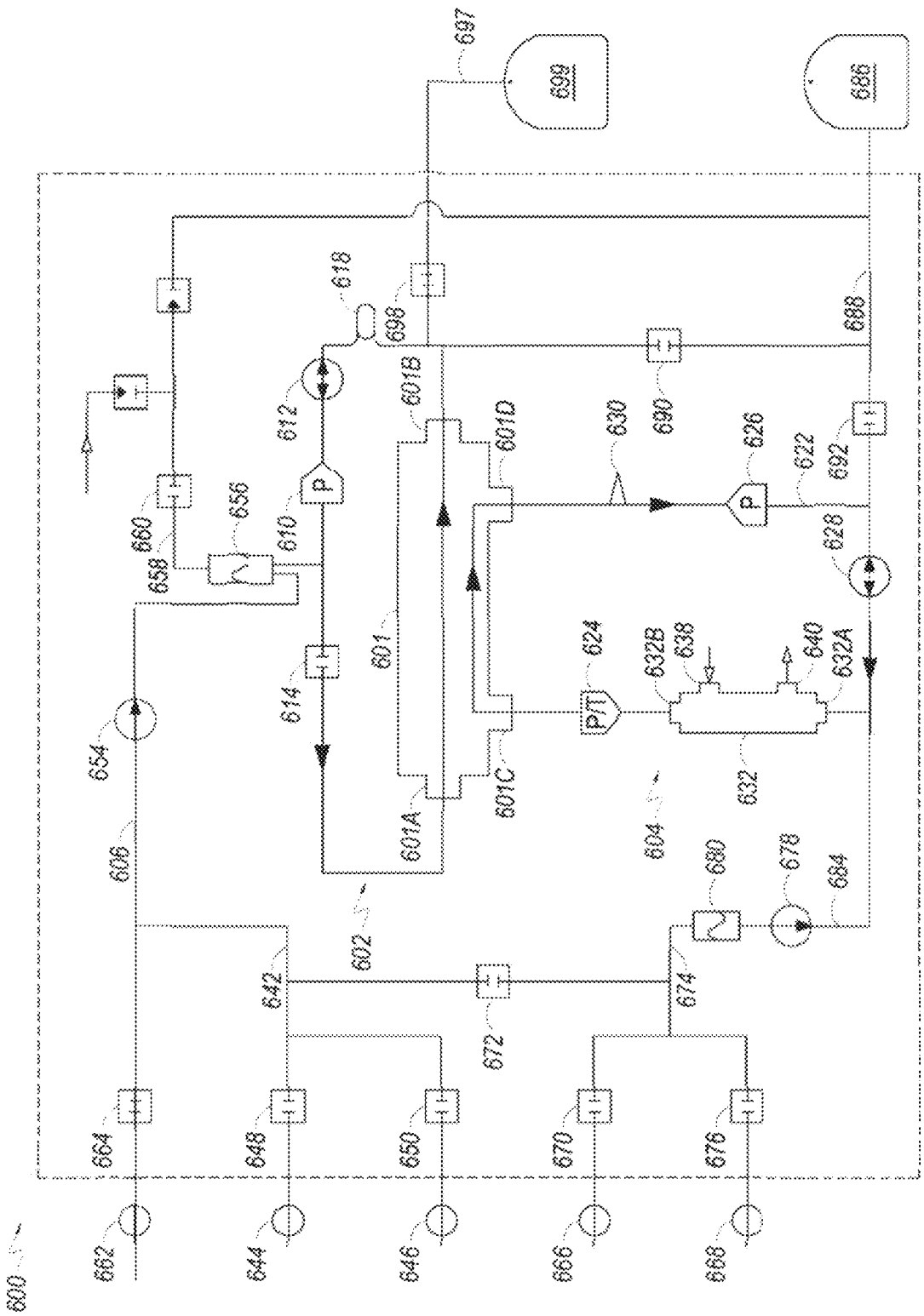
FIG. 6 illustrates a schematic of another implementation of a cell expansion system, in accordance with implementations.

FIG. 5 illustrates a schematic of an implementation of a cell expansion system 500, and FIG. 6 illustrates a schematic of another implementation of a cell expansion system 600. In the implementations shown in FIGS. 5 and 6, and as described below, the cells are grown in the IC space and may in other implementations provide for cells to be grown in the EC space. In yet other implementations, such as when co-culturing cells, first cells may be grown in the EC space, while second cells may be grown in the IC space. Co-culturing of cells may also be performed by growing first cells and second cells in the EC space, or growing first cells and second cells in the IC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to implementations. First fluid flow path 506 may be fluidly associated with hollow fiber bioreactor 501 to form, at least in part, first fluid circulation path 502. Fluid flows into hollow fiber bioreactor 501 through IC inlet port 501A, through hollow fibers in hollow fiber bioreactor 501, and exits via IC outlet port 501B. Pressure gauge 510 measures the pressure of media leaving hollow fiber bioreactor 501. Media flows through IC circulation pump 512 which may be used to control the rate of media flow/rate of fluid circulation. IC circulation pump 512 may pump the fluid in a first direction (e.g., clockwise) or second direction opposite the first direction (e.g., counter clockwise). Exit port 501B may be used as an inlet in the reverse direction. Media entering the IC loop 502 may then enter through valve 514. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present implementations.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in hollow fiber bioreactor 501 may be flushed out of hollow fiber bioreactor 501 into harvest bag 599 through valve 598 or redistributed within the hollow fibers for further growth.

Fluid in second fluid circulation path 504 enters hollow fiber bioreactor 501 via EC inlet port 501C, and leaves hollow fiber bioreactor 501 via EC outlet port 501D. Media in the EC loop 504 may be in contact with the outside of the hollow fibers in the hollow fiber bioreactor 501, thereby allowing diffusion of small molecules into and out of the hollow fibers.

Pressure/temperature gauge 524 disposed in the second fluid circulation path 504 allows the pressure and temperature of media to be measured before the media enters the EC space of hollow fiber bioreactor 501. Pressure gauge 526 allows the pressure of media in the second fluid circulation path 504 to be measured after it leaves hollow fiber bioreactor 501. With regard to the EC loop, samples of media may be obtained from sample port 530 or a sample coil during operation.

In implementations, after leaving EC outlet port 501D of hollow fiber bioreactor 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to and removes both carbon dioxide and bubbles from media in the CES 500. In various implementations, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through hollow fiber bioreactor 501 in the same direction (a co-current configuration). The CES 500 may also be configured to flow in a counter-current configuration.

In accordance with at least one implementation, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 548, 550, and 570. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Implementations provide for the use of numerous other types of sensors without departing from the spirit and scope of the present disclosure. For example, optical sensors may be used in accordance with implementations of the present disclosure. Air or gas purged from the CES 500 during portions of the priming sequence or other protocols may vent to the atmosphere out air valve 560 via line 558 that may be fluidly associated with air removal chamber 556.

EC media (from bag 568) or wash solution (from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing valve distribution 572. An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one implementation, first and second fluid circulation paths 502 and 504 are connected to waste line 588. When valve 590 is opened, IC media may flow through waste line 588 and to waste or outlet bag 586. Likewise, when valve 582 is opened, EC media may flow through waste line 588 to waste or outlet bag 586.

In implementations, cells may be harvested via cell harvest path 596. Here, cells from hollow fiber bioreactor 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media at a predetermined temperature.

Turning to FIG. 6, a schematic of another implementation of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with hollow fiber bioreactor 601 to form first fluid circulation path 602. Fluid flows into hollow fiber bioreactor 601 through IC inlet port 601A, through hollow fibers in hollow fiber bioreactor 601, and exits via IC outlet port 601B. Pressure sensor 610 measures the pressure of media leaving hollow fiber bioreactor 601. In addition to pressure, sensor 610 may, in implementations, also be a temperature sensor that detects the media pressure and temperature during operation.

Media flows through IC circulation pump 612 which may be used to control the rate of media flow or rate of circulation. IC circulation pump 612 may pump the fluid in a first direction (e.g. counter clockwise) or second direction opposite the first direction (e.g., clockwise). Exit port 601B may be used as an inlet in the reverse direction. Media entering the IC loop may flow through valve 614. As those skilled in the art will appreciate, additional valves and/or other devices may be placed at various locations to isolate and/or measure characteristics of the media along portions of the fluid paths. Samples of media may be obtained from sample coil 618 during operation. Media then returns to IC inlet port 601A to complete fluid circulation path 602.

Cells grown/expanded in hollow fiber bioreactor 601 may be flushed out of hollow fiber bioreactor 601 into harvest bag 699 through valve 698 and line 697. Alternatively, when valve 698 is closed, the cells may be redistributed within hollow fiber bioreactor 601 for further growth. It is to be understood that the schematic shown represents one possible configuration for various elements of the CES 600, and modifications to the schematic shown are within the scope of the one or more present implementations.

Fluid in second fluid circulation path 604 enters hollow fiber bioreactor 601 via EC inlet port 601C and leaves hollow fiber bioreactor 601 via EC outlet port 601D. Media in the EC loop may be in contact with the outside of the hollow fibers in the hollow fiber bioreactor 601, thereby allowing diffusion of small molecules into and out of the hollow fibers that may be within chamber 601, according to an implementation.

Pressure/temperature sensor 624 disposed in the second fluid circulation path 604 allows the pressure and temperature of media to be measured before the media enters the EC space of the hollow fiber bioreactor 601. Sensor 626 allows the pressure and/or temperature of media in the second fluid circulation path 604 to be measured after it leaves the hollow fiber bioreactor 601. With regard to the EC loop, samples of media may be obtained from sample port 630 or a sample coil during operation.

After leaving EC outlet port 601D of hollow fiber bioreactor 601, fluid in second fluid circulation path 604 passes through EC circulation pump 628 to oxygenator or gas transfer module 632. EC circulation pump 628 may also pump the fluid in opposing directions, according to implementations. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to and removes both carbon dioxide and bubbles from media in the CES 600.

In various implementations, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through hollow fiber bioreactor 601 in the same direction (a co-current configuration). The CES 600 may also be configured to flow in a counter-current configuration.

In accordance with at least one implementation, media, including cells (from a source such as a cell container, e.g. a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Implementations provide for the use of numerous other types of sensors without departing from the spirit and scope of the present disclosure. For example, optical sensors may be used in accordance with implementations of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one implementation, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 686.

After cells have been grown in hollow fiber bioreactor 601, they may be harvested via cell harvest path 697. Here, cells from hollow fiber bioreactor 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media at a predetermined temperature. It is further noted that, in implementations, components of CES 600 and CES 500 (FIG. 5) may be combined. In other implementations, a CES may include fewer or additional components than those shown in FIGS. 5 and 6 and still be within the scope of the present disclosure. In implementations, portions of CES 500 and 600 may be implemented by one or more features of the QUANTUM® Cell Expansion System (CES), manufactured by Terumo BCT, Inc. of Lakewood, Colo.

In one specific implementation of using CES 600, hematopoietic stem cells (HSC's), e.g., CD34+ HSCs, may be expanded in an implementation of CES 600. In this implementation, HSC's (including CD34+ HSCs), which may be collected using a leukapheresis process or a manual process (e.g., umbilical cords), may be introduced into the bioreactor 601. The HSC's (including CD34+ HSCs) may be introduced into the bioreactor 601 through path 602.

In some implementations, the HSC's (including CD34+ HSCs) may be subjected to a selection process (e.g., a purification process) before introduction into bioreactor 601. The process may involve the use of a centrifuge, purification column, magnetic selection, or chemical selection. Some examples of cell selection/purification procedures include use of isolation columns from, for example, Miltenyi Biotec of Bergisch Gladbach, Germany. In one example, cord blood is first subjected to a cell selection process that selects for HSC's (including CD34+ HSCs) before the cells are introduced into the bioreactor 601. Other examples may utilize apheresis machines to deplete other cells that may be included with the HSC's (including CD34+ HSCs) when originally collected. For example, the HSC's may be sourced from cord blood, bone marrow, or peripheral blood. After initial collection, but before being introduced into the bioreactor 601, a volume of HSC's including CD34+ HSCs may be processed to deplete red blood cells, specific leukocytes, granulocytes, and/or other cells from the volume. These are merely some examples, and implementations of the present invention are not limited thereto.

In other implementations, the HSC's (including CD34+ HSCs) may be added directly to the bioreactor 601 after collection without any additional purification. For example, cord blood (with HSC's) may be added to the bioreactor. In addition to a number of proteins and other bioactive molecules, the cord blood may include HSC's (including CD34+ HSCs), red blood cells, platelets, granulocytes, and/or leukocytes.

It is noted that in some implementations, the HSC's may be added to bioreactor 601, after a priming step. As may be appreciated, the cells being expanded may not be adherent and therefore it may not be required that they adhere to the hollow fiber walls of bioreactor 601 for expansion/proliferation. In these implementations, it may be unnecessary to coat the inside of the hollow fibers with a coating to promote adhesion, e.g., fibronectin. In these implementations, the HSC's (including CD34+ HSCs) (purified or unpurified) may be introduced into the bioreactor 601 after a priming step and without a bioreactor coating step. If the cells were adherent cells, a coating step may be performed after the priming step and before introduction of the HSC's.

Once in the bioreactor 601, the cells may be exposed to growth factors, activators, hormones, reagents, proteins, and/or other bioactive molecules that may aid in the expansion of the cells. In one example, a co-culture cell line may have been previously grown/introduced, in the bioreactor 601, to optimize the conditions for growing the HSC's (including CD34+ HSCs). In one specific implementation, human mesenchymal stem cells (hMSC's) may be co-cultured with the HSC's (including CD34+ HSCs) to promote growth of CD34+ HSCs. Without being bound by theory, it is believed that MSC's may emit factors (e.g., SDF-1 factors) that interact with HSC's (e.g., CD34+ HSCs) and promote proliferation of these cells. In some implementations, use of the co-cultured hMSC's may involve a growing process that is performed initially, under conditions optimized for proliferating the hMSC's, before the HSC's (including CD34+ HSCs) are introduced into the bioreactor 601. The hMSC's may be derived in implementations from bone marrow, peripheral blood, cord cells, adipose tissue, and/or molar tissue.

In addition to co-culture cells, a supplement including one or more growth factors, activators, hormones, reagents, proteins, and/or other bioactive molecules may be added to bioreactor 601 to grow and expand the HSC's. The supplement may be added as a single volume addition or over a period of time (e.g., continuously, intermittently, or on a regular schedule). In one implementation, a combination of cytokines and/or other proteins, e.g., recombinant cytokines, hormones, may be included as part of the supplement. As one example, a supplement may include one or more of: recombinant human Flt3 ligand (rhFlt-3L), recombinant human stem cell factor (rhSCF), recombinant human thrombopoietin (rhTPO), recombinant human (rh) Glial-derived neurotrophic factors and/or combinations thereof. One example of a supplement that may be used with implementations is STEMCELL2MAX™ supplement (stemcell2MAX, Cantanhede, Portugal).

It is noted that in some implementations, the combination of factors may be included in the media in which the cells are suspended. For example, the HSC's may be suspended in media and introduced 1406 into the bioreactor in the media. In implementations, the media may include a combination of growth factors that aid in proliferation of the HSC's.

After the cells have been introduced into the bioreactor with the supplement, co-culture cells, and/or other material for expanding the cells, the cells are allowed to expand in bioreactor 1410. During the expansion, there may be materials that may be added or removed from bioreactor. As one example, additional proteins (e.g., cytokines) may be added to bioreactor 601. In some implementations, more than one protein or other bioactive agent may be used. The additional material may be added individually, at the same time, at different times, or may be combined and added in combination.

It is noted that some implementations may provide for adding material more directly into the bioreactor 501, such as through port 516 (FIG. 5). In other implementations, however, the materials may be added in a location, e.g., through path 606, so that the materials may be perfused more slowly into bioreactor 601.

In addition to materials for aiding in growing the HSC's (including CD34+ HSCs), the HSC's may also be fed, such as by addition of a media that may include a number of nutrients. In some implementations, the media may be commercially available media that may include serum. In other implementations, the media may be serum free and include other additives. The media may be modified by the addition of other materials, some non-limiting examples including salts, serum, proteins, reagents, bioactive molecules, nutrients. One example of media that may be used to feed the HSC's (including CD34+ HSCs) includes CELL-GRO® serum free media (CellGenix, Freiburg, Germany).

In some implementations, while the co-culture cells are located in the IC space, feeding may occur in the EC space. Feeding through the EC space may, in implementations, reduce the amount of force that may be felt by the cells from circulating fluid in the IC space. Circulation of media in the EC space may, in implementations, provide sufficient nutrients for the expansion of the HSC's (including CD34+ HSCs).

As part of the expansion of the HSC's (including CD34+ HSCs), other conditions such as temperature, pH, oxygen concentration, carbon dioxide concentration, waste concentration, metabolite concentration may also be controlled in bioreactor 601. In some implementations, the flow rates of the EC side, e.g., path 604 may be used to control various parameters. For example, if it is desired to reduce waste or metabolite concentrations on the IC side, where the cells are growing, flow rate on the EC side may be increased to ensure that the waste and/or metabolites are removed from the IC side by migration through the hollow fibers from the IC side to the EC side.

After the CD34+ HSCs have been expanded, the cells may be removed from the bioreactor 601. The CD34+ HSCs may be collected in container 699. In implementations, the collected CD34+ HSCs may be administered to a patient to reestablish hematopoiesis. Some non-limiting examples including patients undergoing treatment for various cancers, e.g., leukemia, myelodysplasia, non-Hodgkin lymphoma, which may effect hematopoiesis. The cells may be administered with other compounds or molecules.

In some implementations, use of CES 600 may provide advantages in growing HSC's (including CD34+ HSCs) over conventional processes. For example, the use of hollow fibers allows close cell to cell communication, which may enhance the growth of the CD34+ HSCs to start and continue to proliferate. Also, the use of a hollow fiber bioreactor, such as bioreactor 601, may provide a large surface area for cell growth, which may yield a higher concentration or higher volume of CD34+ HSCs.

Further, the conditions in bioreactor 601 may be controlled using a number of different components of the CES 600, including IC flow rates and EC flow rates. Also, CES 600 provides various locations for the addition of materials, which allows more direct, or indirect, e.g., perfusion, of cytokines into bioreactor 601.

Additionally, CES 600 provides a closed system. That is, the steps for growing the CD34+ HSCs may be performed without direct exposure to the ambient environment, which may contaminate the cells, or be contaminated by the cells or materials used in growing the cells. It is also believed that some implementations may provide for using a smaller starting concentration of CD34+ HSCs for expansion, compared to other methods/systems. In these implementations, CD34+ HSCs may also be expanded to yield larger amounts than from other methods/systems. It is also believed that some implementations may provide for shortening the time for growing an effective dose of CD34+ HSCs.

Figure 7:
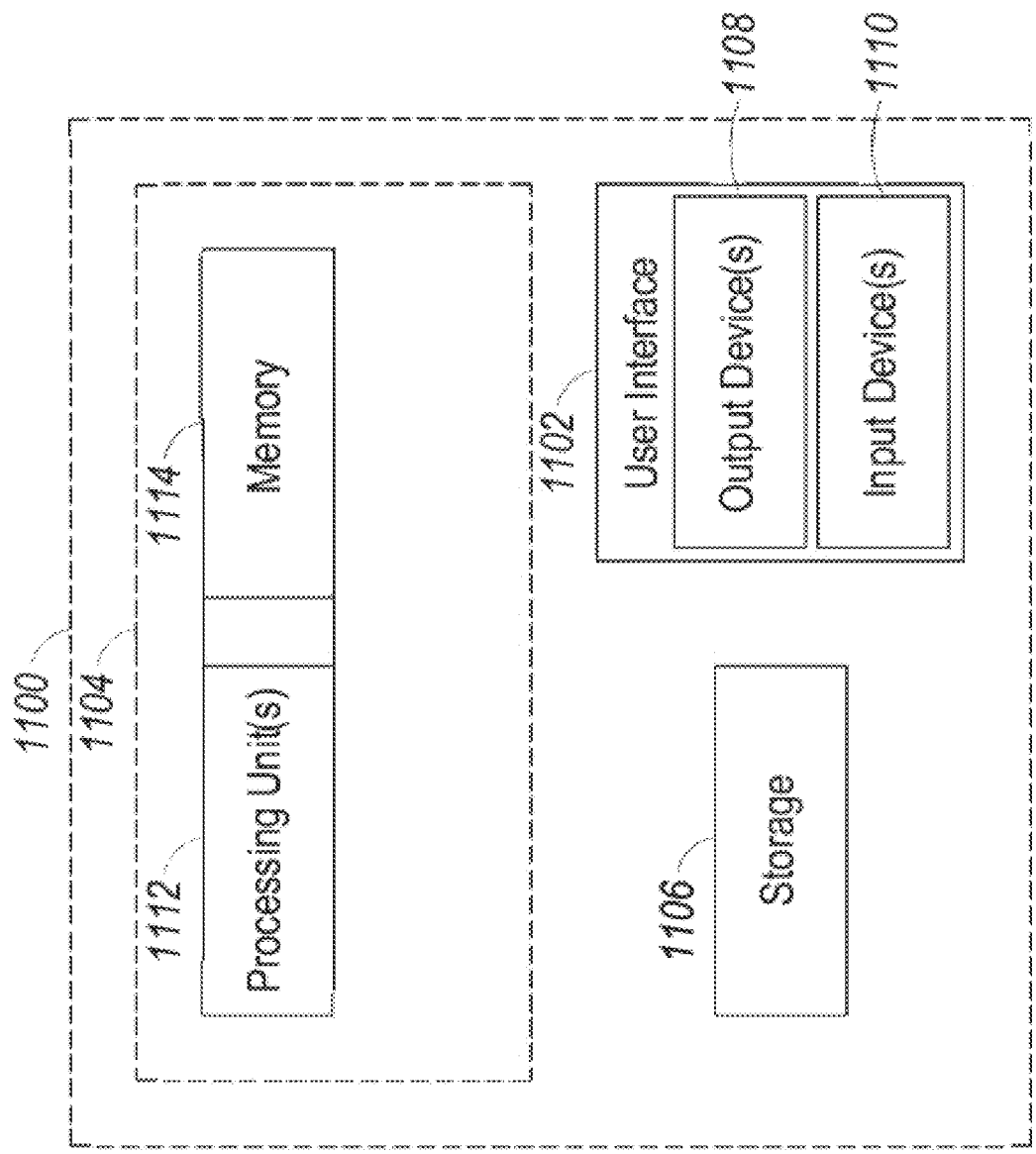
FIG. 7 illustrates components of a computing system that may be used to implement implementations.

FIG. 7 illustrates example components of a computing system 1100 upon which implementations of the present disclosure may be implemented. Computing system 1100 may be used in implementations, for example, where a cell expansion system uses a processor to execute tasks, such as custom tasks or pre-programmed tasks performed as part of processes, such as the process described above.

The computing system 1100 may include a user interface 1102, a processing system 1104, and/or storage 1106. The user interface 1102 may include output device(s) 1108, and/or input device(s) 1110 as understood by a person of skill in the art. Output device(s) 1108 may include one or more touch screens, in which the touch screen may comprise a display area for providing one or more application windows. The touch screen may also be an input device 1110 that may receive and/or capture physical touch events from a user or operator, for example. The touch screen may comprise a liquid crystal display (LCD) having a capacitance structure that allows the processing system 1104 to deduce the location(s) of touch event(s), as understood by those of skill in the art. The processing system 1104 may then map the location of touch events to user interface (UI) elements rendered in predetermined locations of an application window. The touch screen may also receive touch events through one or more other electronic structures, according to implementations. Other output devices 1108 may include a printer, speaker. Other input devices 1110 may include a keyboard, other touch input devices, mouse, voice input device, as understood by a person of skill in the art.

Processing system 1104 may include a processing unit 1112 and/or a memory 1114, according to implementations of the present disclosure. The processing unit 1112 may be a general purpose processor operable to execute instructions stored in memory 1114. Processing unit 1112 may include a single processor or multiple processors, according to implementations. Further, in implementations, each processor may be a multi-core processor having one or more cores to read and execute separate instructions. The processors may include general purpose processors, application specific integrated circuits (ASICs), field programmable gate arrays (FPGAs), other integrated circuits, as understood by a person of skill in the art.

The memory 1114 may include any short-term or long-term storage for data and/or processor executable instructions, according to implementations. The memory 1114 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, as understood by a person of skill in the art.

Storage 1106 may be any long-term data storage device or component. Storage 1106 may include one or more of the systems described in conjunction with the memory 1114, according to implementations. The storage 1106 may be permanent or removable. In implementations, storage 806 stores data generated or provided by the processing system 104.

This disclosure provides methods of expanding cells (i.e., increasing the number of cells grown in culture). In particular, these methods are useful in the expansion of human hematopoietic stem cells (HSCs), including HSCs that express CD34 protein (CD34-positive HSCs, or CD34+ HSCs). In these methods, the CD34+ HSCs may be CD45+/CD34+ HSCs and/or CD133+CD38− progenitor cells. These methods advantageously expand HSCs many fold (for example, at least 50-fold) quickly and efficiently, while minimizing the differentiation of these HSCs.

Flow 1400 may be performed in embodiments to expand target cells, such as CD34+ HSCs in monoculture or co-culture. Flow 1400 starts at step 1404 and proceeds to step 1412 where expanded cells (e.g., CD34+ HSC's)) may be removed from a bioreactor.

Similarly, the cells to be expanded in these methods may be cells collected from a donor fluid (e.g., one or more blood components) that may include stem cells, CD34+ HSCs, T-cells, monocytes, and/or natural killer (NK) cells. In these methods, specific "target" cells within the donor fluids (e.g. CD34+ HSCs) may be expanded while other cells present in the donor fluid are removed or reduced in number.

Figure 8:
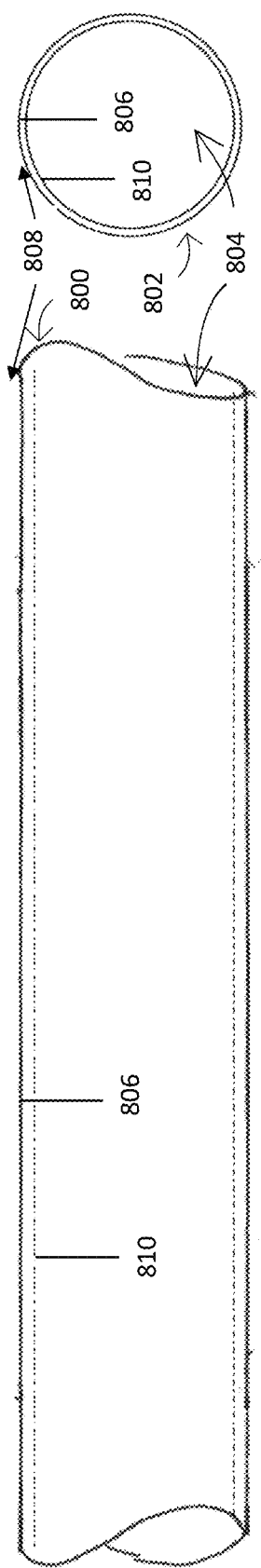
FIG. 8 shows a schematic representation of a hollow fiber in accordance with implementations of the present disclosure.

These methods may include expanding the cells in culture on a membrane. Within these methods of cell expansion, the membrane may be useful in trapping, collecting, and/or otherwise holding cells. The membrane may be arranged in any form, such as a flat sheet, a filter matrix, a hollow fiber, any combination thereof, and/or any plurality thereof. In these methods, the membranes may comprise a coating on at least one surface of the membrane, wherein the coating comprises stromal cell-derived factor-1 (SDF-1), and fibronectin or isoforms, or functional equivalents thereof. A particularly useful membrane within the methods of this disclosure is a hollow fiber or a plurality of hollow fibers, as they appear within a hollow fiber bioreactor. Such hollow fibers contain an interior portion or surface within the lumen of the hollow fiber, and an exterior surface ("extracapillary" side or surface). The hollow fiber membrane may comprise a plurality of hollow fibers. An example of a hollow fiber may be as shown in the schematic representation of FIG. 8, depicting a length of the hollow fiber 800 and an end of the hollow fiber 802, with a lumen 804 and an extracapillary side 808 of the hollow fiber 800. As depicted in FIG. 8, the lumen surface 806 may have a coating 810.

In some examples of these methods, the membrane may be used in conjunction with a cell processing device. In one example, the cell processing device may be the SPECTRA OPTIA® apheresis system, COBE® spectra apheresis system, and the TRIMA ACCEL® automated blood collection system, all manufactured by Terumo BCT, of Lakewood, Colo. After the cells are collected from a donor, the cells may be passed through the membrane to isolate target cells therefrom.

In some examples of these methods, the membrane may be used in conjunction with a cell expansion device. In one example, the cell expansion device may correspond to the Quantum® Cell Expansion System manufactured by Terumo BCT, of Lakewood, Colo. After the target cells are isolated (e.g., as described above), the target cells may be expanded in the membrane to, for example, increase a number of the target cells contained therein.

Figure 9:
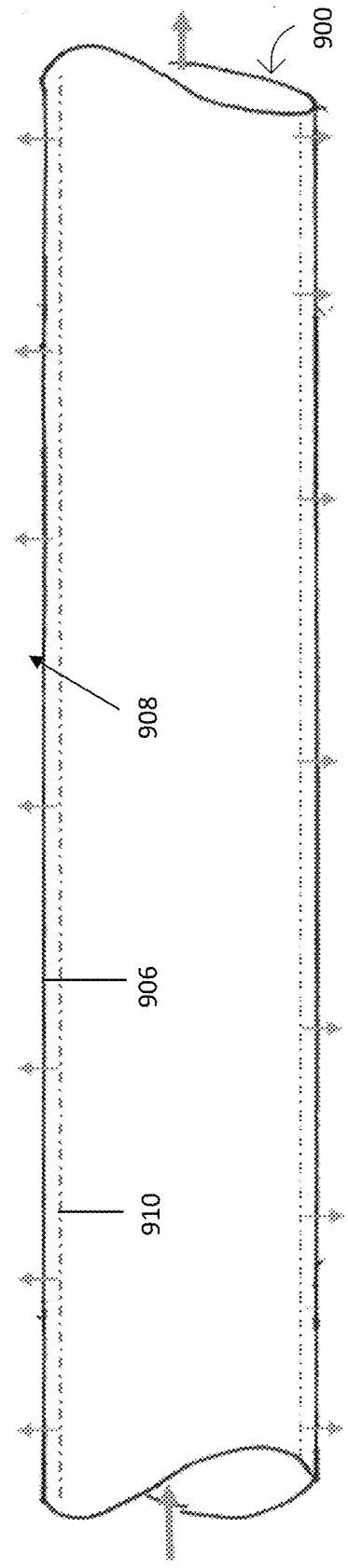
FIG. 9 shows a schematic representation of ultrafiltration from the lumen side to the extracapillary side of the hollow fiber in accordance with an implementations of the present disclosure.
Figure 10:
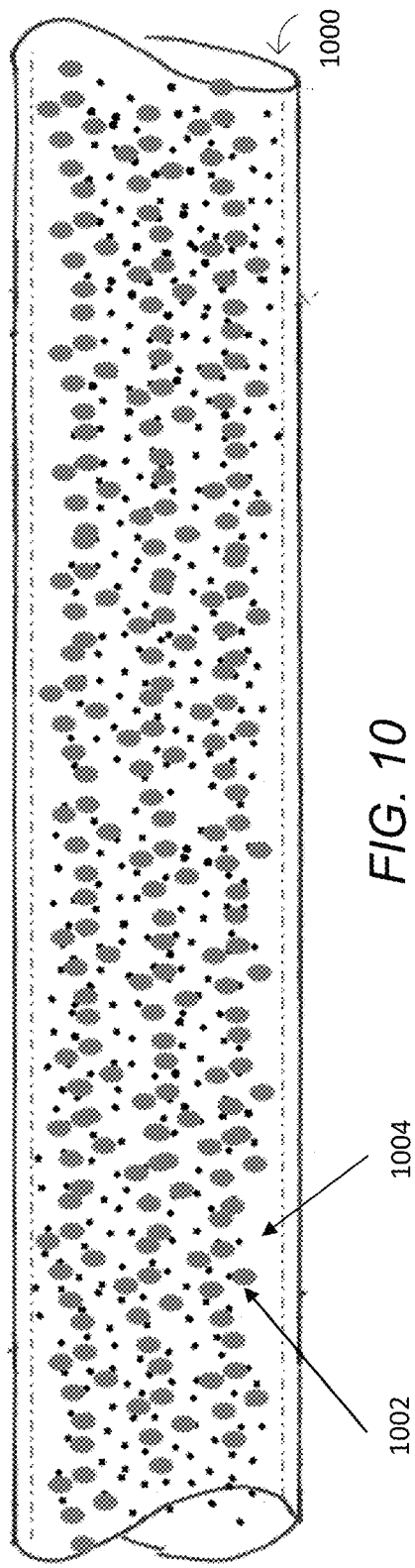
FIG. 10 shows a schematic representation of flow stopped for segregating mixed cell populations in accordance with implementations of the present disclosure.
Figure 11:
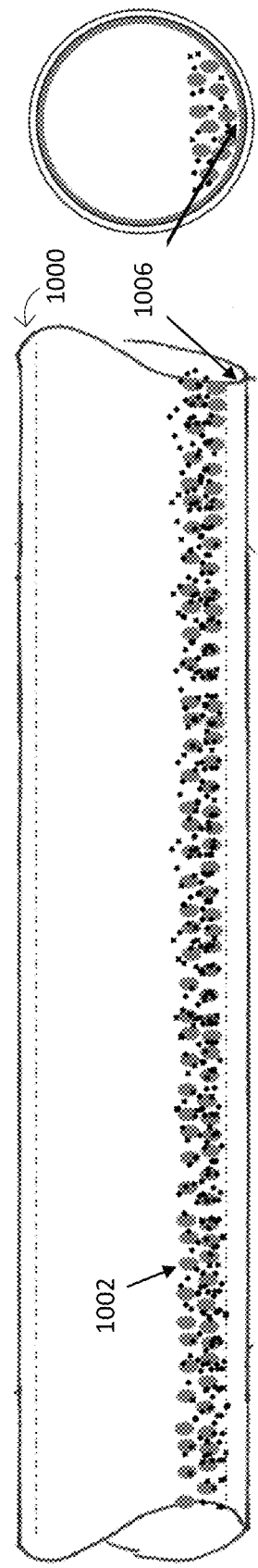
FIG. 11 is a schematic representation showing cells falling to the bottom of the hollow fiber in accordance with implementations of the present disclosure.

Capture of small sized species, such as proteins or exosomes may be conducted on a continuous flow basis over the membrane. Diffusion dynamics may be effective in helping to transport these species to the membrane where they can be captured by their conjugate chemistry which has been deposited on the membrane. Transport to fiber walls may be further assisted by moderate ultrafiltration from the lumen side 906 to the extracapillary side of the hollow fiber 900 as illustrated in the schematic representation of FIG. 9 (arrows indicate direction of ultrafiltration flow). Ultrafiltration flow may occur through a coating 910 present on the lumen surface 906 of the hollow fiber 900. Flow may be stopped for segregating mixed cell populations as illustrated in the schematic representation of FIG. 10, wherein particles 1002 in the lumen of the hollow fiber 1000 are suspended in the lumen 1004 while flow through the lumen 1004 has stopped. When there is no flow, the particles 1002 (e.g., HSCs) may fall to the bottom 1006 of the hollow fiber 1000 as illustrated in the schematic representation of FIG. 11. At this point, target species (such as cells) may adhere to the surface(s) of the membrane and non-target species (such as cells or cellular debrix) may be washed from the membrane leaving target species contained on the membrane. In one example, when non-target species have been removed, a release mechanism (including but not limited to changing pH, changing temperature, displacing binder chemistry) may be used to release the association (such as a bond) between the membrane components and the target species (for example between an aptamer and a cell membrane antigen) leaving the target species in their native, unmodified state. For example, an aptamer may be cleaved by an appropriate nuclease to break the bond between an aptamer and a cell, to release the cell.

The membrane may comprise one or more coatings that are configured to attract, collect, and/or hold target cells, which may then be expanded. In the instance when the membrane is the hollow fibers of a hollow fiber bioreactor, the hollow fibers may comprise a coating on one or both of the lumen surface and the extracapillary surface of the hollow fibers. The coating provided in this disclosure may be a coating that is chemically linked to the membrane (e.g., through hydrophobic and hydrophilic interaction). In some examples, a base coating material may serve as a first coating layer, and a secondary coating material may serve as a secondary coating layer. These coating materials may be applied to a membrane sequentially or together. Examples of a first coating material may include fibronectin, vitronectin, any extracellular matrix (ECM) glycoprotein, collagen, enzyme, equivalents and/or combinations thereof, and/or any molecule or material that is capable of providing cellular adhesion to a membrane or other surface. Examples of a secondary coating material may include a soluble protein moiety, biotinylated molecules, an anti-biotin antibody, a biotin-binding and/or streptavidin-binding peptide, a streptavidin, an avidin, monoclonal antibodies, aptamers (e.g., aptamers targeted toward specific cell surface markers), cytokines (e.g., Interleukin (IL)-6, IL-21), chemokines (e.g., stromal cell-derived factor (SDF)-1), equivalents and/or combinations thereof.

The coating may be applied in a single chemical operation. For instance, a first molecule (e.g., the first-part coating material) and a second molecule (e.g., the second-part coating material) may be conjugated outside of the membrane and then coated onto the membrane at the same time. When formed by coating membranes of this disclosure may be used to (1) make a selective bioreactor to expand cells; and/or (2) create a filter that can capture a specific target cell or molecule (such as any biotinylated molecule or cell).

In one example, the membrane may comprise one or more materials that promote cellular adhesion to at least one surface of the substrate. For example, the coating may comprise the dimeric glycoprotein fibronectin, or a functional equivalent of fibronectin, such as the many known isoforms of fibronectin created through alternative splicing of its pre-mRNA, or other proteins that contain the integrin-binding sequence, Arg-Gly-Asp (RGD) of fibronectin proteins that provides the primary cell adhesive activity of fibronectin.

Figure 12:
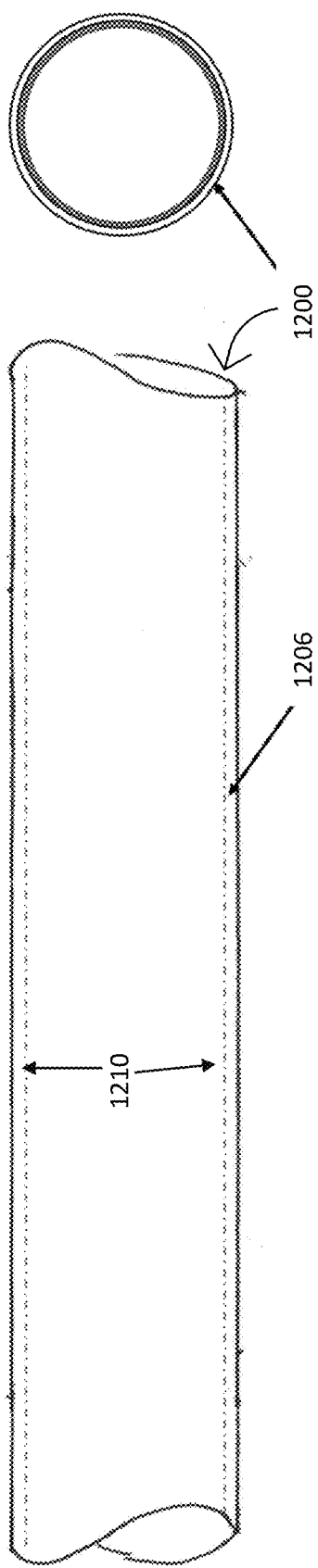
FIG. 12 is a schematic representation showing a membrane coated with a mixture of fibronectin and SDF-1.

Additional useful coatings may include one or more protein moieties. Such protein moieties may be selected to target specific target cells present within a donor fluid. For example, the protein moiety may be a chemokine, such as stromal cell-derived factor-1 (SDF-1), which may be used to enhance collection of CD34+ HSCs from a donor fluid (e.g., when compared to an uncoated membrane or a membrane coated only with fibronectin). Another useful protein moiety in these coatings may be interleukin-21 (IL-21). Another useful protein moiety in these coatings may be the combination of SDF-1 and IL-21. Another useful protein moiety in these coatings may be the combination of fibronectin and SDF-1, as depicted in FIG. 12, wherein a coating 1210 comprising the combination of combination of fibronectin and SDF-1 is associated with the lumen surface of the hollow fiber 1200. Additional coatings of the membrane may be selected to target, collect, and/or hold the same or different cells from within a donor fluid.

In these methods, the membrane may be coated with a mixture of fibronectin and a soluble protein moiety as illustrated in the schematic representation of FIG. 12.

Figure 13:
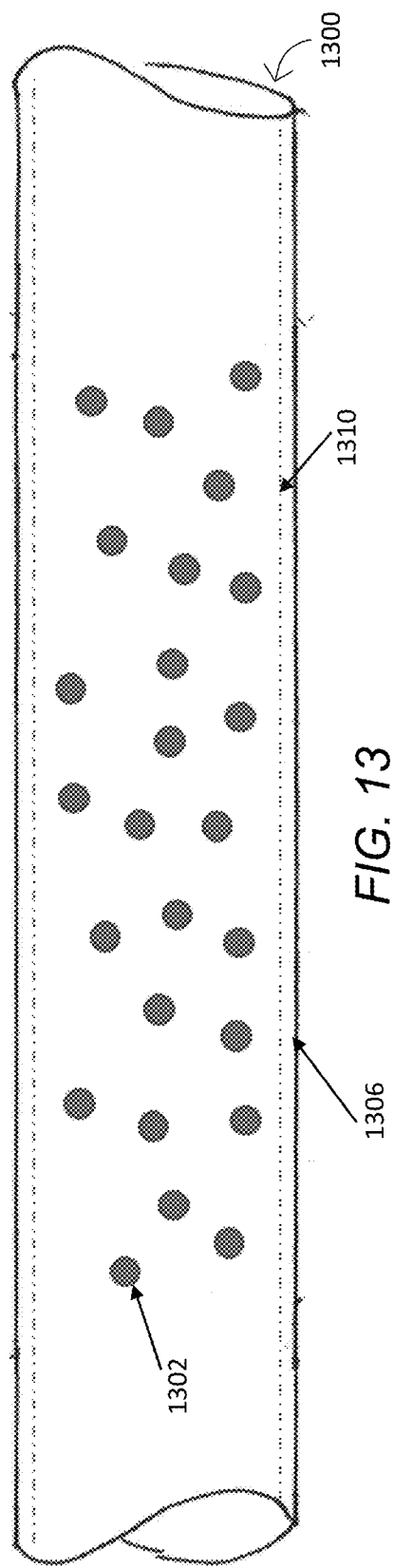
FIG. 13 is a schematic representation showing a cell suspension in a coated membrane.
Figure 14:
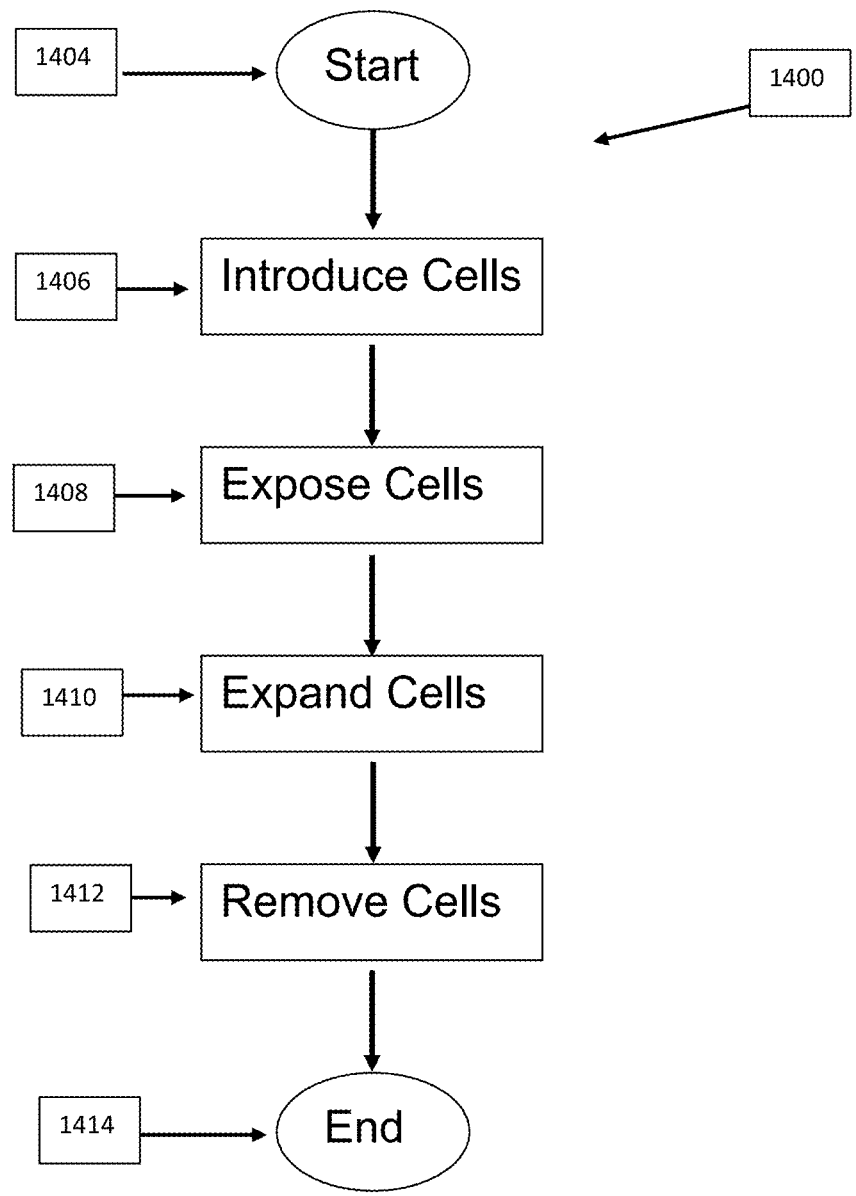
FIG. 14 illustrates flow 1400 that may be performed in embodiments to expand cells (e.g., HSCs). Although specific devices may be described below for performing steps in flow 1400, embodiments are not limited thereto. For example, some steps may be described as performed by parts of a cell expansion system (e.g., CES's 500 or 600) or a processor (1100 (FIG. 7)), which may execute steps based on software provided as processor executable instructions. This is done merely for illustrative purposes, and flow 1400 is not limited to being performed by any specific device.

As depicted in FIG. 13, in these methods, a plurality of cells 1302 (such as a suspension of HSCs) may be introduced into the hollow fiber membrane 1300 having a coating 1310 on the lumen surface 1306.

In some implementations, the coated membrane may be coated with a mixture of fibronectin and a soluble protein moiety to capture biotinylated molecules, such as streptavidin, avidin, and/or anti-biotin antibodies and/or functional equivalents thereof.

Figure 15:
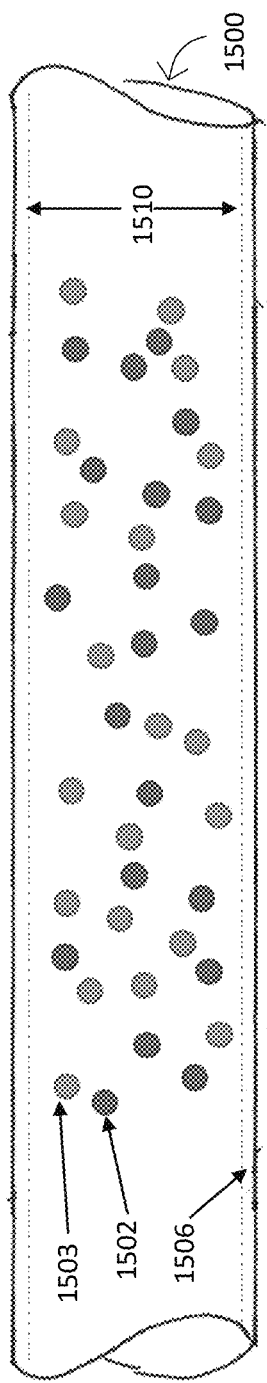
FIG. 15 is a schematic representation depicting a suspension of target and non-target species in the lumen of a hollow fiber having a coating on the lumen surface of the hollow fiber.
Figure 16:
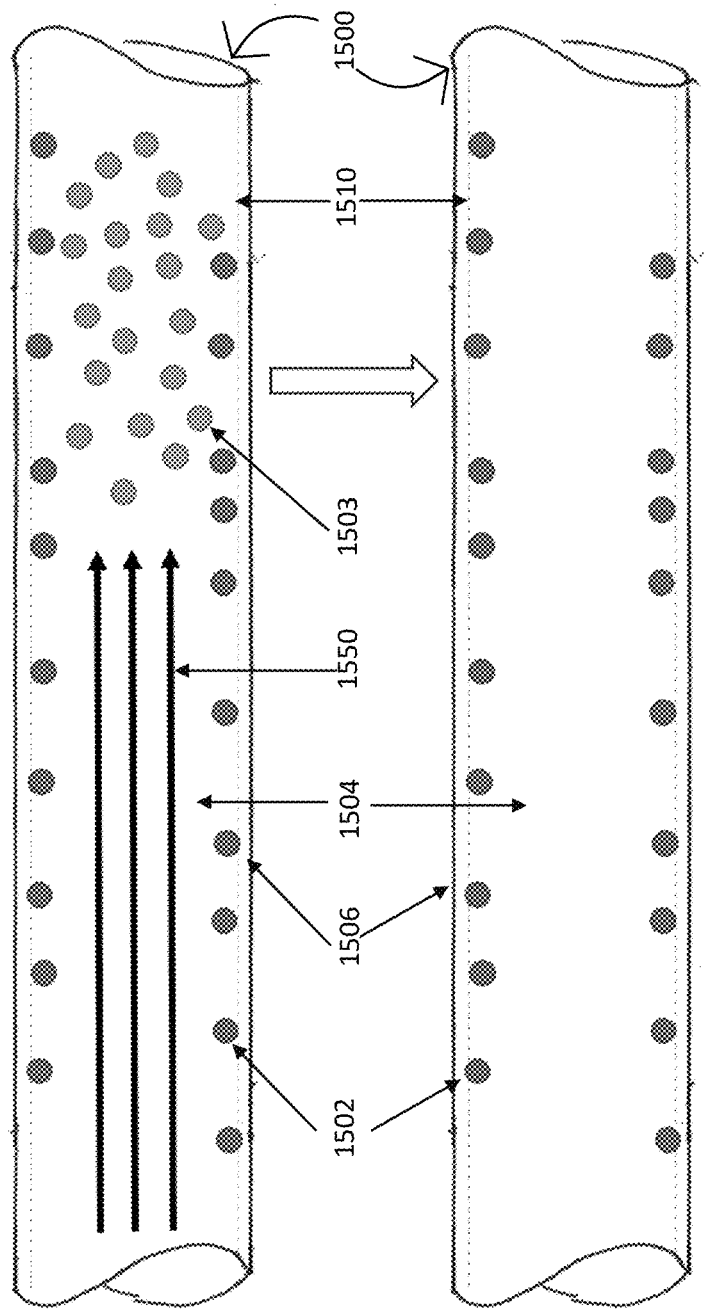
FIG. 16 is a schematic representation depicting the capture of target cells on the coating material on the lumen of a hollow fiber.

As illustrated in the schematic representation of FIG. 15, in some examples, the lumen surface 1506 of the hollow fiber 1500 may have a coating 1510, which may be, for example, a coating comprising biotinylated molecules. In one example, this type of membrane coating may allow for target species 1502 (such as HSCs) within a suspension of non-target species 1503 (such as red blood cells) to be captured. The coated membrane may be used to isolate or captures target cells from a mixed population of cells. As depicted in FIG. 16, target cells 1502 may be captured by, for example, a protein moiety present in the coating 1510 on the lumen surface 1506 of the hollow fiber 1500. Following flushing 1550 of the hollow fiber 1500, non-target species 1503 are removed from the lumen 1504 of the hollow fiber 1500, while target species 1502 remain bound to the lumen surface 1506 of the hollow fiber 1500.

In these methods, a plurality of cells are directed into contact with a membrane, which may be a coated membrane of this disclosure, and expanded while in contact with the membrane. In the instance which a hollow fiber membrane is used in these methods, the plurality of cells may be introduced 1406 into hollow fibers of a hollow fiber bioreactor, wherein the hollow fibers each comprise an interior lumen and an extracapillary side, as described above. The plurality of cells may be first purified by various means prior to being directed into contact with the membrane. Alternatively, the plurality of cells may be directed into contact with the membrane without any initial purification, such as direct from collection from a donor source of cells (e.g. a collection of peripheral blood, or bone marrow, or cord blood (CB)), which may include introducing the plurality of cells into a plurality of hollow fibers without any prior purification. The cells may be directed into contact with the membrane and then left in that position to associate with the membrane, before additional circulation or movement against the membrane to "seed" additional cells on the membrane or remove residual cells or cellular debris from the membrane. When the membrane includes the hollow fibers of a hollow fiber bioreactor, this procedure may advantageously include circulating, with a pump, the plurality of cells within the lumen of the hollow fibers, and then stopping the pump to allow a portion of the plurality of cells to attach to a first portion of the lumen of the hollow fibers, and then rotating the hollow fiber bioreactor 180 degrees from an initial position before again circulating, with the pump, the plurality of cells within the lumen of the hollow fibers, and then stopping the pump to allow a portion of the plurality of cells to attach to a second portion of the lumen of the hollow fibers.

The cells may be expanded 1410 by exposing 1408 the cells in the hollow fibers to growth conditions. The growth conditions may include exposing the cells to one or more of a cell growth media, for example, by circulating a cell growth media through the lumen of hollow fibers of a hollow fiber bioreactor and/or through the extracapillary side of the hollow fibers. Alternatively or additionally, the growth conditions may comprise exposing the cells to one or more growth factors. Useful growth factors may include FMS-like Tyrosine Kinase 3 Ligand (Flt-3L), Stem Cell Factor (SCF), thrombopoietin (TPO), glial cell-derived neurotrophic factor (GDNF), interleukin-3 (IL-3), interleukin-6 (IL-6), IL-21, SDF-1, or combinations thereof. In the instance GDNF is present in the growth media, it may be particularly useful at a concentration of 0.5% to 2% weight per volume, such as at a concentration of about 10 ng/mL in the growth media.

Within these methods that use the membrane of hollow fibers of a hollow fiber bioreactor, a first media may be used in the lumen of the hollow fibers and a second media may be used in contact with the extracapillary side of the hollow fibers. In these methods, the media in the lumen may be concentrated in at least one component relative to the concentration of the same component on the extracapillary side of the hollow fibers. In these methods, the concentrated component may be GDNF, SR-1, SCF, TPO, Flt-3L, IL-3, IL-6, SDF-1, fibronectin, or combinations thereof. In these methods, the concentrated component may be concentrated at least five-fold, or at least ten-fold.

Another useful factor for expanding the cells may include an aryl hydrocarbon receptor antagonist, such as StemRegenin 1 (SR1) or UM171, which was developed at the University of Montreal and which is in clinical development for cell therapy by ExcellThera, Inc.

The coating may be used to provide a specialized environment for cell culture (e.g., when the coating comprises a base coating material, such as fibronectin, and a secondary coating material comprising a soluble protein moiety, such as SDF-1, IL-21). Accordingly, this disclosure provides compositions useful for expanding CD34+ HSCs. These compositions may comprise at least one of glial cell line-derived neurotrophic factor (GDNF), and an aryl hydrocarbon receptor (AHR) antagonist (such as SR-1). These compositions may also include at least one of SCF, TPO, Flt-3L, IL-3, IL-6, SDF-1, and fibronectin. In these compositions, GDNF may be is present at a concentration of 0.5% to 2% weight per volume, or at a concentration of at least 10 ng/mL. In these compositions, fibronectin and SDF-1 may be immobilized on a cell culture surface, such as a semipermeable membrane. These compositions may increase levels of BCL2 and inhibit HSC differentiation.

The coated membranes of this disclosure may be used to provide a specialized environment to capture biotinylated molecules, such as streptavidin, avidin, anti-biotin, (e.g., when the coating comprises a first coating material, such as fibronectin, and a secondary coating material comprising a biotin capture moiety, such as biotinylated molecules, aptamers targeted toward specific cell surface markers, or soluble moieties such as a cytokine (e.g., IL-6)).

At least one benefit to the chemical coating described herein is the ability to manufacture membranes (e.g., hollow fiber membranes) having the coating in a sterile environment. A sterile package including the chemically coated, and sterilized, coated membrane may be opened and ready to use after removing the membrane from the package (e.g., without requiring further processing).

In one example, the Quantum® Cell Expansion System bioreactor hollow fiber membrane (HFM) may be coated with a coating material comprising streptavidin-fibronectin. This coating material may be used, for example, to select or isolate specific cell types when subsequently coupled with biotinylated cell-specific monoclonal antibodies (mAbs).

In some examples, a fibronectin-streptavidin foundation may be used as the coating material for the attachment of biotinylated molecules to functionalize the surface of a polyethersulfone HFM bioreactor, or preparatory columns, for cell selection. Fibronectin may bind to the polyethersulfone HFM in the Quantum® Cell Expansion System bioreactor through the adherence and expansion of adherent cells such as mesenchymal stromal/stem cells (MSCs), fibroblasts and aortic endothelial cells. This fibronectin-streptavidin conjugation may take advantage of a high affinity of streptavidin binding for biotin. While considering available protein coupling biochemistries, it may be important to keep the protocols direct and efficient with minimal residue or reactants to accommodate their adaption in the manufacturing of cell therapy products. In one example, fibronectin-streptavidin mixture or conjugate may be mixed and/or linked, which will allow the HFM bioreactor or column with biotinylated cytokines, chemokines, and/or other ligands to facilitate cell selection and/or expansion. Other affinity separations of biomolecules may also be used. In any case, this protein-protein conjugation can be viewed as a platform for affinity processes associated with cell therapy which uses available technology.

In these methods, a mixture of fibronectin and streptavidin may be used as the coating material for the coated membrane. This process may include reconstitution of lyophilized fibronectin and streptavidin (e.g., in a ratio of 1:3.3 by mass) in water at ambient temperature for approximately 30 minutes. After the conjugation of fibronectin-streptavidin, the mixture volume may be brought up to 100 mL with phosphate buffered saline w/o Ca2+-Mg2+ and introduced into the Quantum® Cell Expansion System using the "Coat Bioreactor" task for a sufficient period of time (e.g., 8 hours). After the bioreactor coating, excess unbound conjugated protein may be washed out and a selected biotinylated molecule, for example, cytokine (interleukin or growth factor), epitope, ligand, monoclonal antibody, stains, or aptamer, may be introduced into the Quantum® Cell Expansion System bioreactor using the "Coat Bioreactor" task for coupling to the fibronectin-streptavidin coating. Once complete, the resulting fibronectin-streptavidin-bioconjugate protein may be ready for use in cell selection or cell signaling (including differentiation) applications. Other applications may include the coating of preparatory HFM columns or matrixes which could be used for cell selection or differentiation prior to the introduction of cells into the Quantum® Cell Expansion System.

In these methods, recombinant or semi-synthetic fibronectin or fibrinogen may be substituted for plasma-derived fibronectin. Extracellular matrix proteins such as fibronectin may bind to the polyethersulfone hollow fiber membrane by virtue of polarity and hydrogen bonding. Fibronectin has a naturally adhesive nature due to its glycoprotein structure and specific domains which may allow fibronectin to bind to both polyethersulfone and cell membrane integrins.

In one example, the covalent coupling of fibronectin to streptavidin, using a similar mass ratio as outlined above, may be achieved using a streptavidin conjugation kit. This kit may make use of a specific linkage modifier and quencher chemistry to generate a covalent linkage between fibronectin and streptavidin in a time period of 30 minutes to 24 hours, and in some implementations in a time period of 3 hours to 15 hours. In some examples, the time to generate a covalent linkage between fibronectin and streptavidin may be approximately 4 hours, plus or minus 30 minutes. The affinity of the chosen biotinylated molecule to streptavidin, in the covalent coating method, may be similar to the affinity of the biotinylated molecule in the fibronectin-streptavidin mixture coating method. One advantage of the covalent approach may include an improved stability of the fibronectin-streptavidin coupling.

The coupling of streptavidin-biotinylated molecules to fibronectin using a molar ratio, for example, of 1:3 (fibronectin:streptavidin) may be useful. In some examples, the coupling of the fibronectin-streptavidin biotinylated molecules to the HFM bioreactor may be a two-step process. This conjugation coating chemistry may be a platform for binding an array of biotinylated molecules for cell selection, stimulation, expansion, or differentiation.

Fibronectin-streptavidin protein conjugate may be selected as an adhesion molecule for the Quantum® Cell Expansion System bioreactor. Coupling biotinylated cell-specific mAbs or protein epitopes to the fibronectin-streptavidin conjugate may exploit the high affinity of streptavidin for biotin at a specific ratio of up to and including 1:4 with an approximate disassociation constant of $Kd=10^{-14}$ to $10^{-15}$ M. Examples of biotinylated antibodies or epitopes which are cell-specific may include anti-CD3 mAb for parent T cells, anti-CD4/CD25 mAb for human T-reg cells, anti-CD8 mAb for human T-effector cells, anti-CD34 mAb for hematopoietic stem cells, or anti-CD56 mAb for NK cells. The streptavidin-biotin linkage may comprise a strong non-covalent linkage and, as such, this functional specificity can be used to select for virtually any cell type by simply changing the specificity of the biotinylated mAb conjugate. In addition, it is also possible that the reverse approach could be utilized where biotinylated-fibronectin would couple with streptavidin-cell specific mAb, which could be used to select cells of interest. If the first approach were used, then the biotinylation of mAbs, with the small biotin molecule (m.w. 244.3 Daltons), is less likely to affect mAb binding or cell antigen recognition. Secondly, the net negative charge and lack of glycosylation streptavidin may serve to minimize the non-specific binding of cells. This concept can leverage the highly specific interaction and versatility of the streptavidin-biotin interaction to provide a better adhesion system. In some examples, cells may be enzymatically separated from the streptavidin-fibronectin-biotin-mAb-cell complex by enzymatically cleaving the DNase-sensitive linker.

Accordingly, this disclosure also provides a coated membrane, and methods of making and using the same. These coated membranes may be hollow fibers, including those hollow fibers used in hollow fiber bioreactors. These coated hollow fiber membranes may include lumen surface and an extracapillary surface and have a first coating on at least one of the lumen surface and an extracapillary surface. The first coating may comprise a material that promotes cellular adhesion to at least one of the lumen surface and an extracapillary surface. The second coating on at least one of the lumen surface and an extracapillary surface, may comprise a soluble protein moiety. In these coated hollow fiber membranes, the first coating may comprise fibronectin. In these coatings, the second coating may comprise at least one of a cytokine, an aptamer, a chemokine (for example, SDF-1 or IL-21), a monoclonal antibody, streptavidin, avidin, a biotinylated molecule, and an anti-biotin antibody or a functional fragment thereof. These membranes may be composed of a material comprising polysulfone or polyethersulfone.

In these coated hollow fiber membranes, the amount of the fibronectin coating the hollow fiber may be 0.001 µg/cm$^2$ to 2 µg/cm$^2$, or may be 0.01 µg/cm$^2$ to 1.0 µg/cm$^2$, or may be 0.10 µg/cm$^2$ to 0.50 µg/cm$^2$, or may be 0.20 µg/cm$^2$ to 0.40 µg/cm$^2$, or may be 0.23 µg/cm$^2$ to 0.24 µg/cm$^2$. In these coated hollow fiber membranes, the amount of the SDF-1 coating the hollow fiber may be 0.001 ng/cm$^2$ to 0.30 ng/cm$^2$, or may be 0.01 ng/cm$^2$ to 0.10 ng/cm$^2$, or may be 0.05 ng/cm$^2$ to 0.09 ng/cm$^2$, or may be 0.075 ng/cm$^2$.

This disclosure also provides methods of forming a coated hollow fiber membrane. These methods include providing a hollow fiber membrane having a lumen surface and an extracapillary surface, and applying a first coating onto the lumen surface of the hollow fiber membrane, and applying a second coating onto the lumen surface of the hollow fiber membrane. In these methods, the first coating may comprise a material that promotes cellular adhesion to at least one of the lumen of the hollow fiber membrane and the extracapillary surface of the hollow fiber membrane (such as fibronectin) and the second coating may comprise a soluble protein moiety, such as one or more of one of a cytokine, an aptamer, a chemokine, a monoclonal antibody, streptavidin, avidin, a biotinylated molecule, and an anti-biotin antibody or a functional fragment thereof. In these methods, applying the first coating and the second coating material may comprise conjugating a first coating material and a second coating material into a conjugate apart from the hollow fiber membrane and coating the conjugate onto the lumen surface of the hollow fiber membrane. These methods may include applying the first coating onto the extracapillary surface of the hollow fiber membrane and/or applying the second coating onto the extracapillary surface of the hollow fiber membrane. In these methods, the first coating may be fibronectin, and the second coating may be SDF-1 or interleukin-21 IL-21.

As described herein, the bioreactor (e.g., the HFM, the hollow fiber device, and/or the hollow fibers) may be coated sequentially. Sequentially coating the bioreactor may provide enhanced exposure to the SDF-1 moiety over time. For instance, in accordance with an example protocol, on Day −2 (e.g., two days before seeding): the bioreactor HFM may be coated with fibronectin (e.g., using the "Coat Bioreactor" task described above), on Day −1 (e.g., one day before seeding): the bioreactor HFM may be coated with SDF-1 (e.g., using the "Coat Bioreactor" task described above), and on Day 0 (e.g., the day of seeding): the bioreactor may be seeded with CB-derived CD34+ HSCs. In some examples, each coating may take between 8 hours and 24 hours to complete.

In these methods, the cells in contact with the membrane (such as cells within the lumen of a plurality of hollow fibers) may be expanded by growing in a monoculture (i.e., substantially in the absence of other cell types) or in a co-culture (i.e., in the presence of other cell types). For example, in these methods, CD34+ HSCs expanded in hollow fibers may be expanded in monoculture, wherein no additional cell type is co-cultured with the CD34+ HSCs in the hollow fibers. In these methods in which CD34+ HSCs are expanded in hollow fibers in monoculture, the hollow fibers may comprise a coating comprising SDF-1 and fibronectin on at least one of the lumen surface and the extracapillary surface of the hollow fibers. In these methods, CD34+ HSCs are advantageously expanded in the presence of SDF-1 and fibronectin without the need for other cells in co-culture.

In these methods, the plurality of cells (such as CD34+ HSCs) may be expanded by growing in co-culture. CD34+ HSCs may be expanded in co-culture with mesenchymal stem cells. In these methods, cells to be grown in co-culture (such as mesenchymal stem cells) may be introduced into the hollow fibers before introducing the plurality of cells for expansion into the hollow fibers. The cells to be grown in co-culture (such as mesenchymal stem cells) may be grown in monoculture in the hollow fibers (such as by exposing the mesenchymal stem cells in the hollow fibers to growth conditions) before introducing the plurality of cells (such as CD34+ HSCs) to be expanded. Alternatively or additionally, the plurality of cells (such as CD34+ HSCs) to be expanded may first be grown in co-culture (such as in co-culture with mesenchymal stem cells) in a static growth chamber (such as traditional cell culture wells or flasks) before removing all or a portion of the plurality of cells (such as CD34+ HSCs) to be expanded from the static growth chamber and introducing the plurality of cells from the static growth chamber into the hollow fibers.

In these methods, the expansion of the cells may be advantageously sufficient to expand a plurality of cells comprising CD34+ HSCs obtained from a single unit of blood or tissue to a plurality of expanded cells sufficient for at least one engraftment procedure for a human recipient. In these instances, the single unit of blood may be cord blood, or the single unit of tissue may be bone marrow.

In these methods, the expanded cells comprising CD34+ HSCs may have at least 90% viability after expansion. In these methods, the expanded cells comprising CD34+ HSCs may be expanded at least 50-fold.

In some examples, this disclosure provides a method and device for the isolation of a target species, for example a target cell or a target molecule, from a mixed population of non-target species. Isolation of a target cell from a mixed population of cells may be used to describe the method and device. A hollow fiber device similar to a hemodialyzer may be used in the cell isolation procedures. As described above, the intracapillary (lumen) walls of hollow fibers may be coated such that a specific binding reagent (e.g., coating materials) is uniformly attached to the intracapillary surface of the hollow fiber device. Additionally or alternatively, the extracapillary walls of the hollow fibers may be treated with a binding reagent, increasing a surface area (e.g., for molecular capture).

The binding reagent may, for example, correspond to a monoclonal antibody (mAb) or a sequenced aptamer. The binding reagent may be selected such that the binding reagent has a specificity for a receptor molecule on the surface of the target cell to be isolated. For instance, if T-cells are to be separated from a mononuclear cell (MNC) collection, a binding reagent with specificity for the CD3, CD4, CD8, and/or a combination of T-cell markers may be affixed (e.g., applied, coated, deposited) to the intracapillary surface and/or the extracapillary surface of a hollow fiber forming the membrane. One example of a method of isolating T-cells from the mixed cell population may include attaching antibodies or aptamers to a cell prior to introduction to the membrane and then passed over a streptavidin-coated membrane, such as a streptavidin-coated hollow fiber. In another example, a counter-flow confinement (CFC) approach is used, wherein a collection of cells may be flowed into the lumen side of the hollow fiber membrane. Once the cells are contained within the lumen side of the membrane, counterflow may be minimized to a level sufficient to retain the cells within the fibers. Once target cells are bound to the lumen surface, both longitudinal flow (lumen inlet header to lumen outlet header) and ultrafiltration flow may be used to remove unbound cells from the lumen of the hollow fiber.

In some examples, a release agent may be used to facilitate detachment of target cells from their binding sites (e.g., facilitating target cell harvest). The release agent may be flowed either longitudinally or with ultrafiltration or with both.

Although examples may be described herein in conjunction with a hollow fiber device (e.g., a bioreactor or other device comprising coated membranes arranged as hollow fibers), it should be appreciated that any membrane capable of receiving a coating can be used. For instance, any one or more of the following devices may be used to receive the various coatings and/or perform the methods described herein: large surface area hollow fiber device, a dialyzer (e.g., hemodialyzer), a cell-capture column (e.g., magnetic cell sorting, a magnetic column apparatus), a polysulfone membrane filter device, a cell processing system, and the like.

In these methods, at least a portion of the plurality of expanded cells may be removed 1412 from the membrane (such as the hollow fibers of a hollow fiber bioreactor). The expanded cells may then be stored, or used for transplantation or administration within other therapeutic procedures for a patient, such as a cancer treatment protocol. In these methods, administering the plurality of expanded cells to a patient may reconstitute hematopoiesis in the patient.

Human leukocyte antigen (HLA)-8-allele matched cord blood (CB) transplantation is an allogeneic procedure for the treatment of certain hematological malignancies, hemoglobinopathies, and autoimmune disorders. CB-derived CD34$^+$ stem cells and progenitor cells may be selected for hematopoietic reconstitution because of their increased capacity for self-renewal and proliferation, longer telomeres, and lower incidence of graft vs. host disease (GVHD) through a lower frequency of alloreactive T cells along with their ability to achieve rapid engraftment in hematological transplant recipients. However, one of the challenges in this setting, is to provide a sufficient number of T cell-depleted hematopoietic stem and progenitor cells which may be necessary to support mixed allogeneic hematopoietic stem cell transplantation (HSCT). Only about 4%-5% of the cord blood units stored in CB banks contain a sufficient number of CD34+ HSCs for single unit grafts ($\geq 1.05 \times 10^7$ CD34+ HSCs) or for double unit grafts ($\geq 1.40 \times 10^7$ CD34+ HSCs) for 70 kg patients.

Methods to expand cord blood-derived CD34+ HSCs, in either co-culture with mesenchymal stromal cells or with small molecules in combination with various cytokine supplements, frequently rely on inoculums of 4-6×10$^6$ or more CD34+ HSCs from cord blood units (CBUs). In some implementations (e.g., to extend the range of stored CBUs), a monoculture expansion protocol is provided for low initial seeding of 2×10$^6$ preselected cord blood-derived CD34+ HSCs in a cell processing system (e.g., the Quantum® cell expansion system's perfusion-based, 2-chambered, semipermeable hollow fiber membrane (HFM) bioreactor) using a primary cytokine cocktail comprised of recombinant human-stem cell factor (SCF), -thrombopoietin (TPO), -fms-like tyrosine kinase 3 ligand (Flt3L), -interleukin 3 (IL-3), and 13 interleukin 6 (IL-6) at one-tenth of the manufacturer's recommended concentration. This cytokine cocktail may be further supplemented with recombinant human glial cell-derived neurotrophic factor (rhGDNF) to, for instance, maintain cell viability and combined with the aryl hydrocarbon receptor (AHR) antagonist SR-1. GDNF may upregulate the expression of the anti-apoptotic gene BCL2 in human CB-CD34+ cell progenitors and SR-1 may limit HSC differentiation during CD34+ HSC expansion when implemented with other HSC cytokines. The proximity of mesenchymal stromal cells (MSCs) and hematopoietic stem and progenitor (HSPCs) in the bone marrow sinusoids, coupled with the perivascular support of HSPCs by SCF from CD146+ MSCs, may contribute to their inclusion in hematopoietic co-culture processes. However attractive, the co-culture of MSCs and HSPCs adds complexity, time, and potential variability to the stem cell and progenitor expansion process. Even so, MSC/HSPC co-culture may provide alternative production strategies in CB-derived CD34+ HSCs. Automating the hematopoietic cell and progenitor expansion process may provide a dependable quantity of selected cells for therapeutic indications.

Moreover, the Quantum® System may support the expansion of both adherent MSCs as well as suspension CD3+ T cells and Regulatory T cells with a perfusion-based HFM bioreactor. In the CB-derived CD34+ cell expansion method described herein, the intercapillary (IC) HFM lumen of the bioreactor may be coated with a mixture of human fibronectin (Fn) and the chemokine stromal derived factor 1 (SDF-1) prior to cell seeding in order to mimic the stimulatory and homing effects of bone marrow-derived or Wharton's Jelly-derived mesenchymal stromal cells. The preselected CB-derived CD34+ HSCs may be subsequently propagated under suspension culture conditions, and allowed to adhere to the coated-HFM IC-surface during this process, for example, to engage with the Fn-SDF-1 modified surface. In some cases, immobilized SDF-1 may be required to develop integrin-mediated cell adhesion of CD34+ HSCs by VLA-4 integrin to murine endothelial cells. In this context, hydrogel immobilization of SCF and SDF1α along with the incorporation of the PEG-RGD integrin recognition sequence onto the cell culture surface recapitulates certain aspects of the bone marrow microenvironment. The implementations and examples described herein provide expanding CB-derived CD34+ HSCs with a modified extracellular matrix protein.

In one example, a method and/or system for the automated monoculture expansion of CB-derived HSCs and progenitor cells beginning with mixed, positively selected CB-derived CD34+ HSCs is provided. These cells may be resuspended in serum-free medium and supplemented with a defined hematopoietic cytokine cocktail and expanded under a programmed, but modifiable, perfusion protocol for a period of 8 days, for example, to minimize T cell differentiation in the Fn-SDF-1 coated HFM bioreactor system. Quantum® System-expanded CB-derived CD34+ HSCs may generate a sufficient quantity of cells to support both single and double unit minimal CD34+ dose equivalency while conserving the CD34+ phenotype and with a minimal frequency of lymphocytes. Furthermore, these CB-derived expanded progenitor cells may demonstrate their ability to differentiate into mature hematopoietic colony forming units (CFUs) under methylcellulose assay conditions.

In an example implementation, three master lots of cord blood derived, preselected, mixed CD34+ HSCs may be expanded in an about 2.1 m$^2$ HFM bioreactor with an about 124 mL perfusion-culture volume and harvested using an automated suspension cell protocol. Cells may be introduced into the intracapillary loop (e.g., the IC loop) of the HFM bioreactor through a defined perfusion protocol and maintained within the lumen of the bioreactor with a custom counter-flow fluidics program.

As noted above, the membranes of this disclosure may be used to effectively create a membrane that can capture a specific target cell or molecule. Thus, this disclosure also provides methods of capturing cells. Flow 2400 may be performed in embodiments to capture cells, such as CD34+ HSCs. Flow 2400 starts at step 2404 and proceeds to step 2414 where captured target cells (e.g., HSC's) may be removed from a bioreactor. These methods include introducing 2406 a mixture of target species, such as cells or molecules, and non-target species onto a membrane of this disclosure (such as into hollow fibers of a hollow fiber bioreactor wherein the hollow fibers each comprise an interior lumen and an extracapillary side). As described in detail above, these membranes comprise a coating on at least one surface of the membrane comprising at least one of a material that promotes cellular adhesion, and a protein moiety. In the instance of using a hollow fiber membrane, one or both of the lumen surface and the extracapillary surface of the hollow fibers may be coated with the material that promotes cellular adhesion and/or a protein moiety.

The mixture of species in contact with the membrane may be exposed 2408 to conditions that enhance the association of the target species with the membrane (i.e., "capture conditions") 2410. Examples of capture conditions may include changes in pH, temperature, tonicity, and/or the addition or subtraction of compounds that enhance the association of the target species with the membrane. The implementation of the capture conditions may effectively capture at least a portion of the target cells on a surface of the membrane (such as at least one of the lumen and the extracapillary surface of hollow fibers). Thereafter, at least a portion of the non-target species may be flushed 2412 from the membrane (such as from the lumen of hollow fibers). In these capture methods, the target species may be, for example, CD34+ HSCs and the non-target species may be, for example, additional cell types or cellular debris or blood proteins.

In these capture methods, the coating material on the membrane that promotes cellular adhesion to a surface of the membrane may comprise fibronectin. In these capture methods, the protein moiety may be at least one of stromal cell-derived factor-1 (SDF-1), interleukin-21 (IL-21), streptavidin, avidin, and anti-biotin antibodies or functional fragments thereof. In these capture methods, the coating may comprise fibronectin and SDF-1. In these methods of capturing target cell species (such as CD34+ HSCs), after flushing at least a portion of the non-target cells from the membrane, the captured target cells may then be expanded, for example, by changing the media and/or other conditions at the membrane to enhance growth and expansion of the captured cells, such as CD34+ HSCs. These capture methods may include removing at least a portion of the captured target species (such as CD34+ HSCs) from the membranes. These captured species may be removed 2414 from the membrane after capture of the target species and flushing to remove non-target species, or after the target cell species have been expanded after capture, as described above.

This disclosure also provides methods of capturing cells, using the interaction of biotin and avidin. These methods include introducing a mixture of target species and non-target species into hollow fibers. In these methods, the hollow fibers each comprise an interior lumen and an extracapillary side, and the hollow fibers may comprise a coating on at least one of the lumen surface and the extracapillary surface of the hollow fibers. In these methods, the coating may comprise at least one of streptavidin, avidin, a biotinylated molecule, and an anti-biotin antibody or a functional fragment thereof. In these methods, the target and/or non-target species may be cells (e.g., HSCs) or molecules. In these methods, the mixture of target and non-target species may be exposed to capture conditions, to capture at least a portion of the target species on at least one of the lumen and the extracapillary surface of the hollow fibers. At least a portion of the non-target species may then be flushed from the hollow fibers. In these methods, the target cells introduced into the hollow fibers may comprise biotinylated aptamers or biotinylated antibodies that bind to the coating on the at least one of the lumen surface and the extracapillary surface of the hollow fibers.

These methods in which the target species are cells may include, after flushing at least a portion of the non-target cells from the hollow fibers, the portion of the target cells that are captured on a surface of the hollow fibers may be exposed to growth conditions to expand the portion of the target cells captured in the hollow fibers thereby generating a plurality of expanded target cells. In these methods, after capture of the target cells and flushing of the non-target cells, at least a portion of the captured target cells may be removed from the hollow fibers.

This disclosure also provides methods of expanding cells by perfusion in a cell expansion system. These methods may include coating a hollow fiber bioreactor with a first fluid, wherein the first fluid comprises a signaling factor and/or a coating factor. A plurality of cells may be introduced into the hollow fiber bioreactor, wherein the hollow fiber bioreactor comprises a hollow fiber membrane. The plurality of cells may be exposed to a second fluid, wherein the second fluid comprises a plurality of growth factors. The plurality of cells in the hollow fiber bioreactor may be grown in monoculture or in coculture. In these methods, the first fluid may comprise at least one of fibronectin and SDF-1. In these methods, the fibronectin and the SDF-1 may be mixed together prior to coating the hollow fiber bioreactor. In these methods, the hollow fiber bioreactor may be coated sequentially by coating the hollow fiber bioreactor with the fibronectin and then coating the hollow fiber bioreactor with the SDF-1. In these methods, the hollow fiber bioreactor may be coated sequentially by coating the hollow fiber bioreactor with the SDF-1 and then coating the hollow fiber bioreactor with the fibronectin. In these methods, an amount of the fibronectin used to coat the hollow fiber bioreactor may be 0.001 µg/cm$^2$ to 2 µg/cm$^2$, or 0.01 µg/cm$^2$ to 1.0 µg/cm$^2$, or 0.10 µg/cm$^2$ to 0.50 µg/cm$^2$, or 0.20 µg/cm$^2$ to 0.40 µg/cm$^2$, or 0.23 µg/cm$^2$ to 0.24 µg/cm$^2$. In these methods, an amount of the SDF-1 used to coat the hollow fiber bioreactor may be 0.001 ng/cm$^2$ to 0.30 ng/cm$^2$, 0.01 ng/cm$^2$ to 0.10 ng/cm$^2$, or 0.05 ng/cm$^2$ to 0.09 ng/cm$^2$, or 0.075 ng/cm$^2$.

In these methods, the second fluid may comprise GDNF. In these methods, an amount of the GDNF in the second fluid may be 0.001 ng/mL to 40.0 ng/mL, or 0.01 ng/mL to 20 ng/mL, or 0.10 ng/mL to 15 ng/mL, or 1.0 ng/mL to 15 ng/mL, or 5.0 ng/mL to 15 ng/mL, or 10 ng/mL.

In these methods, the plurality of growth factors may comprise at least one of SCF, TPO, Flt-3L, IL-3, and IL-6. In these methods the second fluid may comprise StemRegenin (SR-1). In these methods an amount of the SR-1 in the second fluid may be 0.001 µM to 3.0 µM, or 0.01 µM to 2.0 µM, or 0.10 µM to 1.0 µM, or 0.75 µM.

In these methods, prior to introducing the plurality of cells into the hollow fiber bioreactor, hollow fiber bioreactor may be coated for a predetermined time period with a mixture of 5 mg of human plasma-derived fibronectin or 0.23-0.24 µg/cm$^2$ of fibronectin and recombinant human Stem Cell Derived Factor 1 (SDF-1) at 0.075 ng/cm$^2$. In these methods, the predetermined time period is 4.0 hours to 16.0 hours, or 8.0 hours to 12.0 hours.

EXAMPLES

Example 1. Short Expansion Strategy for Cord Blood-Derived CD34+ HSCs in the Quantum® System Human cord blood-derived CD34+ hematopoietic stem cells (HSCs) expanded for 8 days or less engrafted more successfully in a humanized, immunodeficient murine model than cells expanded for greater than 8 days. Expanding cord blood-derived CD34+ HSCs for 8 days or less resulted in BALB/C-RAG2 null IL-2r-gamma null murine model humanized mice (Clinical Immunology, 140:102-116, 2011) displaying more consistent human hematopoietic and lymphoid engraftment.

Implementations provide for reducing, or shortening, the time period(s) for the expansion of cells, e.g., CD34+ HSCs and/or CB-CD34+ HSCs, while improving, for example, cell yield, phenotype and functionality. An implementation provides for an inoculum expansion and Quantum® system expansion of HSC CB-CD34+ HSCs in co-culture with mesenchymal stem cells (MSCs), an in situ source of SDF-1, for about 14 days. Further implementations provide for improving, for example, yield, phenotype and functionality with a shortened monoculture protocol. Human cord blood-derived CD34+ HSCs may be expanded in two phases, for example: (1) Inoculum prep expansion of about 1 million CB-CD34+ HSCs in a T25 flask for about 3 days, followed by (2) the expansion of viable CD34+ HSCs by perfusion in the Quantum® Cell Expansion System for about 5 days to maintain the HSC phenotype of CD34+CD38-CD133+ and related engraftment function by using a monoculture technique with fibronectin-immobilized SDF-1 and other growth factors/cytokines. For example, implementations provide for: (1) the use of a shortened timeline for cell expansion of about 8 days: in flask for about 3 days and in the Quantum® System for about 5 days using, for example, (1) an immobilized SDF-1 signaling factor coupled with (2) a novel growth factor cocktail utilizing, for example, one or more of: SCF, TPO, Flt-3L, IL-3, IL-6, GNDF±SR-1, and combinations thereof, in monoculture. In an implementation, a monoculture protocol(s), e.g., a shortened monoculture protocol(s), may use a bi-directional cell reseeding task(s) in the Quantum® System, for example.

CD34+ Mixed Cell Expansion

Flask Study

In an example, a pilot flask study is conducted over seven days. Cord blood-derived CD34+ HSCs were grown at 37° C. with CO$_2$ CD34 complete medium without shaking. Cells were seeded on day 1 at 1×10$^5$ cells/mL in 7 mL and harvested at day 7. A yield of 5,700,000 was considered optimal. CD34 medium produces 11,800,000 cells, while CD34 medium at 1:10 dilution in complete medium produced 9,200,000 cells and CD34 medium at 1:20 dilution produced 5,900,000 cells. Cell viability was 86.2%, 90.3%, and 90.1% for undiluted, 1:10 dilution, and 1:20 dilution CD34 medium, respectively (n=2 per arm, with cells counts performed in triplicate).

Freeze-Thaw Study

The feasibility of expanding thawed, mixed cord blood-derived CD34+ HSCs (Stem Cell Technologies, Lot 1907519003, was tested. The cells (1.1×10$^6$ and 2. 1×10$^6$ CB-derived CD34+ HSCs are seeded in two, separate monoculture Quantum runs, respectively) were cultured in SCGM media (Cat. 20802-0500, CellGenix GmbH, Freiburg, Germany) with a modified supplement cocktail (StemSpan™ CD34+supplement at I % by volume plus GDNF and SR-I) using fibronectin-immobilized SDF-1 coated surfaces in T25 flasks. Both the flasks and the Quantum CESs are coated overnight at 37° C. with the Fibronetin-SDF-1 protein mixture prior to cell seeding. Fluidics-wise, flasks were in a static condition, whereas the Quantum systems were perfused overnight (12-15 hours) using the Quantum CES "Coat Bioreactor" Task (IC Inlet@ 0 mL/min, IC Circ@ 20 mL/min with Fn/SDF-1, EC Inlet@ 0.1 mL/min with PS, and EC Circ@ 30 mL/min, EC outlet). The cells were cultured for 3 days and in the Quantum® System hollow fiber membrane (HFM) bioreactor for a period of 5 days.

In the feasibility study, two media formulations with SCF, TPO, Flt-3L, IL-3, IL-6, and GNDF and with or without SR-1 cocktail are evaluated for their ability to support the expansion of CB-derived CD34+ HSCs in monoculture. Both experimental arms are seeded with 1×10$^6$ cells in T25 flasks. On day 3, the Q1893 (without SR-1) Quantum® system and Q1894 (with SR-1) Quantum® system are seeded with cell inoculums from their respective flask cultures.

On day 8, harvest yields are 4.49×10$^7$ cells without SR-1 (viability 98.5%) and 5.57×10$^7$ (viability 98.8%) cells with SR-1. Flow cytometry analysis of the cryopreserved hematopoietic stem cell Quantum® system harvest phenotype indicated the CD34$^+$ cell fraction was 1.40×10$^7$ cells or 31.1% of the total harvest without SR-1 and 2.1×10$^7$ or 37.7% of the total harvest with SR-1. The minimum and maximum CD34+ doses are 7,000,000 and 10,500,000 cells, respectively.

Example 2. Monoculture Expansion Strategy for Cord Blood-Derived CD34+ HSCs in the Quantum® System An implementation provides an automated expansion protocol for CB-derived CD34+ HSCs in the Quantum® system's dynamic perfusion-based, 2-chambered, semi-permeable hollow fiber membrane (HFM) bioreactor using a novel cytokine cocktail that may be comprised of, for example, SCF, TPO, Flt-3L, IL-3, IL-6, and Fibronectin-SDF-1 coated membrane, and the cocktail can be supplemented with GDNF and SR-1. In addition, the intracapillary (IC) HFM lumen may be coated with a mixture of human fibronectin and the chemokine SDF-1 to mimic the stimulatory and homing effects of bone marrow-derived mesenchymal stromal cells.

In a series of tests of this automated expansion protocol, three master lots of thawed cord blood (CB) derived, pre-selected, mixed CD34+ HSCs are expanded in an about 2.1m2 HFM bioreactor with an about 124 mL IC volume with an initial cell seeding of 2.0×106 of the CD34+ HSCs. First, cells are resuspended in SCGM base medium supplemented with the growth factor cocktail. The cells are thawed at 37° C. in a water bath, washed in 23 mL of complete medium, and resuspended in 50 mL of complete serum-free GMP SCGM medium (Cat. 20802-0500, CellGenix GmbH, Freiburg, Germany) supplemented with StemSpan™ CD34 Supplement 10X (Cat. 2691, Stem Cell Technologies, Vancouver, BC, Canada), which contains recombinant human FMS-like tyrosine kinase 3 ligand (F1t31), stem cell factor (SCF), thrombopoietin (TPO), interleukin 3 (IL-3), and interleukin 6 (IL-6) at a concentration of 1% by volume, Glial cell-derived neurotrophic factor (GDNF) at 10 ng/mL (Cat. 212-GD-050, R&D Systems, Minneapolis, MN, USA), StemRegenin I (SR-1) at 0.75 1.1M (Cat. 72342, Stem Cell Technologies, Vancouver, Canada), and Penicillin-Streptomycin-Neomycin (PSN) antibiotic mixture 100X at I % by volume (Cat. 15640-055, ThermoFisher Scientific, Waltham, MA, USA). Base medium may be formulated with serum-free GMP SCGM supplemented with SR-I and PSN antibiotic mixture.

Prior to seeding the CD34+ HSC inoculum, the Quantum® System HFM bioreactor (S. A. of 21,000 cm$^2$) is coated overnight with a mixture of 5 mg of human plasma-derived fibronectin (or 0.23-0.24 μg/cm$^2$, Cat. 356008, Corning Life Sciences, Corning, N.Y., USA) and recombinant human Stem Cell Derived Factor 1 (SDF-1) at 0.075 ng/cm$^2$ (Cat. 6448-SD, R&D Systems, Minneapolis, Minn., USA) in 100 mL of PBS w/o $Ca^{2+}$—$Mg^{2+}$ (Cat. 17-516Q, Lonza Group, Walkersville, Md., USA) at a temperature of 37° C. and mixed gas (5% $CO_2$, 20% $O_2$, balance $N_2$).

The cells were then introduced into the intracapillary loop (e.g., the IC loop) of the HFM bioreactor through a defined perfusion protocol and maintained within the lumen of the bioreactor with a custom counter-flow fluidics program. CB-derived CD34+ HSCs were seeded in suspension into the coated HFM bioreactor in 50 mL of complete medium (serum-free GMP SCGM base medium with the following cytokine cocktail: SCF, TPO, Flt-3L, IL-3, IL-6, GDNF, and SR-1) after lumen and extracapillary medium exchange and conditioning (cell expansion medium is conditioned in the Quantum CES by circulating the medium by perfusion through the IE/EC loops of Quantum system bioreactor for at least 10 minutes using the Quantum embedded task entitled "Condition Media" with the following circulation rates: IC Circ @ 100 mL/min, EC Circ @ 250 mL/min, and EC Inlet @ 0.1 mL/min. This equilibrates the mixed gas (20% $O_2$, 5% $CO_2$, and balance $N_2$) in the bioreactor medium by gas exchange in the EC Loop via gas transfer module), expanded in monoculture, and harvested on day 8 of cell culture using Quantum® System automated tasks, as outlined in the automated task settings shown in following Tables 1-3:

TABLE 1

(enlarged Part 1 of 3): Quantum CD34+ Cell Seeding Task(s)

| | Quantum System Prep (Day −1 to 0) | | | | | Load CD34+ Cells (2–20 × 10⁶ cells) Custom 1 (Load Cells and Feed for 2 Days) (Day 0 to 2) | | Condition BR | Feed Cells |
|---|---|---|---|---|---|---|---|---|---|
| | Load Expansion Set | Prime | Coat Bioreactor | IC EC Washout | Condition Media | Step 1 | Step 2 | Step 3 | Step 4 |
| | STEP 1 | STEP 2 | STEP 3 | STEP 4 | STEP 5 | STEP 5 | STEP 6 | STEP 7 | STEP 8 |
| Cell Line | PBS | Default settings | Default settings | Cell Line | None | Cell Line | Cell Line | Cell Line | Cell Line |
| IC Media Line | N/A | | | IC Media Line | Complete | IC Media Line | IC Media Line | IC Media Line | IC Media Line |
| EC Media Line | N/A | | | EC Media Line | Base | EC Media Line | EC Media Line | EC Media Line | EC Media Line |
| Reagent Line | N/A | | | Fn + SDF-1 | None | Reagent Line | Reagent Line | Reagent Line | Reagent Line |
| Wash Line | N/A | | | Wash Line | None | Wash Line | Wash Line | Wash Line | Wash Line |

Task Settings:

| | STEP 1 | STEP 2 | STEP 3 | STEP 4 | STEP 5 | STEP 5 | STEP 6 | STEP 7 | STEP 8 |
|---|---|---|---|---|---|---|---|---|---|
| IC inlet | Default settings | Default settings | Default settings | EC media | None | Cell | IC Media | IC Media | IC Media |
| IC inlet rate | | | | 100 | 0 | 50 | 50 | 80 | 0.1 |
| IC circ rate | | | | −17 | 20 | 0 | 0 | −40 | −0.1 |
| EC inlet | | | | EC Media | None | None | None | None | None |
| EC inlet rate | | | | 148 | 0 | 0 | 0 | 0 | 0 |
| EC circ rate | | | | −1.7 | 30 | 30 | 30 | 30 | 30 |
| Outlet | | | | IC and EC outlet | EC outlet | IC outlet | IC outlet | EC outlet | EC outlet |
| Rocker | | | | In Motion (−90°, 180°, 1 sec) | Stationary (0°) | In Motion (−90°, 180°, 1 sec) | In Motion (−90°, 180°, 1 sec) | In Motion (−90°, 180°, 1 sec) | Stationary (0°) |
| Stop condition | | | | Exchange (2.5 IC volume; 2.5 EC volume) | Manual (≥10 min) | Empty bag | IC volume (50 ml) | IC Volume (310 mL) | Manual (2880 min) |

(enlarged Part 2 of 3): Quantum CD34+ Cell Seeding Task(s)

| | STEP 1 | STEP 4 | STEP 5 |
|---|---|---|---|
| Cell Line | PBS | Cell Line | None |
| IC Media Line | N/A | IC Media Line | Complete |
| EC Media Line | N/A | EC Media Line | Base |
| Reagent Line | N/A | Fn + SDF-1 | None |
| Wash Line | N/A | Wash Line | None |

TABLE 1-continued

Day −1 to 0

| | | Load Expansion Set | Prime | Coat Bioreactor Quantum System Prep | IC EC Washout | Condition Media |
|---|---|---|---|---|---|---|
| | | STEP 1 | STEP 2 | STEP 3 | STEP 4 | STEP 5 |
| Task Settings | IC inlet | Default settings | Default settings | Default settings | EC media | None |
| | IC inlet rate | | | | 100 | 0 |
| | IC circ rate | | | | −17 | 20 |
| | EC inlet | | | | EC Media | None |
| | EC inlet rate | | | | 148 | 0 |
| | EC circ rate | | | | −1.7 | 30 |
| | Outlet | | | | IC and EC outlet | EC outlet |
| | Rocker | | | | In Motion (−90°, 180°, 1 sec) | Stationary (0°) |
| | Stop condition | | | | Exchange (2.5 IC volume; 2.5 EC volume) | Manual (≥10 min) |

(enlarged Part 3 of 3): Quantum CD34+ Cell Seeding Task(s)

| Cell Line | Cells Complete |
|---|---|
| IC Media Line | Base |
| EC Media Line | None |
| Reagent Line | None |
| Wash Line | None |

Day 0 to 2

| | Load CD34+ Cells (2-20 × 10⁶ cells) Custom 1 (Load Cells and Feed for 2 Days) | | Condition BR | Feed Cells |
|---|---|---|---|---|
| | Step 1 STEP 5 | Step 2 STEP 6 | Step 3 STEP 7 | Step 4 STEP 8 |
| | Cell | IC Media | IC Media | IC Media |
| | 50 | 50 | 80 | 0.1 |
| | 0 | 0 | −40 | −0.1 |
| | None | None | None | None |
| | 0 | 0 | 0 | 0 |
| | 30 | 30 | 30 | 30 |
| | IC outlet | IC outlet | EC outlet | EC outlet |
| | In Motion (−90°, 180°, 1 sec) | In Motion (−90°, 180°, 1 sec) | In Motion (−90°, 180°, 1 sec) | Stationary (0°) |
| | Empty bag | IC volume (50 ml) | IC Volume (310 mL) | Manual (2880 min) |

TABLE 2

Quantum CD34+ Cell Redistribution and Increase Feeding Task(s)

| | |
|---|---|
| Cell Line | None |
| IC Media Line | Complete |
| EC Media Line | Base |
| Reagent Line | None |
| Wash Line | None |

Day 2 to 8

CD34+ Cell Redistribution    Feed Cells
Custom 2 (Cell Redistribution and increase Feed)

| | | Step 1<br>STEP 9 | Step 2<br>STEP 10 | Step 3<br>STEP 11 |
|---|---|---|---|---|
| Task Settings | IC inlet | None | IC Media | IC Media |
| | IC inlet rate | 0 | 50 | 0.2* |
| | IC circ rate | 300 | −30 | −0.1* |
| | EC inlet | None | None | None |
| | EC inlet rate | 0 | 0 | 0 |
| | EC circ rate | 100 | 30 | 100 |
| | Outlet | EC outlet | EC outlet | EC outlet |
| | Rocker | In Motion<br>(−90°, 180°, 1 sec) | In Motion<br>(−90°, 180°, 1 sec) | Stationary<br>(0°) |
| | Stop condition | Time<br>(4 min) | IC Volume<br>(150 mL) | Manual<br>(1440 min) |

TABLE 3

Quantum CD34+ Cell Harvest

| | |
|---|---|
| Cell Line | None |
| IC Media Line | Complete |
| EC Media Line | Base |
| Reagent Line | None |
| Wash Line | None |

Day 8-Harvest
CD34+ Cell Harvest
Custom 3 (Harvest)

| | | Step 1<br>STEP 12 | Step 2<br>STEP 13 |
|---|---|---|---|
| Task Settings | IC inlet | None | IC media |
| | IC inlet rate | 0 | 100 |
| | IC circ rate | 300 | −20 |
| | EC inlet | None | EC Media |
| | EC inlet rate | 0 | 60 |
| | EC circ rate | 300 | 30 |
| | Outlet | EC outlet | Harvest |
| | Rocker | In Motion<br>(−90°, 180°, 1 sec) | In Motion<br>(−90°, 180°, 1 sec) |
| | Stop condition | Time<br>(4 min) | IC Volume<br>(400 mL) |

Default tasks are used for Quantum® System priming, IC media/EC media exchange, and media conditioning tasks. In the process, glucose and lactate levels were monitored by i-STAT Analyzer G and CG4+ cartridges (Abbott Point-of-Care, Princeton, N.J.). During cell expansion, the Quantum® System IC and EC inlet flow rates were adjusted in response to the glucose consumption and lactate generation rates and the nature of the automated task. The program uses a gas mixture of about 5% $CO_2$, about 20% $O_2$, and balance $N_2$ at about 37° C. for a period of only about 8 days, to reduce (i.e., to minimize) T cell differentiation during cell culture. Cells are harvested using an automated suspension cell protocol.

Figure 17:
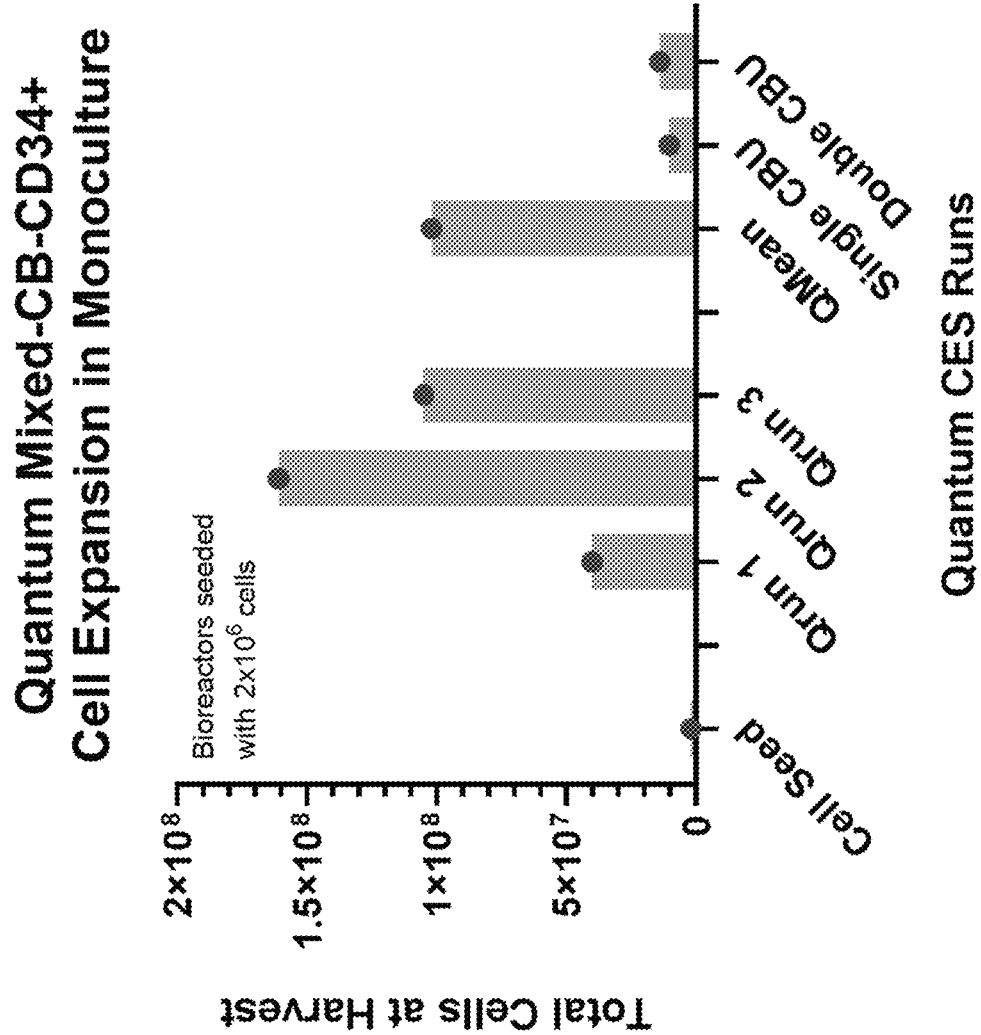
FIG. 17 is a graph showing CD34+ cell harvest yield from three different donor cell lineages after 8 days of monoculture compared to the minimum single and double CBU CD34+ cell dosing guidelines for a 70 kg patient.
Figure 18:
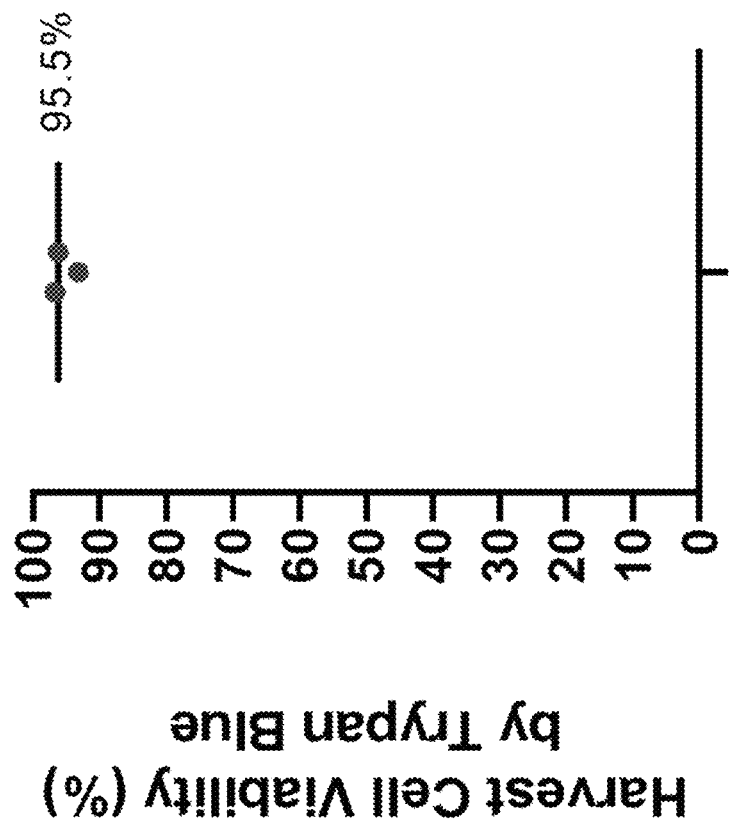
FIG. 18 is a graph showing harvest cell viability as determined by trypan blue dye exclusion.

For example, Quantum System inlet flow rate(s) may range from about +0.1 to about 100 mL/min, and IC circulation flow rate(s) may range from about −40 to about 300 mL/min. Corresponding Quantum System EC inlet flow rate(s) may range from about 0to about 148 mL/min, and EC circulation rate(s) may range from about −1.7 mL/min to about 300 mL/min during the cell culture process. During expansion, glucose and/or lactate levels may be analyzed by i-STAT analyzers (e.g., Abbott Point-of-Care, Princeton, NJ, USA) using G and CG4+ cartridges, for example. At harvest, cells were counted (e.g., with a Vi-CELL™ XR cell analyzer, Beckman Coulter, Indianapolis, IN, USA) (FIG. 17), which included quantification of cell viability by trypan blue (FIG. 18), cryopreserved in CryoStar® CS10 freeze medium (e.g., Biolife Solutions, Bothell, WA, USA), and stored in liquid nitrogen vapor phase until further analysis.

Expansion Results

The mean harvest yield, was about $1.02 \times 10^8$ cells (ranging about $4.02 \times 10^7$ to about $1.61 \times 10^8$ cells) with a mean cell viability by trypan blue of about 95.5% (ranging about 93.3% to about 96.8%) and determined by a cell viability counter (Vi-CELL™ XR, Beckman Coulter). The cell expansion yield of $4.0 \times 10^7$-$1.6 \times 10^8$ cells exceeded a minimum $CD34^+$ cell dose of $1.5 \times 10^5$ cells/kg for a single-unit graft and a minimum $CD34^+$ cell dose of $1.0 \times 10^5$ cells/kg for a double-unit graft. This equates to minimum doses of $1.1 \times 10^7$ $CD34^+$ HSCs and $1.4 \times 10^7$ $CD34^+$ HSCs for a single- and a double-unit graft, respectively, for a 70 kg patient.

The mean cell population doubling is about 5.4, the mean cell population doubling time is about 34.9 hours and the mean-fold increase may be 51.0-fold (ranging from about 20.1-fold to about 80.5-fold) over the course of the expansion period. IC medium input perfusion flow rates were adjusted in response to glucose and lactate metabolites and range from about 0.1 to about 0.2 mL/min.

A median cord blood unit (CBU) may contain about $4.4 \times 10^6$ CD34+ HSCs up to a maximum of about $2.0 \times 10^7$ $CD34^+$ HSCs. Using the methods and systems described herein the average expansion yields from a single CBU, may be on the order of $2.2 \times 10^8$ to $1.0 \times 10^9$ CB-derived stem or progenitor cells, for example, with an automated 8 day monoculture cell expansion protocol by simply increasing the cell inoculum from $2.0 \times 10^6$ cells up to $4.4 \times 10^6$-$2.0 \times 10^7$ cells with a full CBU CD34$^+$ cell fraction. This approach, among other things, can increase the cell seeding density from, for example, $1.6 \times 10^4$ cells/mL to $3.6 \times 10^4$-$1.6 \times 10^5$ cells/mL in the perfusion bioreactor, and result in a shorter expansion timeframe that can reduce the potential for cell differentiation.

Cryopreservation

Figure 19:
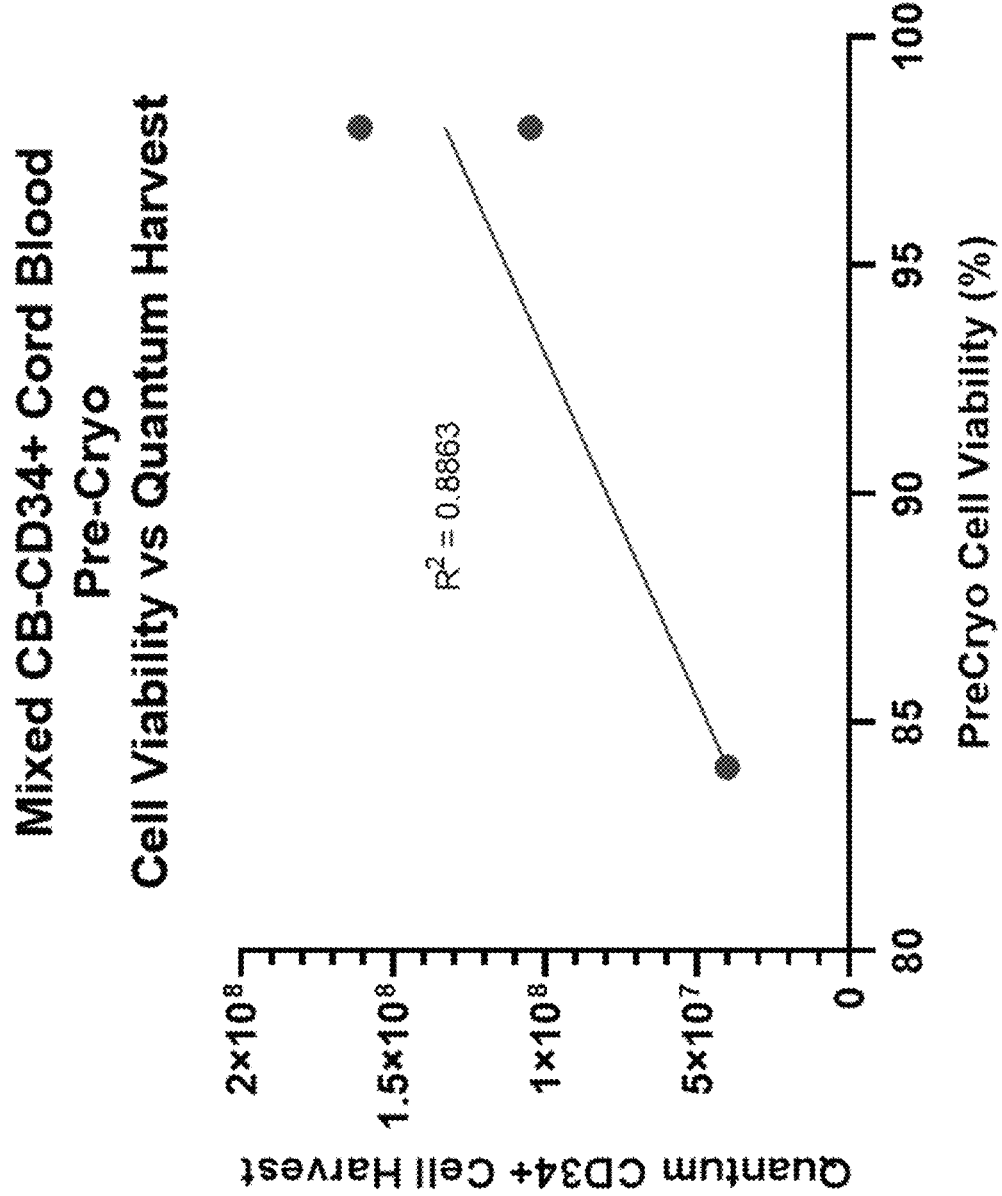
FIG. 19 is a graph showing the correlation of pre-cryopreservation cell viability with cord blood-derived CD34+ cell harvest yield, with Pearson's correlation coefficient of $R^2=0.8863$.

Comparing such CD34+ HSC harvests to the pre-cryopreservation viability across various UCB donors revealed a relationship between expansion yields and pre-cryopreservation cell viability (FIG. 19). Quantum CES CD34+ cell viability is measured at harvest, by trypan blue dye exclusion using a BC Vi CELL™ XR Cell Analyzer. There is a broad range of pre-cryopreservation CD34+ cell viability. In our study, the pre-cryopreservation cell viability ranged from 84% to 98%. Expanding the CB-derived CD34+ HSCs in the Quantum CES generated a mean harvest cell viability of 95%.

Glycolytic Metabolism

Figure 20:
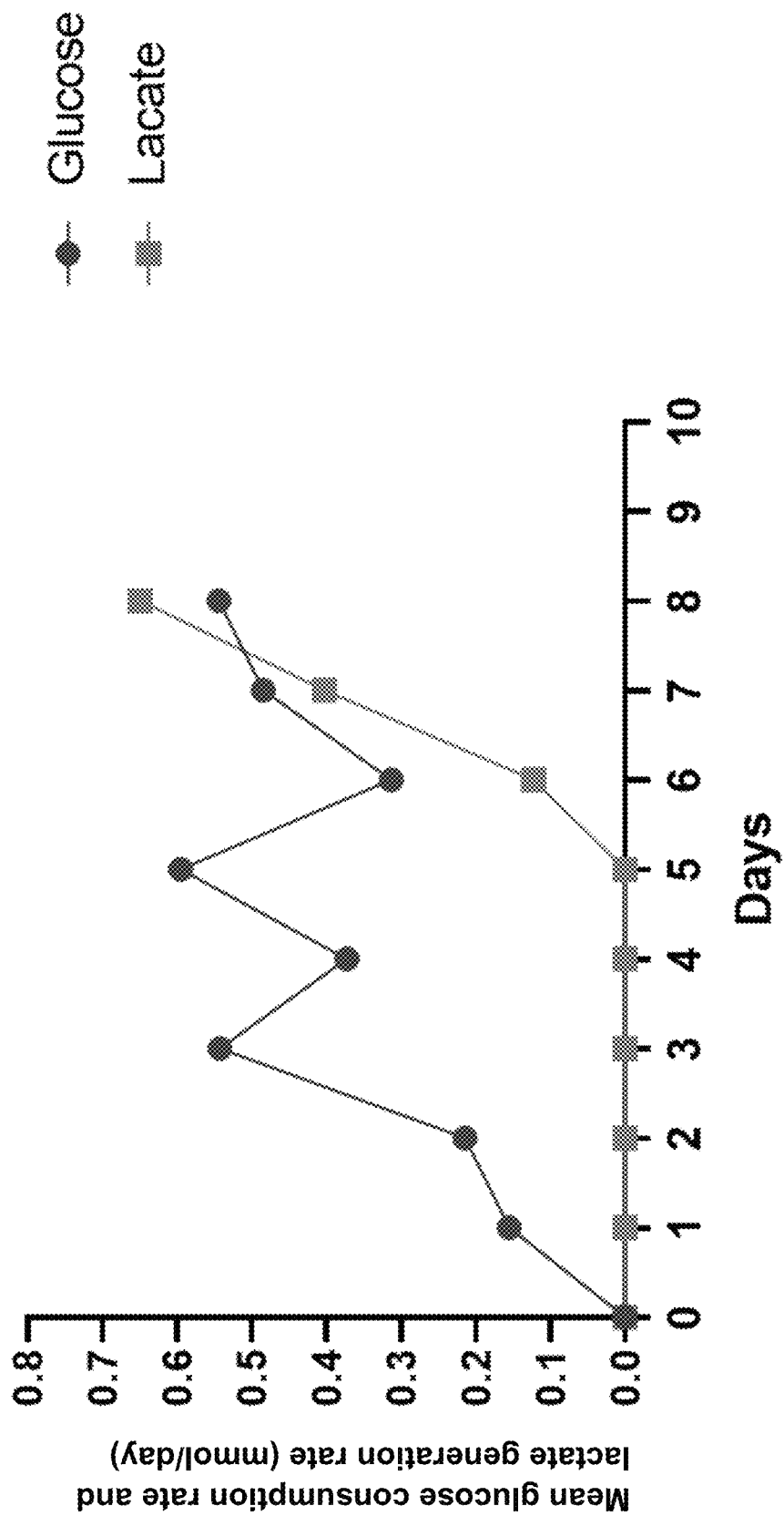
FIG. 20 is a graph showing the mean of CD34+ normalized glucose consumption rate (mmol/day) and lactate generation rate (mmol/day).

Monitoring the glycolytic metabolism shows that the glucose consumption rate may range from 0 to a high of 0.596 on day 5 and the lactate generate rate may range from 0 to a high of 0.650 mmol/day on day 8 (FIG. 20). The difference in peak days for these two metabolites can be attributed to media flow rate adjustments, differential expression of enzymes controlling glycolytic flux, and the demand for central biosynthetic metabolites during cell expansion.

Immunophenotyping

Thawed cell harvest samples at $1 \times 10^6$ cells from each of the three (3) automated CB-derived CD34+ cell expansions are resuspended and washed in complete media, centrifuged at 500 g for 5 minutes, resuspended in 100 µL of BD Flow Stain Buffer, blocked with 5 µL of human BD Fe for 10 minutes prior to staining with, the following conjugated stains: BD Pharmingen anti-human CD45-APC-H7 (Cat. 560178), anti-human CD34-APC (Cat. 560940), anti-human CD133-PE (Cat. 566593), anti-human CD38-BB515 (Cat. 564499), anti-human CD41a-APC-H7 (Cat. 561422), anti-human CD3-PE (Cat. 555333), anti-human CD19-PE (Cat. 555413), anti-human CD56 (555516), anti-human CD15-BB515 (Cat. 565236), and 7-AAD (Cat. 559925). The ISHAGE-gating guidelines for enumerating CD34+ HSCs by flow cytometry may be consulted for the immunophenotyping of expanded cells and the CD34+ HSC populations may be subordinated to the CD45+ parent cell populations (Cytometry, 34:61-70, 1998). In addition, the CD34+ gating strategy was verified with a CD-Chex CD34 peripheral blood control (Streck, CD-Chex CD34, Level 3). Cell sample data were acquired on a BD FACSCanto II flow cytometer with BD FACSDiva™ v9.0 software (10,00 events/sample) and subsequently analyzed with FlowJo™ v10.7 software.

Figure 21A:
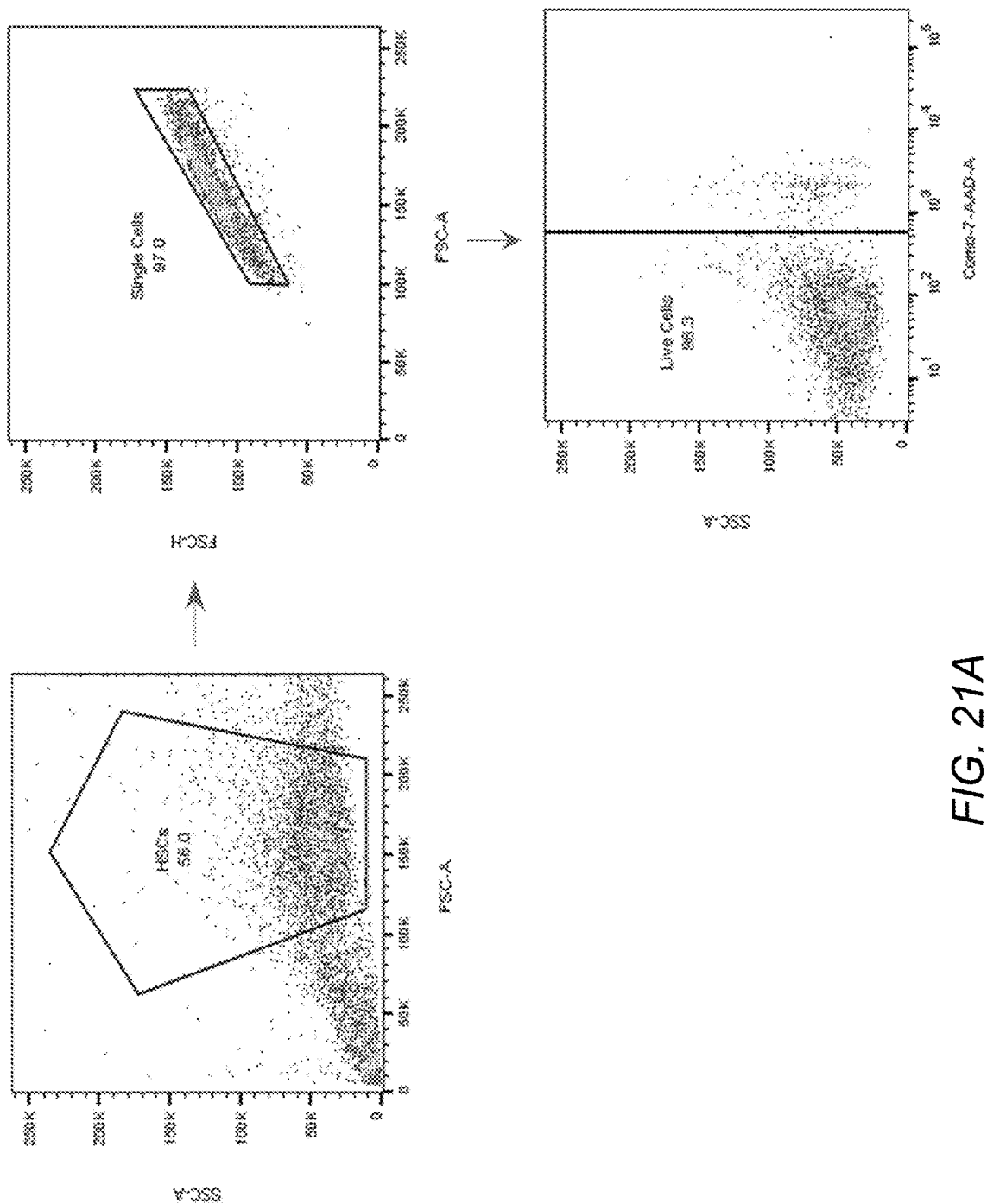
FIG. 21A and FIG. 21B show the FMO gating strategy (FSC-A vs SSC-A→singlets FSC-H vs FSC-A→live cells SSC-A vs &-AAD-A→SSC-A vs CD45-APC-H7→SSC-A (FIG. 21A) vs CD34-APC→CD133-PE vs CD38-BB515 (FIG. 21B)) may be verified with Streck CD-Chex-CD34 Level 3 peripheral blood reference standard. 10,000 events were acquired per sample.
Figure 21B:
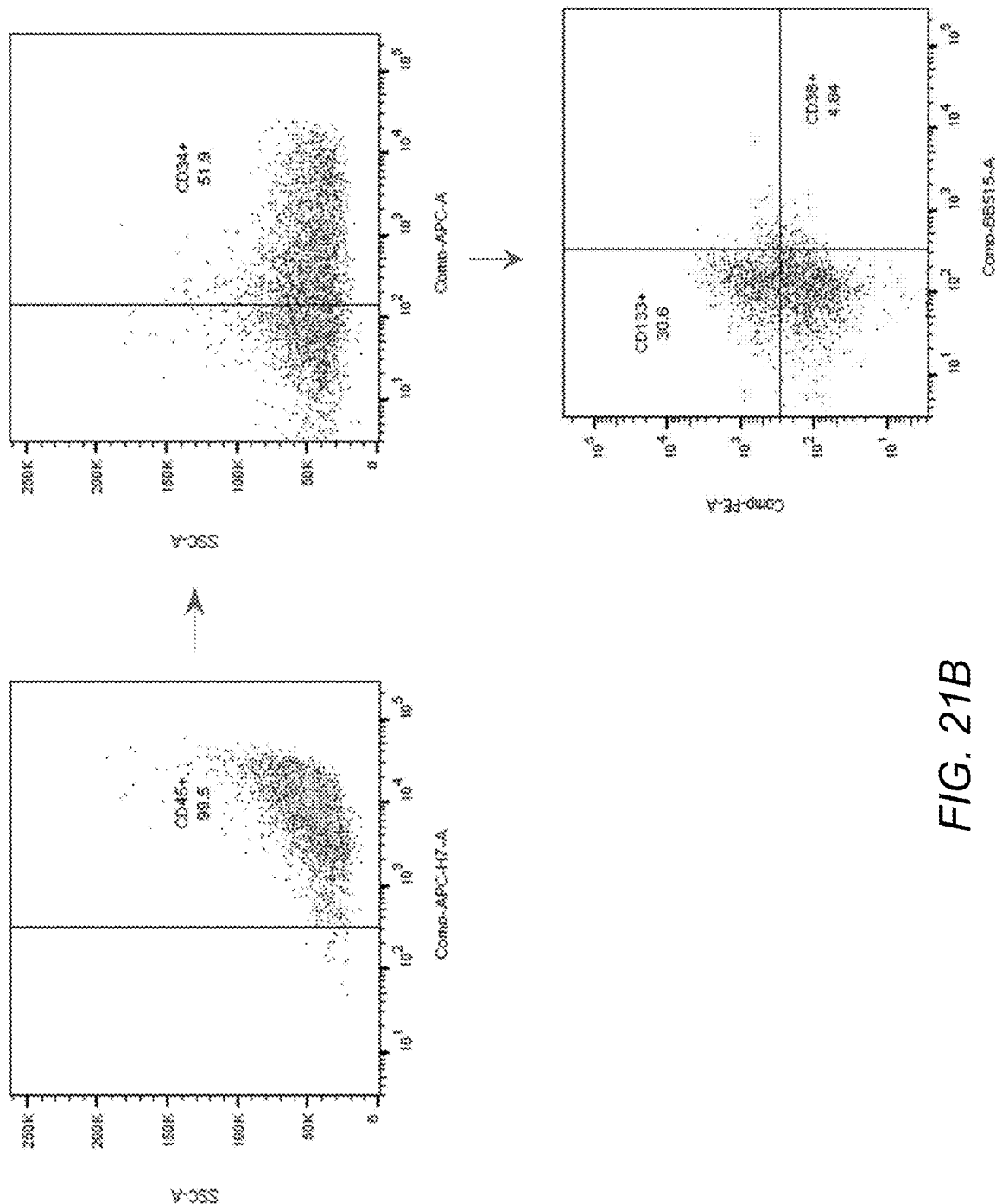

As shown in Table 1 and FIGS. 21A and 21B, flow cytometry indicate the mean frequency of the CD45+/CD34+ immunophenotype to be 54.3% (range 51.9 to 57.9%) and the mean frequency of the more primitive CD133$^+$CD38$^-$ immunophenotype to be 31.8% (range 25.9 to 39.0%) at harvest on Day 8 of automated culture. These results compare favorably with other CD34$^+$ HSC 7-day expansion protocols using SR-1 (CD34$^+$ HSCs 10-25%) media and 21-day CD34+CD38− expansion protocols using Nicotinamide (CD34+ HSCs 0.2-4.4%) media in UCB-derived cell culture. The mean frequency of the differentiated cell lineages was 0.5% for lymphocytes (CD3$^+$, CD19$^+$, CD56$^+$), 27.7% for neutrophils (CD15$^+$), and 26.5% for platelets (CD41a$^+$). The fact that biomarkers for both neutrophils and platelets may be present in expanded CB-derived CD34$^+$ HSC population can be attributed, in part, to the cytokine composition of the expansion media which contains the interleukins IL-3 and IL-6. Although used to support CD34$^+$ cell expansion, both cytokines are also implicated in the development of myeloid cell lineages.

TABLE 1

| Cell Population Hierarchy & Statistics | |
| --- | --- |
| Cell Type | Percentage |
| HSCs | 56.0 |
| Single Cells | 97.0 |
| Live Cells | 96.3 |
| CD45+ | 99.5 |
| CD34+ | 51.9 |
| CD133$^{hi}$ CD38$^{lo}$ | 30.6 |

In Vitro CB-CD34+ Clonal Differentiation

The MethoCult™ CD34$^+$ cell differentiation hematopoietic colony-forming-unit (CFU) assay is performed with MethoCult™ H4034 Optimum medium which may be supplemented with rh-cytokines SCF, GM-CSF, IL-3, G-CSF, and EPO (Stem Cell Technologies, Vancouver, BC, Canada). The cells generated hematopoietic progenitor lineages of GEMM, GM, BFU-E CFUs.

Briefly, Quantum-harvested UCB-derived CD34+ HSCs may be washed, resuspended in IMDM w/2% FBS, diluted in methylcellulose-based medium, vortexed, and seeded at 1.1 mL/35 mm well of medium in multi-well plates using seeding densities of 150, 500, and 1,000 cells/well. The CFU plates may be incubated in a static incubator under 37° C., 5% CO$_2$, humidity conditions for 14 days after which CFUs in each well may be manually counted and scored (n=6) using an Olympus CKX41 inverted microscope at 4× objective magnification with cellSens 2.2 software.

Figure 22:
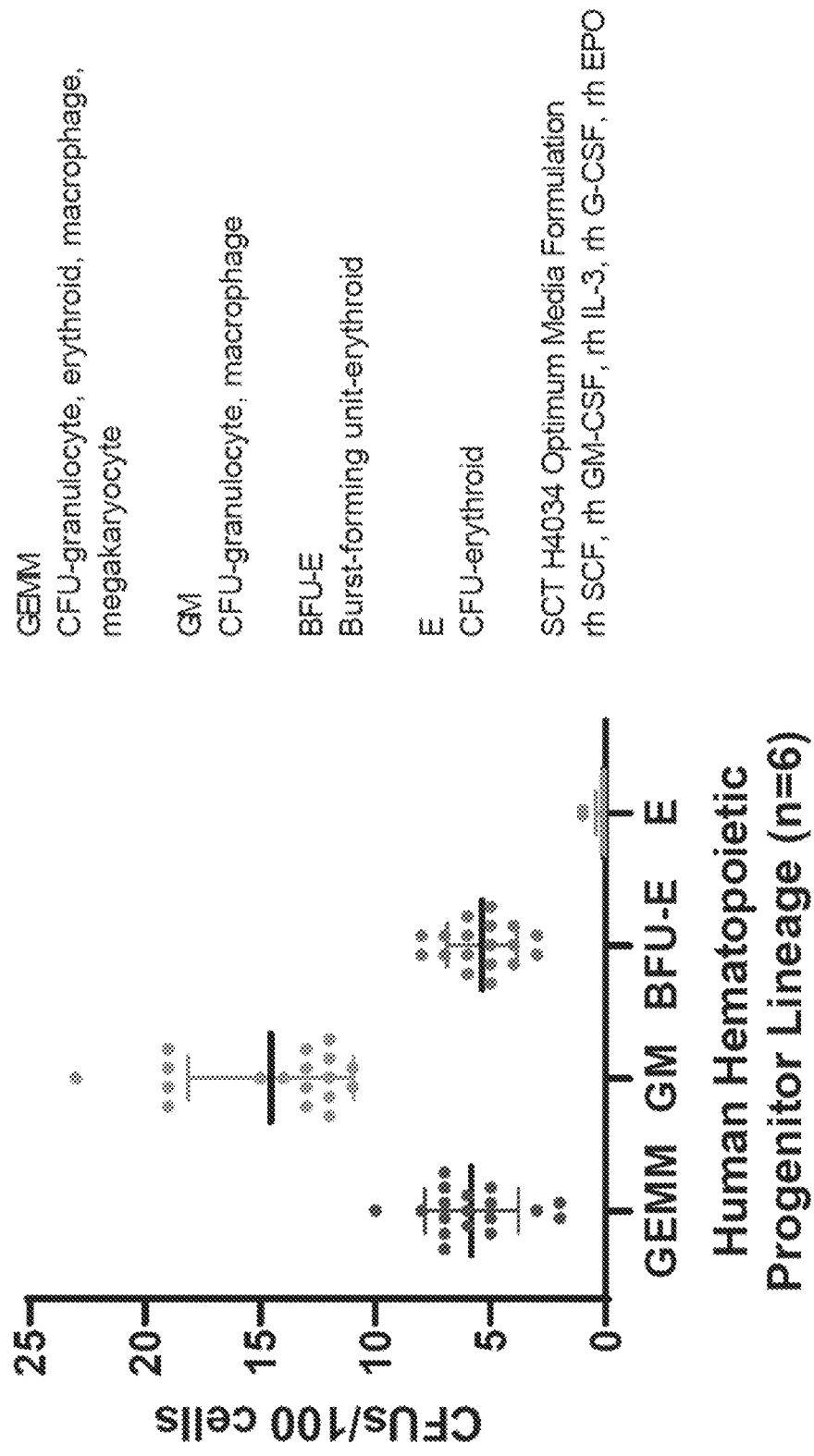
FIG. 22 is a graph showing differentiated colony forming units (CFUs) from Quantum-expanded CD34+ HSCs 14 days post-harvest, with 6 replicates per donor cell line.
Figure 23:
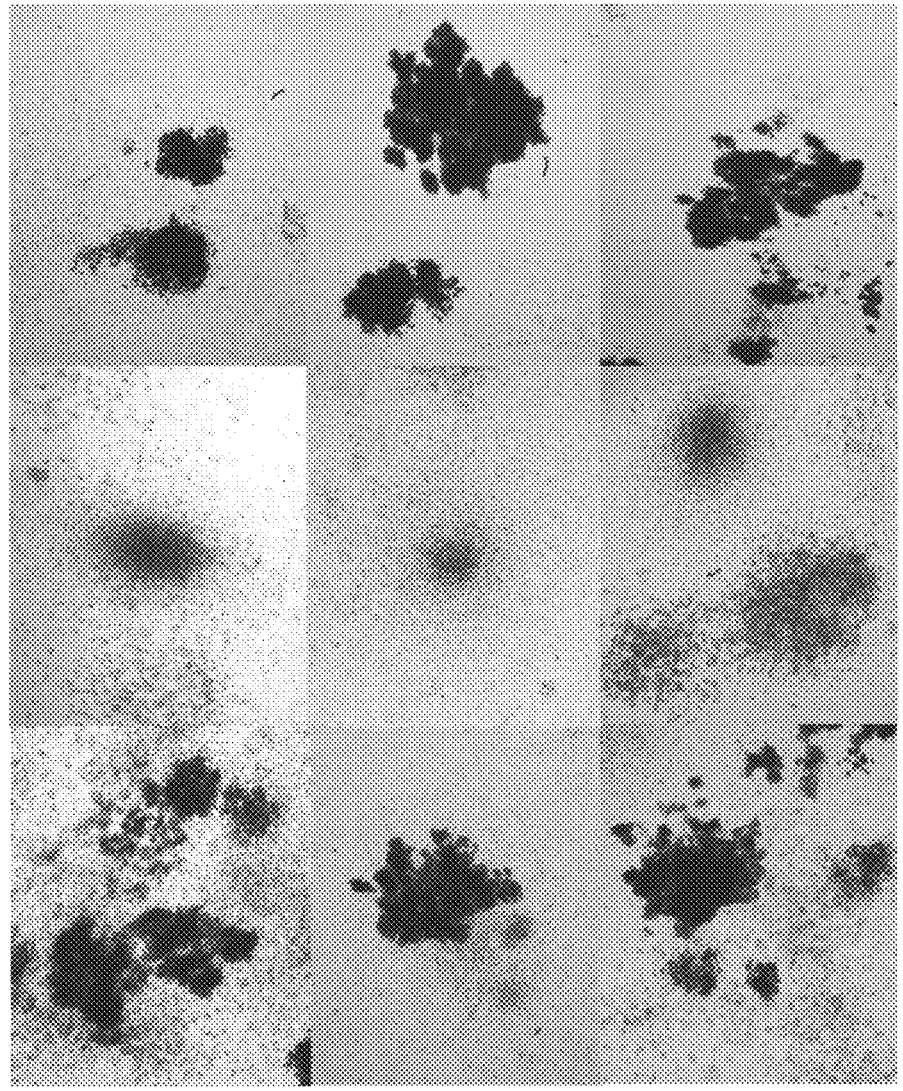
FIG. 23 shows representative images of CFU-granulocyte, erythroid, macrophage, megakaryocyte, CFU-granulocyte and macrophage, and BFU-erythroid lineages.
Figure 24:
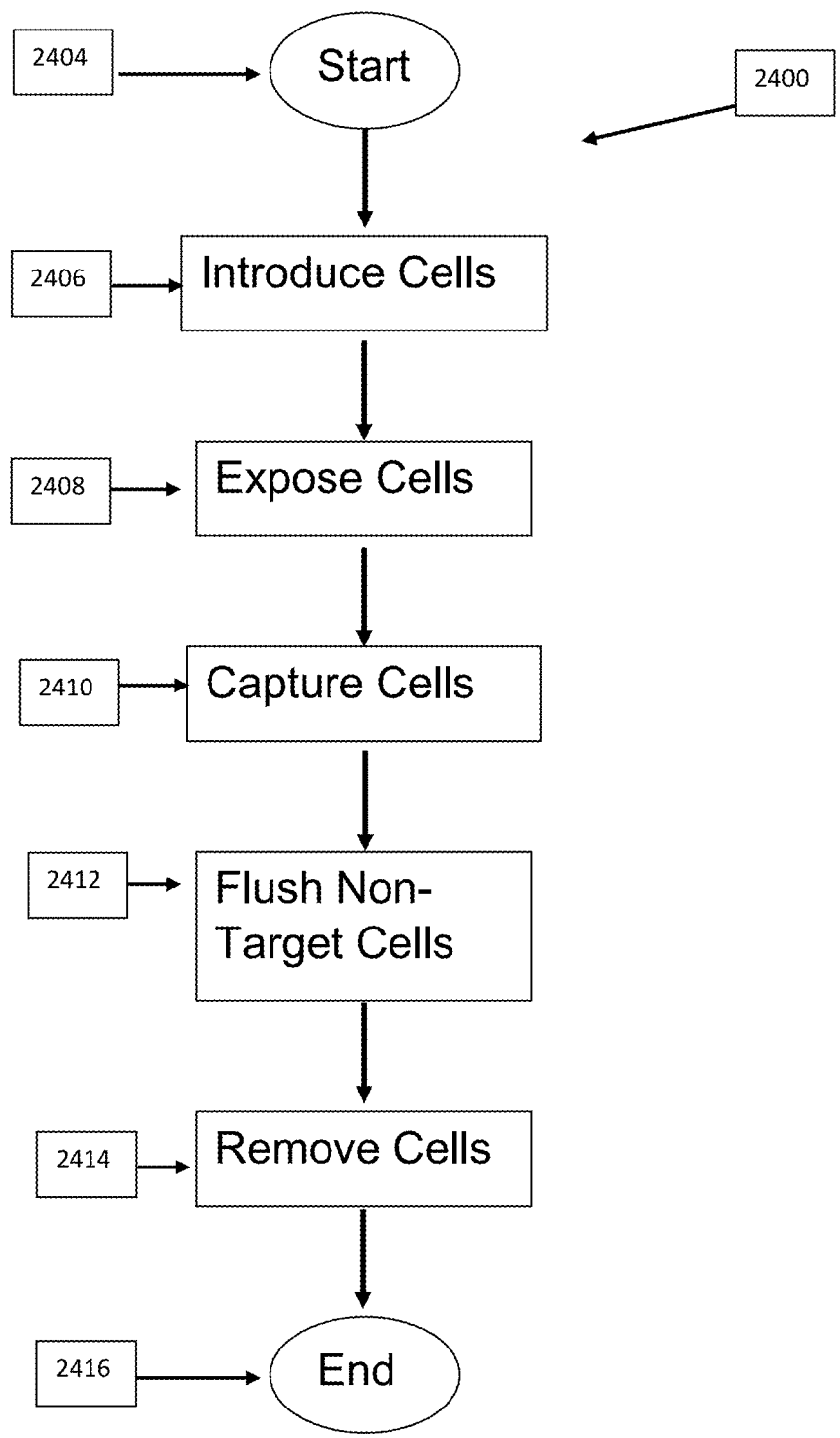
FIG. 24 illustrates flow 2400 that may be performed in embodiments to capture cells (e.g., HSCs). Although specific devices may be described below for performing steps in flow 2400, embodiments are not limited thereto. For example, some steps may be described as performed by parts of a cell processing system (e.g., CES's 500 or 600) or a processor (1100 (FIG. 7)), which may execute steps based on software provided as processor executable instructions. This is done merely for illustrative purposes, and flow 2400 is not limited to being performed by any specific device.

After 14 days of methylcellulose-based cell culture in MethoCult Optimum H4034 cytokine medium, the CB-derived CD34+ cell differentiated CFUs averaged 56% for the GM, 23% for GEMM and 21% for BFU-E progenitor lineages of the total CFUs across the three expanded CB-derived CD34+ cell lines (see, e.g., FIG. 22 and FIG. 23). These CFU example results are comparable to prior studies with methylcellulose H4034 cytokine differentiation of electroporated, genetically unmodified CB-derived CD34+ HSCs where the majority of the lineages may be GM-CFU (60%) clones followed by BFU-E (36%) and GEMM-CFU (10%) clones and/or where the majority of both the genetically modified and unmodified clones may also be GM-CFU (60%) followed by BFU-E (18-20%) and GEMM-CFU (5%) clones. The differences in the relative distribution of the CFU clones among these studies can be attributed to variations in the donor CBU cell sources, stem cell selection methods, genetic modifications in some instances, and the cytokine cocktail formulations used in the expansion of the CB-derived CD34+ HSCs prior to differentiation. Other small molecule supplements formulated with cytokines beyond SR-1, may include nicotinamide (an SIRT1 histone deacetylase and ribosylase inhibitor), valproic acid (a histone HDAC1 inhibitor), and UM171 (an inhibitor of histone HDAC1 deacetylation and LSD1 demethylation) which may be options for hematopoietic stem cell culture for the purpose of increasing CB-derived CD34+ cell amplification and improving engraftment.

The MethoCult™ differentiation assay of harvested cells may generate hematopoietic progenitor lineages of GEMM, GM, BFU-E CFUs. These results, taken as a whole, demonstrated that the automated Quantum® system monoculture protocol(s) can support the expansion of preselected CB-derived CD34+ HSCs for both single and double CBU dose equivalency with minimal lymphocyte residual.

It will be apparent to those skilled in the art that various modifications and variations can be made to the methods and structure of the present invention without departing from its scope. Thus, it should be understood that the present invention is not limited to the specific examples given. Rather, the present invention is intended to cover modifications and variations within the scope of the following claims and their equivalents.

While example implementations and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the present invention.

What is claimed is:

1. A method of expanding cells, comprising:
    applying a coating to an interior lumen of a plurality of hollow fibers of a hollow fiber bioreactor, the plurality of hollow fibers being semi-permeable, the coating including fibronectin configured to adhere to the interior lumen and stromal cell-derived factor 1 (SDF-1) configured to both adhere to the fibronectin and retain CD34+ hematopoietic stem cells thereto;
    introducing a first plurality of cells into the plurality of hollow fibers of the hollow fiber bioreactor, the first plurality of cells including CD34+ hematopoietic stem cells derived from at least one of cord blood, bone marrow, and peripheral blood;
    maintaining and concentrating the first plurality of cells within the plurality of hollow fibers by directing fluid into opposite ends of the hollow fiber bioreactor simultaneously;
    exposing the first plurality of cells in the hollow fibers to growth conditions; and
    expanding at least a portion of the first plurality of cells in the hollow fibers of the bioreactor to generate a second plurality of expanded target cells including CD34+ hematopoietic stem cells that are expanded at least 50-fold, by introducing into the plurality of hollow fibers, and into contact with the first plurality of cells, the following:
    soluble growth supporting cytokines including at least one of SCF, TPO, Flt-3L, IL-3, and IL-6;
    an aryl receptor antagonist; and
    glial cell-derived neurotrophic factor (GDNF).

2. The method of claim 1, wherein the first plurality of cells is introduced to the plurality of hollow fibers without any prior purification.

3. The method of claim 1, wherein exposing the first plurality of cells in the hollow fibers to growth conditions includes exposing the first plurality of cells to one or more growth factors including FMS-like Tyrosine Kinase 3 Ligand (Flt-3L), Stem Cell Factor (SCF), thrombopoietin (TPO), glial-derived neurotrophic factor (GDNF), and combinations thereof.

4. The method of claim 1, wherein exposing the first plurality of cells in the hollow fibers to growth conditions includes circulating a cell growth media through the interior lumen of the hollow fibers.

5. The method of claim 1, wherein exposing the first plurality of cells in the hollow fibers to growth conditions includes circulating a cell growth media through an extracapillary side of the hollow fibers.

6. The method of claim 1, wherein introducing the first plurality of cells into the hollow fibers includes:
    circulating a portion of the plurality of cells within the interior lumen of the hollow fibers;
    stopping the circulation to allow one or more of the portion of the plurality of cells to contact a first portion of the interior lumen of the hollow fibers;
    rotating the hollow fiber bioreactor 180 degrees from an initial position;
    circulating another portion of the plurality of cells within the interior lumen of the hollow fibers; and
    stopping the circulation to allow one or more of the other portion of the plurality of cells to contact a second portion of the interior lumen of the hollow fibers.

7. The method of claim 1, wherein the first plurality of cells is introduced simultaneously at opposing ends of the hollow fibers.

8. The method of claim 1, wherein the coating includes a protein moiety.

9. The method of claim 1, wherein the aryl receptor antagonist is at least one of StemRegenin I (SRI) and UMI71.

10. The method of claim 1, wherein the soluble growth supporting cytokines including at least one of SCF, TPO, Flt-3L, IL-3, and IL-6 is included in a cytokine cocktail having a concentration within a range of about 0.5% to about 2% weight per volume.

11. The method of claim 1, wherein the GDNF is at a concentration of at least 10 ng/mL.

12. The method of claim 1, wherein the hollow fibers include a first media in the interior lumen and a second media in contact with an extracapillary side of the hollow fibers.

13. The method of claim 12, wherein the media in the interior lumen is concentrated in at least one component relative to the concentration of the same component on the extracapillary side of the hollow fibers.

14. The method of claim 13, wherein the component is the GDNF.

15. The method of claim 13, wherein the component includes at least one of SR-I, SCF, TPO, Flt-3L, IL-3, IL-6, SDF-1, and fibronectin.

16. The method of claim 1, wherein the second plurality of cells is maintained within, and concentrated within, the plurality of hollow fibers by simultaneous flow of the fluid into opposite ends of the hollow fiber bioreactor.

17. The method of claim 1, wherein the first plurality of cells includes enriched CD34+ cells.

18. The method of claim 1, wherein the first plurality of cells includes at least 2 million cells.

19. The method of claim 1, wherein the soluble growth supporting cytokines including at least one of SCF, TPO, Flt-3L, IL-3, and IL-6 are at a concentration of 1% by volume of 7 mL to 10,000 mL and multiples thereof.

20. The method of claim 1, wherein introducing the first plurality of cells includes introducing $2\times10^6$ cord blood-derived CD34+ cells.

21. The method of claim 1, wherein introducing the first plurality of cells includes introducing $1.6\times10^4$ cord blood-derived CD34+ cells per mL of intracapillary complete cell culture medium including at least one of SCF, TPO, Flt-3L, IL-3, IL-6, GDNF, and SR-1 into the hollow fiber bioreactor.

22. The method of claim 1, wherein the second plurality of expanded target cells includes at least $1.05\times10^8$ CD34+ hematopoietic stem cells.

23. The method of claim 1, wherein introducing the first plurality of cells into the plurality of hollow fibers includes introducing the first plurality of cells into only first ends of the plurality of hollow fibers while introducing media counterflow into second ends of the plurality of hollow fibers, the first ends are opposite to the second ends.

24. The method of claim 1, wherein introducing the first plurality of cells into the plurality of hollow fibers includes introducing the first plurality of cells into only first ends of the plurality of hollow fibers without introducing counterflow into second ends of the plurality of hollow fibers, the first ends are opposite to the second ends.

25. The method of claim 1, wherein applying the coating to the interior lumen of the plurality of hollow fibers of the hollow fiber bioreactor includes applying the coating by ultrafiltration.

26. The method of claim 1, wherein the soluble growth supporting cytokines are maintained and concentrated within the plurality of hollow fibers by introducing fluid into opposite ends of the hollow fiber bioreactor simultaneously.

* * * * *